United States Patent
Muratoglu et al.

(10) Patent No.: US 9,441,081 B2
(45) Date of Patent: Sep. 13, 2016

(54) CROSS-LINKING OF ANTIOXIDANT-CONTAINING POLYMERS

(75) Inventors: Orhun K. Muratoglu, Cambridge, MA (US); Stephen H. Spiegelberg, Winchester, MA (US)

(73) Assignees: The General Hospital Corp., Boston, MA (US); Cambridge Polymer Group, Inc., Boston, MA (US)

( * ) Notice: Subject to any disclaimer, the term of this patent is extended or adjusted under 35 U.S.C. 154(b) by 1470 days.

(21) Appl. No.: 12/041,249

(22) Filed: Mar. 3, 2008

(65) Prior Publication Data

US 2008/0215142 A1 Sep. 4, 2008

Related U.S. Application Data

(60) Provisional application No. 60/892,682, filed on Mar. 2, 2007, provisional application No. 60/915,169, filed on May 1, 2007.

(51) Int. Cl.

| | |
|---|---|
| A61L 27/16 | (2006.01) |
| A61L 27/44 | (2006.01) |
| A61L 27/50 | (2006.01) |
| A61L 29/04 | (2006.01) |
| A61L 29/14 | (2006.01) |
| A61L 31/04 | (2006.01) |
| A61L 31/14 | (2006.01) |
| C08K 5/00 | (2006.01) |
| C08K 3/00 | (2006.01) |
| C08L 23/06 | (2006.01) |
| C08J 3/28 | (2006.01) |
| C08J 3/22 | (2006.01) |

(52) U.S. Cl.
CPC ........ *C08J 3/28* (2013.01); *A61L 27/16* (2013.01); *A61L 29/041* (2013.01); *A61L 31/048* (2013.01); *C08J 3/226* (2013.01); *C08J 2323/06* (2013.01); *C08J 2423/00* (2013.01)

(58) Field of Classification Search
CPC ..... A61L 27/44; A61L 27/16; A61L 27/505; A61L 29/143; A61L 29/041; A61L 31/143; A61L 31/048; C08F 6/001; C08F 10/02; C08K 3/0041; C08K 5/005; C08L 23/06

USPC .............. 623/1.49, 23.58; 523/105
See application file for complete search history.

(56) References Cited

U.S. PATENT DOCUMENTS

| | | | |
|---|---|---|---|
| 5,286,772 A | 2/1994 | Rapoport | 524/345 |
| 5,827,904 A | 10/1998 | Hahn | 523/113 |
| 5,879,400 A | 3/1999 | Merrill et al. | 623/22 |
| 6,017,975 A * | 1/2000 | Saum et al. | 522/161 |
| 6,448,315 B1 | 9/2002 | Lidgren et al. | 524/110 |
| 6,641,617 B1 | 11/2003 | Merrill et al. | 623/23.58 |
| 7,166,650 B2 | 1/2007 | Muratoglu et al. | 522/161 |
| 7,431,874 B2 | 10/2008 | Muratoglu et al. | 264/235 |
| 8,318,065 B2 * | 11/2012 | Muratoglu et al. | 264/235 |
| 8,425,815 B2 * | 4/2013 | Muratoglu et al. | 264/109 |
| 8,426,486 B2 * | 4/2013 | Muratoglu et al. | 522/157 |
| 2004/0156879 A1 * | 8/2004 | Muratoglu et al. | 424/423 |
| 2005/0124718 A1 * | 6/2005 | Muratoglu et al. | 522/161 |
| 2007/0265369 A1 | 11/2007 | Muratoglu et al. | |
| 2008/0214692 A1 | 9/2008 | Muratoglu et al. | |

FOREIGN PATENT DOCUMENTS

| | | |
|---|---|---|
| WO | WO97/29793 | 8/1997 |
| WO | WO01/05337 | 1/2001 |
| WO | WO01/80778 | 11/2001 |
| WO | WO02/26464 | 4/2002 |
| WO | WO2005/074619 | 8/2005 |
| WO | WO2007/024689 | 3/2007 |

OTHER PUBLICATIONS

Jahan et al., Journal of Biomedical Materials Research 25: 1005-1017 (1991).
Kashiwabara et al., Radiat. Phys. Chem. 37(1): 43-46 (1991).
Oral et al., Biomaterials 26: 6657-6663 (2005).
Oral et al., Biomaterials 27: 917-925 (2006).
Sutula et al., Clinical Orthopaedics and Related Research 319: 28-40 (1995).
Mori et al., Mechanical Behavior of UHMWPE When Mixed with Vitamin E (47th Annual Meeting, Orthopaedic Research Society, San Francisco, CA (Feb. 25-28, 2001).

* cited by examiner

*Primary Examiner* — Liam J Heincer
(74) *Attorney, Agent, or Firm* — Perkins Coie LLP

(57) ABSTRACT

The present invention relates to methods for making cross-linked, oxidatively stable, and highly crystalline polymeric materials. The invention also provides methods of treating irradiation-cross-linked antioxidant-containing polymers and materials used therewith.

31 Claims, 23 Drawing Sheets

CROSS-LINKING OF ANTIOXIDANT-CONTAINING POLYMERS

CROSS-LINKING OF ANTIOXIDANT-CONTAINING POLYMERS

This application claims priority to U.S. Application Ser. Nos. 60/915,169, filed May 1, 2007 and 60/892,682, filed Mar. 2, 2007; the entireties of which are hereby incorporated by reference.

FIELD OF THE INVENTION

The present invention relates to methods for making cross-linked oxidatively stable polymeric materials. Methods of treating irradiation-cross-linked antioxidant-containing polymers and materials used therewith also are provided.

BACKGROUND OF THE INVENTION

Antioxidant-containing polymer compositions lose their efficiency of cross-linking when subjected to ionizing radiation because of the free radical protective activity of the antioxidant. For certain applications, such as medical applications like load bearing polymers, cross-linking is beneficial to reduce the wear rate of the polymer. Radiation cross-linking has been shown to reduce the wear rate of polymeric material and thus extend the longevity of total joint reconstructions. However, residual free radicals created by radiation compromise the long-term oxidative stability of the polymer. Therefore, it is crucial to either eliminate or stabilize the free radicals so that deleterious oxidation is avoided or minimized. One method of free radical elimination through irradiation and melting were described by Merrill et al. (see U.S. Pat. No. 5,879,400). This is an acceptable method; however, such a melt history also reduces the crystallinity of the polyethylene and thus affects its mechanical and fatigue properties (see Oral et al., *Biomaterials*, 27:917-925 (2006)).

Other methods that avoid melting after irradiation is the one described, among other things, by Muratoglu and Spiegelberg (see US 2004/0156879). These methods use an antioxidant, such as α-tocopherol, to stabilize the free radicals in irradiated polymeric material and prevent long-term oxidation. According to certain embodiments of these methods, α-tocopherol can be incorporated into polymeric material after irradiation through contact and diffusion.

α-Tocopherol can be used to lessen or eliminate reactivity of the residual free radicals in irradiated UHMWPE to prevent oxidation. The incorporation of α-tocopherol into irradiated UHMWPE can be achieved through either blending α-tocopherol with the UHMWPE powder prior to consolidation or diffusing the α-tocopherol into UHMWPE after consolidation of powder, both of which are taught in U.S. application Ser. No. 10/757,551 (US 2004/0156879). The latter also can be performed after the consolidated UHMWPE is irradiated. Since radiation cross-links the UHMWPE and thus increases its wear resistance, it can be beneficial to irradiate the consolidated UHMWPE in its virgin state without any α-tocopherol present. On the other hand, cross-linking and melting has been shown to decrease certain mechanical properties and fatigue resistance of UHMWPE (see Oral et al., Mechanisms of decrease in fatigue crack propagation resistance in irradiated and melted UHMWPE, *Biomaterials*, 27 (2006) 917-925). Wear of UHMWPE in joint arthroplasty is a surface phenomenon whereas fatigue crack propagation resistance is largely a property of the bulk. Therefore, UHMWPE with high cross-linking on the surface and less cross-linking in the bulk can be beneficial as an alternate bearing in joint arthroplasty. Oral et al. (Characterization of irradiated blends of α-tocopherol and UHMWPE, *Biomaterials*, 26 (2005) 6657-6663) have shown that when present in UHMWPE, α-tocopherol reduces the efficiency of cross-linking of the polymer during irradiation. Muratoglu et al. (see US 2004/0156879) described, among other things, high temperature doping and/or annealing steps to increase the depth of penetration of α-tocopherol into irradiated UHMWPE. Muratoglu et al. (see U.S. application Ser. No. 11/465,544, filed Aug. 18, 2006; PCT/US2006/032329 Published as WO 2007/024689) described, among other things, annealing in supercritical carbon dioxide to increase depth of penetration of α-tocopherol into irradiated UHMWPE. UHMWPE medical implants can have a thickness of up to 30 mm and sometimes larger. Penetrating such large implants with α-tocopherol by diffusion can take a long time, however. Also it is preferable in some embodiments to diffuse α-tocopherol into an irradiated UHMWPE preform and subsequently machine that preform to obtain the finished implant. The preform has to be larger than the implant and therefore the diffusion path for α-tocopherol is increased.

In order to eliminate free radicals, several further methods can be used such as melting (see, e.g., Muratoglu et al. US 2004/0156879), mechanical deformation and recovery (see, e.g., Muratoglu et al., US 2005/0124718) or high pressure crystallization (see, e.g., Muratoglu et al. U.S. application Ser. No. 10/597,652; PCT/US05/003305 published as WO 2005/074619), which are incorporated herein by reference.

Post-irradiation melting also has been advanced as a method of eliminating the free radicals. This method has been successful without compromising the oxidative stability of the polymer, but reduces the crystallinity and in turn certain mechanical properties of the polymer. For certain human joint applications and certain high-stress designs, a decrease in certain mechanical properties is to be avoided. Alternative approaches to post-irradiating melting also have been developed. For instance, post-irradiation mechanical deformation or post-irradiation antioxidant diffusion does not adversely affect the mechanical properties of the irradiated polymer. Another method is to blend the polymer resin, powder or flakes with an antioxidant and subject it to ionizing radiation.

As mentioned above, when the radiation cross-linking is carried out in the presence of the antioxidant higher radiation dose levels need to be utilized to achieve the desired level of reduction in wear; however at higher radiation dose levels the antioxidant monotonically loses its potency as well, compromising the long-term oxidative stability of the polymer. Early studies with accelerated aging of antioxidant-containing polymers (0.1 wt % and 0.3 wt % vitamin-E/UHMWPE blend irradiated to 100 kGy and aged in a pressure vessel at 80° C. in oxygen for 2 weeks; see Oral et al. Biomaterials 2005 26(33):6657-6663) showed the oxidative stability of the polymer to be unaffected. We have discovered that when these irradiated polymers are stored (for example, stored on the shelf at room temperature) for a several months, they start showing signs of oxidation. Therefore, there is a potential for oxidative instability for irradiated antioxidant-containing polymers. This was an unexpected outcome as the accelerated aging methods were largely accepted to indicate long-term real aging behavior of UHMWPE. Nevertheless, accelerated aging data does not necessarily correlate or replicate real aging experience.

The addition of certain antioxidants into certain polymers inhibits the ability of the polymer to cross-link when subjected to ionizing radiation. Cross-linking typically takes place by the recombination reaction of two free radicals. Certain antioxidants, such as vitamin-E, could inhibit this recombination reaction through a number of possible mechanisms. This reduction in cross-linking efficiency of polymers containing antioxidants requires higher radiation dose levels to achieve the same cross-link density as that of radiation cross-linked virgin polymer (without antioxidant). At higher radiation dose levels, the activity of the antioxidant is reduced in favor for the increased cross-linking efficiency of the host polymer. However, the reduction in the antioxidant activity could compromise the oxidative stability of the host polymer. Therefore, new and alternative methods and approaches are desirable to achieve a desired cross-link density while minimizing the loss of activity of the antioxidant.

This application describes methods not found in the field for making antioxidant-doped, cross-linked polymeric materials having oxidative stability, for example, antioxidant-doped cross-linked ultra-high molecular weight polyethylene (UHMWPE), by post-irradiation heat treatment (such as annealing) of the antioxidant-containing UHMWPE, and materials used therein.

SUMMARY OF THE INVENTION

The present invention relates generally to methods for making cross-linked oxidatively stable polymeric materials, and products produced thereby. More specifically, the invention relates to methods of heat treatment of irradiation-cross-linked, antioxidant-containing polymers and materials used therewith are provided thereby. More specifically, the invention relates to methods of manufacturing antioxidant-doped, cross-linked polymeric materials having oxidative stability, for example, antioxidant-doped cross-linked ultra-high molecular weight polyethylene (UHMWPE) made by post-irradiation annealing of the antioxidant-containing UHMWPE, and materials used therein.

In one embodiment, the invention provides methods of making a highly cross-linked, oxidatively stable highly crystalline UHMWPE, made by a process comprising: a) blending antioxidant (for example, vitamin E) with UHMWPE resin, powder, or flake; b) consolidating the blend; c) irradiating the consolidated polymeric material at a temperature below the melting point; and d) annealing the consolidated polymeric material in air or under an inert environment at a temperature below the melting temperature of the polymeric material, thereby forming a highly cross-linked, oxidatively stable, and highly crystalline polymeric material.

In another embodiment, the invention provides a highly cross-linked, oxidatively stable highly crystalline UHMWPE, made by a process comprising: a) blending antioxidant (for example, vitamin E) with UHMWPE resin, powder, or flake; b) consolidating the blend; c) irradiating the consolidated polymeric material at a temperature below the melting point; and d) quenching the residual free radicals by mechanical deformation in air or under an inert environment at a temperature below the melting temperature of the polymeric material, thereby forming a highly cross-linked, oxidatively stable, and highly crystalline polymeric material.

In another embodiment, the invention provides a highly cross-linked, oxidatively stable highly crystalline UHMWPE, made by a process comprising: a) blending antioxidant (for example, vitamin E) with UHMWPE resin, powder, or flake; b) mixing the blend with virgin UHMWPE resin, powder, or flake, thereby forming a composition having antioxidant rich and poor regions/domains; c) consolidating the composition, thereby forming a polymeric material having antioxidant rich and poor regions/domains; d) irradiating the consolidated polymeric material at temperature below the melting point; and e) annealing the consolidated polymeric material in air or under an inert environment at a temperature below the melting temperature of the polymeric material, thereby forming a highly cross-linked, oxidatively stable, and highly crystalline polymeric material.

In another embodiment, the invention provides a highly cross-linked, oxidatively stable highly crystalline UHMWPE, made by a process comprising: a) blending antioxidant (for example, vitamin E) with UHMWPE resin, powder, or flake; b) mixing the blend with virgin UHMWPE resin, powder, or flake, thereby forming a composition having antioxidant rich and poor regions/domains; c) consolidating the composition, thereby forming a polymeric material having antioxidant rich and poor regions/domains; d) irradiating the consolidated polymeric material at temperature below the melting point; and e) quenching the residual free radicals by mechanical deformation in air or under an inert environment at a temperature below the melting temperature of the polymeric material, thereby forming a highly cross-linked, oxidatively stable, and highly crystalline polymeric material.

In another embodiment, the invention provides a highly cross-linked and oxidatively stable polymeric material comprising a blend of one or more polymers and an additive (such as an antioxidant, vitamin E, for example), wherein the blend is radiation cross-linked above room temperature, and wherein the blend having a crosslink density above about 0.13 mol/dm$^3$.

In another embodiment, the invention provides a highly cross-linked and oxidatively stable polymeric material comprising a blend of one or more polymers and an additive (such as an antioxidant, vitamin E, for example), wherein the blend is radiation cross-linked with at least about 100 kGy dose above the room temperature and the resulting crosslink density is above that of room temperature irradiated polymeric material.

In another embodiment, the invention provides a highly cross-linked and oxidatively stable polymeric material comprising a blend of one or more polymers and an additive (such as an antioxidant, vitamin E, for example), wherein the blend is radiation cross-linked above room temperature, and wherein the blend having at least 2 melting peaks during the first melting cycle of DSC (for example, during the first heating in DSC).

In another embodiment, the invention provides a highly cross-linked and oxidatively stable polymeric material comprising a blend of one or more polymers and an additive (such as an antioxidant, vitamin E, for example), wherein the blend is radiation cross-linked above room temperature, and wherein the blend having a crystallinity of less than about 58% after one melting cycle in DSC (for example, during the second or later heating step in DSC).

In another embodiment, the invention provides a highly cross-linked and oxidatively stable polymeric material comprising a blend of one or more polymers and an additive (such as an antioxidant, vitamin E, for example), wherein the blend is radiation cross-linked above room temperature, and wherein the blend having at least 2 melting peaks during the re-melting cycle in DSC (for example, during the second or later heating step in DSC).

In another embodiment, the invention provides a highly cross-linked and oxidatively stable polymeric material comprising a blend of one or more polymers and an additive (such as an antioxidant, vitamin E, for example), wherein the blend is sequentially irradiated and annealed.

In another embodiment, the invention provides a highly cross-linked and oxidatively stable polymeric material comprising a blend of one or more polymers and an additive (such as an antioxidant, vitamin E, for example), wherein the blend is radiation cross-linked such that at least some portion of the radiation dose is administered below 100° C. and the remaining radiation dose is administered above 40° C. so as to minimize warm irradiation induced fracture of the polyethylene.

In another embodiment, the polymeric material is compression molded to another piece or a medical implant, thereby forming an interface or an interlocked hybrid material; or the antioxidant blended polymeric material is compression molded to another piece or a medical implant, thereby forming an interface or an interlocked hybrid material; or the consolidated antioxidant doped polymeric material is compression molded to another piece, thereby forming an interface and an interlocked hybrid material; or the consolidated polymeric material is compression molded to another piece, thereby forming an interface and an interlocked hybrid material.

In another embodiment, irradiated and melted material is compression molded onto the surface of the antioxidant-doped or -blended polymeric material or implant. In another embodiment, irradiated, mechanically deformed and thermally treated (below the melt) material is compression molded onto the surface of the antioxidant doped or blended polymeric material or implant. In another embodiment, irradiated and high pressure crystallized polymeric material is compression molded onto the surface of the antioxidant-doped or -blended polymeric material or implant.

In another embodiment, the invention provides an oxidation-resistant cross-linked polymeric material having a spatially controlled antioxidant distribution, wherein the polymeric material is obtainable by any of the methods described herein.

According to one aspect of the invention, the doping is carried out by soaking the medical implant in the antioxidant, preferably, for about half an hour to about 100 hours or more, more preferably, for about an hour, about 2, 3, 4, 5, 6, 7, 8, 9, 10, 11, 12, 13, 14, 15, or about 16 hours, and/or the antioxidant is heated to about 120° C. and the doping is carried out at about 120° C., and/or the antioxidant is warmed to about room temperature and the doping is carried out at room temperature or at a temperature between room temperature and the peak melting temperature of the polymeric material or less than about 137° C., and/or the cross-linked polymeric material is heated at a temperature below the melt of the cross-linked polymeric material. Depending upon the polymeric material selected, heat treatment, homogenization and other temperatures are determined in view of melting temperatures of the selected polymeric material.

According to another aspect of the invention, the polymeric material is a polyolefin, a polypropylene, a polyamide, a polyether ketone, or a mixture thereof; wherein the polyolefin is selected from a group consisting of a low-density polyethylene, high-density polyethylene, linear low-density polyethylene, ultra-high molecular weight polyethylene (UHMWPE), or a mixture thereof, and wherein the polymeric material is polymeric resin, including powder, flakes, particles, or the like, or a mixture thereof or a consolidated resin.

According to another aspect of the invention, polymeric material is a hydrogel, such as poly (vinyl alcohol), poly (acrylamide), poly (acrylic acid), poly(ethylene glycol), blends thereof, or interpenetrating networks thereof, which can absorb water such that water constitutes at least 1 to 10,000% of their original weight, typically 100 wt % of their original weight or 99% or less of their weight after equilibration in water.

In another embodiment of the invention, the implant comprises medical devices selected from the group consisting of acetabular liner, shoulder glenoid, patellar component, finger joint component, ankle joint component, elbow joint component, wrist joint component, toe joint component, bipolar hip replacements, tibial knee insert, tibial knee inserts with reinforcing metallic and polymeric posts, intervertebral discs, interpositional devices for any joint, sutures, tendons, heart valves, stents, vascular grafts.

In another embodiment of the invention, the medical implant is a non-permanent medical device, for example, a catheter, a balloon catheter, a tubing, an intravenous tubing, or a suture.

In one embodiment, the antioxidant-doped or -blended polymeric material is homogenized at a temperature below the melting point of the polymeric material for about an hour to several days.

In another embodiment of the invention, the oxidation-resistant cross-linked medical implant preform is further homogenized following the irradiation step by heating to a temperature below the melt to allow diffusion of the antioxidant from the antioxidant rich to antioxidant poor regions and oxidative stability throughout the medical device.

In another embodiment of the invention, the antioxidant-doped polymeric material, the oxidation-resistant medical implant preform, or the medical implant preform is homogenized before and/or after irradiation, by thermally annealing at a temperature below the melting point of the polymeric material.

In another embodiment of the invention, the antioxidant is diffused to a depth of about 5 mm or more from the surface, for example, to a depth of about 3-5 mm, about 1-3 mm, or to any depth thereabout or therebetween.

In another embodiment, the invention provides an highly cross-linked, oxidatively stable, and highly crystalline (for example, at least about 51% crystallinity) polymeric material obtainable by any of the methods described herein.

DETAILED DESCRIPTION OF THE INVENTION

Figure 1:
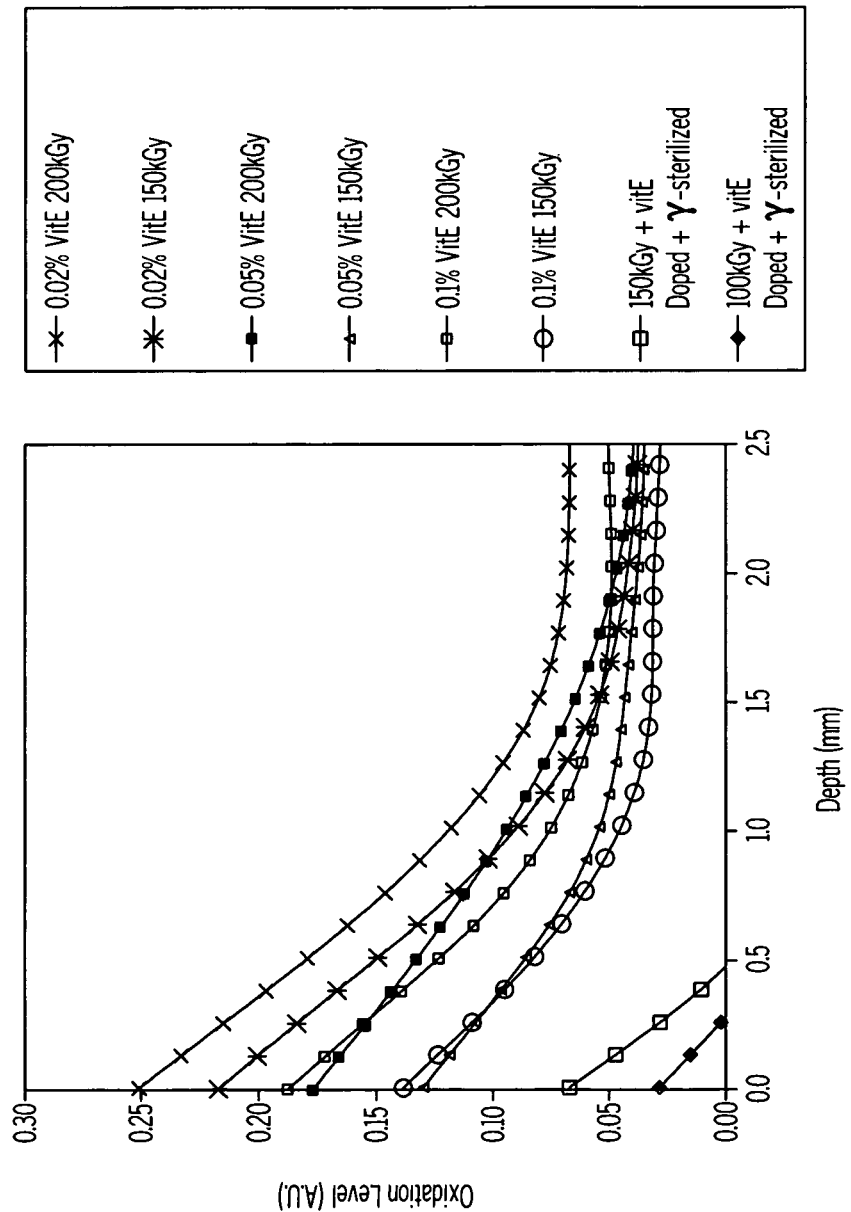
FIG. 1 shows oxidation profile as a function of depth of UHMWPE samples made from powder containing varying levels of Vitamin E. Following consolidation, samples were irradiated to differing dose levels, then aged for 10 months at 40° C. in a water tank. The controls were irradiated, then doped in Vitamin E prior to aging.

The present invention provides methods for making cross-linked oxidatively stable polymeric materials. The invention pertains to methods of heat treatment of irradiation-cross-linked antioxidant-containing polymers, cross-linked oxidation-resistant polymeric materials having oxidative stability obtainable thereby, and materials used therewith.

The present invention provides that when the irradiation is carried out at high radiation dose rates and/or high temperatures, the host polymer's cross-linking efficiency is increased, which is potentially related to the reduction in the activity of the antioxidant. This phenomenon responsible for the increase in the efficiency of cross-linking of the host polymer is related to a number of factors, although the accuracy of any mechanism does not interfere with the practice of any embodiment or aspect of the invention:

One possible mechanism is that at elevated temperatures the ability of the antioxidant to scavenge free radicals is reduced, hence the cross-linking efficiency of the host polymer is increased. Elevated temperature is either reached by externally heating the polymer blend and/or by providing radiation generated heating (including adiabatic and partially adiabatic) of the polymer by the high irradiation dose rate.

Another possible mechanism is that when the host polymer is semi-crystalline, melting of some or all of the crystalline domains provides antioxidant-free polymer, in which domains cross-linking efficiency is not compromised. This melting is induced by radiation generated heating (including adiabatic and partially adiabatic) of polymer blend during irradiation. The radiation generated heating (including adiabatic and partially adiabatic) depends on a number of processing parameters taught herein, such as dose rate, initial temperature of the sample, absorbed radiation dose, and the like. Radiation generated heating (including adiabatic and partially adiabatic) is a result of the conversion of the radiation dose to heat in the irradiated sample. Most semi-crystalline polymers exhibit a range of melting temperatures because of the large distribution in the size of the crystalline domains—small crystals melt at lower temperatures and large crystals melt at higher temperatures. For example, virgin UHMWPE typically starts melting near 90° C. and melts up to near 140° C. with a peak melting point of near 137° C. If the temperature of the sample is high enough during melting, radiation generated heating (including adiabatic and partially adiabatic) results in melting of the crystals, which continuously generates new amorphous polymer during irradiation. In most semi-crystalline polymer/antioxidant blends the antioxidant resides in the amorphous phase and cannot be accommodated in the crystalline domains. When radiation generated (including adiabatic and partially adiabatic) melting results in increasing amorphous content, the cross-linking efficiency of the polymer is effectively higher in the newly formed, antioxidant-free amorphous domains. A post-irradiation homogenization step may be necessary to diffuse the antioxidant from antioxidant-rich regions to antioxidant poor regions. Temperature immediately after (and/or during) irradiation may be high enough to automatically homogenize the antioxidant-poor regions.

Even when the initial temperature of the polymer is low, for example, near room temperature or 40° C., the radiation generated heating (including adiabatic and partially adiabatic) can be high enough to increase the temperature of the polymer during irradiation. Hence, even cold e-beam irradiated polymer experiences a temperature rise, and depending on the radiation dose level, may spend some time at higher temperatures where the antioxidant's ability to hinder cross-linking is reduced. Therefore, under certain embodiments, cold irradiation with e-beam, which allows high dose rate, is more beneficial than cold-irradiation with gamma, which practically does not allow the high dose rates needed for radiation generated heating (including adiabatic and partially adiabatic).

To achieve a target cross-link density and obtain certain properties, such as a reduction in wear rate of the polymer, the radiation dose is increased to counter the hindrance caused by the antioxidant. Because, at an elevated temperatures the hindrance caused by the antioxidant is reduced, it may be beneficial to maximize the irradiation temperature to minimize the radiation dose level needed to achieve the target cross-link density. If the initial temperature and radiation dose are too high, radiation generated heating (including adiabatic and partially adiabatic) may result in complete melting of the polymer, which reduces the crystallinity and thus mechanical properties of the polymer.

In an embodiment, the polymer blend is irradiated at a dose rate of about 1 to 1000 kGy per pass. The irradiation dose rates that can be reached with electron beam are much higher than those with gamma irradiation. Electron beam dose rate are typically on the order of 1 to several hundred kGy per pass with each pass taking anywhere between a few seconds to a few minutes. The polymer blend is brought to a certain initial temperature and irradiated. The dose rate is high enough to cause radiation generated heating (including adiabatic and partially adiabatic) of the polymer. The temperature of the sample during irradiation depends on the starting temperature and the radiation dose level used. Following equation, which assume purely radiation generated heating (including adiabatic and partially adiabatic) conditions, can be used to estimate the temperature:

$$D = \Delta H_{m,i}(T_i) + c_p \Delta T,$$ EQ 1 where D is the radiation dose level absorbed by the sample, $T_i$ is the instantaneous temperature of the sample, $\Delta T$ ($=T_i-T_o$) is the difference between the instantaneous temperature ($T_i$) of the sample and the initial temperature ($T_o$) of the sample, $\Delta H_{m,i}(T_i)$ is the melting enthalpy of the crystals that melt below the instantaneous temperature of the sample, and $c_p$ is the specific heat of the polymer. This equation assumes purely radiation generated heating (including adiabatic and partially adiabatic) conditions; while there will be some heat loss to the surroundings near the surface of the irradiated sample, the bulk of the sample will more closely follow the temperature predicted by this equation, especially at high dose rates, and thus is a practical approximation. If a certain temperature is desired during irradiation, the equation is used to determine the irradiation parameters. In this embodiment the radiation dose level can be above 1 kGy. More preferably it can be 25 kGy, 50 kGy, 100 kGy, 150 kGy, 200 kGy or above. The dose rate can be about 1, 10, 25, 75, 100, 150, 200, or more kGy per pass or any dose rate in-between. The initial temperature can be below room temperature (RT), RT, above RT, about 40, 50, 75, 100, 110, 125, 130, 135° C. or more or any temperature thereabout or therebetween. The irradiation can be carried out with e-beam, gamma, or x-rays. The latter two has lower dose rates than e-beam; therefore e-beam is more practical to reach high dose rates.

In another embodiment, the polymer blend is irradiated with gamma or e-beam followed by annealing or melting to recombine the free radicals trapped in the crystalline domains. When the irradiation is carried out at low temperatures and/or low dose rates, the cross-link density is lower than it is after the irradiated polymer blend is annealed below the melting point or melted.

In certain embodiments, it is not desired to completely melt the polymer blend during the irradiation step. For example, with a required high dose level (higher than 100 kGy) to reach a desired cross-link density, the polymer blend could be subjected to radiation generated (including adiabatic and partially adiabatic) melting and result in complete melting of the blend. Post-irradiation melting reduces the crystallinity of the sample, which in turn reduces mechanical properties of the blend. One can prevent complete melting of the blend during irradiation by keeping the dose rate low to minimize radiation generated heating (including adiabatic and partially adiabatic), reduce the initial temperature, and/or reduce the radiation dose. In certain embodiments the polymer blend may require a higher initial temperature; in such cases one can use low radiation dose rate to reduce the extent of melting by radiation generated heating.

In another embodiment, irradiation is carried out in multiple steps so as to reduce the extent of radiation generated heating (including adiabatic and partially adiabatic) of the polymer blend. For instance, the polymer blend is irradiated in multiple passes under or near the radiation source (such as e-beam, gamma, or x-rays). The time between the passes can be adjusted to allow the polymer blend to cool down to the desired irradiation temperature. In some embodiments it is desirable to heat the sample between irradiation passes.

In another embodiment, the initial temperature of the polymer sample is adjusted such that the temperature of the polymer blend is increased to its peak melting point during irradiation.

DSC testing of warm irradiated blends typically exhibit three melting peaks on their first heat and two melting peaks on their second heat. The area under the highest melting peak of the first heat can be used to determine the extent of melting in the polymer during warm irradiation.

In another embodiment, crystallinity of a blend is increased through, for example high pressure crystallization. The highly crystalline blend is then irradiated. The crystalline domains contain little or no antioxidant, as a result, the free radicals formed in the crystalline domains are viable for recombination and cross-linking reactions. To allow the recombination of the free radicals in the crystalline domains the blend is irradiated with a high enough dose rate to partially melt the polymer. Alternatively, the irradiation is carried out at an elevated temperature to partially melt the polymer. Another approach is to post-irradiation anneal or melt the polymer to allow the free radicals in the crystalline domains to recombine with each other. These approaches result in an improved cross-linking efficiency for the blend. A post-irradiation homogenization step may be necessary to diffuse the antioxidant from antioxidant-rich regions to antioxidant-poor regions.

In another embodiment, a polymer/antioxidant blend is mixed with virgin polymer flakes and consolidated. The consolidation cycle is kept as short as possible and at the lowest possible temperature to minimize bleeding of the antioxidant from the antioxidant blended flakes into virgin flakes. The consolidated polymer is then irradiated and subsequently homogenized to allow diffusion of antioxidant from antioxidant-rich regions to antioxidant-poor regions.

Alternatively, the antioxidant doped flakes could be subjected to an annealing cycle to diffuse the antioxidant to deeper into individual flakes and minimize its presence as a surface coating. This also reduces the extent of antioxidant bleeding across from the doped flakes to virgin flakes during consolidation and/or irradiation.

The invention provides various methods to improve the oxidative stability of irradiated antioxidant-containing polymers. In an embodiment, the invention provides methods to improve oxidative stability of polymers by heat treatment (such as annealing) of irradiated polymer-antioxidant blend to reduce the concentration of the residual free radicals through recombination reactions resulting in cross-linking and/or through reaction of the residual free radicals with the antioxidant. The latter is likely to take place by the abstraction of a hydrogen atom from the antioxidant molecules to the polymer, thus eliminating the residual free radical on the polymer backbone. Hence heat treatment (such as annealing) of an irradiated polymer in the presence of an antioxidant is more effective in reducing the concentration of residual free radicals than heat treatment (such as annealing) of an irradiated polymer in the absence of an antioxidant.

In another embodiment, invention provides methods to improve oxidative stability of polymers by diffusing more antioxidant into the irradiated polymer-antioxidant blend. The antioxidant diffusion methods have been described by Muratoglu et al. (see, e.g., US 2004/0156879; U.S. application Ser. No. 11/465,544, filed Aug. 18, 2006; PCT/US2006/032329 Published as WO 2007/024689, which are incorporated herein by reference).

In another embodiment, invention provides methods to improve oxidative stability of polymers by mechanically deforming the irradiated antioxidant-containing polymers to reduce or eliminate the residual free radicals. Mechanical deformation methods have been described by Muratoglu et al. (see, e.g., US 2004/0156879; US 2005/0124718; and PCT/US05/003305 published as WO 2005/074619), which are incorporated herein by reference.

The present invention also describes methods that allow reduction in the concentration of residual free radical in irradiated polymer, even to undetectable levels, without heating the material above its melting point. This method involves subjecting an irradiated sample to a mechanical deformation that is below the melting point of the polymer. The deformation temperature could be as high as about 135° C., for example, for UHMWPE. The deformation causes motion in the crystalline lattice, which permits recombination of free radicals previously trapped in the lattice through cross-linking with adjacent chains or formation of trans-vinylene unsaturations along the back-bone of the same chain. If the deformation is of sufficiently small amplitude, plastic flow can be avoided. The percent crystallinity should not be compromised as a result. Additionally, it is possible to perform the mechanical deformation on machined components without loss in mechanical tolerance. The material resulting from the present invention is a cross-linked polymeric material that has reduced concentration of residuals free radical, and preferably substantially no detectable free radicals, while not substantially compromising the crystallinity and modulus.

The present invention further describes that the deformation can be of large magnitude, for example, a compression ratio of 2 in a channel die. The deformation can provide enough plastic deformation to mobilize the residual free radicals that are trapped in the crystalline phase. It also can induce orientation in the polymer that can provide anisotropic mechanical properties, which can be useful in implant fabrication. If not desired, the polymer orientation can be removed with an additional step of heating at an increased temperature below or above the melting point.

According to another aspect of the invention, a high strain deformation can be imposed on the irradiated component. In this fashion, free radicals trapped in the crystalline domains likely can react with free radicals in adjacent crystalline planes as the planes pass by each other during the deformation-induced flow. High frequency oscillation, such as ultrasonic frequencies, can be used to cause motion in the crystalline lattice. This deformation can be performed at elevated temperatures that is below the melting point of the polymeric material, and with or without the presence of a sensitizing gas. The energy introduced by the ultrasound yields crystalline plasticity without an increase in overall temperature.

The present invention also provides methods of further heating free radical elimination below melting point of the polymeric material. According to the invention, elimination of free radicals below the melt is achieved either by the sensitizing gas methods and/or the mechanical deformation methods. Further heating of cross-linked polymer containing reduced or no detectable residual free radicals is done for various reasons, for example:

1. Mechanical deformation, if large in magnitude (for example, a compression ratio of two during channel die deformation), will induce molecular orientation, which may not be desirable for certain applications, for example, acetabular liners. Accordingly, for mechanical deformation:

a) Thermal treatment below the melting point (for example, less than about 137° C. for UHMWPE) is utilized to reduce the amount of orientation and also to reduce some of the thermal stresses that can persist following the mechanical deformation at an elevated temperature and cooling down. Following heating, it is desirable to cool down the polymer at slow enough cooling rate (for example, at about 10° C./hour) so as to minimize thermal stresses. If under a given circumstance, annealing below the melting point is not sufficient to achieve reduction in orientation and/or removal of thermal stresses, one can heat the polymeric material to above its melting point.

b) Thermal treatment above the melting point (for example, more than about 137° C. for UHMWPE) can be utilized to eliminate the crystalline matter and allow the polymeric chains to relax to a low energy, high entropy state. This relaxation leads to the reduction of orientation in the polymer and substantially reduces thermal stresses. Cooling down to room temperature is then carried out at a slow enough cooling rate (for example, at about 10° C./hour) so as to minimize thermal stresses.

2. The contact before, during, and/or after irradiation with a sensitizing environment to yield a polymeric material with no substantial reduction in its crystallinity when compared to the reduction in crystallinity that otherwise occurs following irradiation and subsequent or concurrent melting. The crystallinity of polymeric material contacted with a sensitizing environment and the crystallinity of radiation treated polymeric material is reduced by heating the polymer above the melting point (for example, more than about 137° C. for UHMWPE). Cooling down to room temperature is then carried out at a slow enough cooling rate (for example, at about 10° C./hour) so as to minimize thermal stresses.

As described herein, it is demonstrated that mechanical deformation can eliminate residual free radicals in a radiation cross-linked UHMWPE. The invention also provides that one can first deform UHMWPE to a new shape either at solid- or at molten-state, for example, by compression. According to a process of the invention, mechanical deformation of UHMWPE when conducted at a molten-state, the polymer is crystallized under load to maintain the new deformed shape. Following the deformation step, the deformed UHMWPE sample is irradiated below the melting point to cross-link, which generates residual free radicals. To eliminate these free radicals, the irradiated polymer specimen is heated to a temperature below the melting point of the deformed and irradiated polymeric material (for example, up to about 135° C. for UHMWPE) to allow for the shape memory to partially recover the original shape. Generally, it is expected to recover about 80-90% of the original shape. During this recovery, the crystals undergo motion, which can help the free radical recombination and elimination. The above process is termed as a 'reverse-IBMA'. The reverse-IBMA (reverse-irradiation below the melt and mechanical annealing) technology can be a suitable process in terms of bringing the technology to large-scale production of UHMWPE-based medical devices.

In another embodiment, invention provides methods to improve oxidative stability of polymers by blending and consolidating virgin UHMWPE resin, powder, or flake with vitamin E-containing resin, powder, or flake to form vitamin E-deficient regions. Following irradiation, the samples are annealed below the melt to both quench residual free radicals and to further diffuse the vitamin E into the previously vitamin E-deficient regions.

In another embodiment, the invention provides a highly cross-linked, oxidatively stable highly crystalline UHMWPE, made by a process comprising the steps of:
a) blending antioxidant (for example, vitamin E) with UHMWPE resin, powder, is or flake;
b) consolidating the blend;
c) irradiating the consolidated polymeric material at a temperature below the melting point; and
d) annealing the consolidated polymeric material in air or under an inert environment at a temperature below the melting temperature of the polymeric material, thereby forming a highly cross-linked, oxidatively stable, and highly crystalline polymeric material.

In another embodiment, the invention provides a highly cross-linked, oxidatively stable highly crystalline UHMWPE, made by a process comprising the steps of:
a) blending antioxidant (for example, vitamin E) with UHMWPE resin, powder, or flake;
b) consolidating the blend;
c) irradiating the consolidated polymeric material at a temperature below the melting point; and
d) annealing the consolidated polymeric material under high pressure at a temperature below the melting temperature of the polymeric material, thereby forming a highly cross-linked, oxidatively stable, and highly crystalline polymeric material.

In another embodiment, the invention provides a highly cross-linked, oxidatively stable highly crystalline UHMWPE, made by a process comprising the steps of:
a) blending antioxidant (for example, vitamin E) with UHMWPE resin, powder, or flake;
b) consolidating the blend;
c) irradiating the consolidated polymeric material at a temperature below the melting point; and
d) annealing the consolidated polymeric material in presence of a supercritical fluid at a temperature below the melting temperature of the polymeric material, thereby forming a highly cross-linked, oxidatively stable, and highly crystalline polymeric material.

In another embodiment, the invention provides a highly cross-linked, oxidatively stable highly crystalline UHMWPE, made by a process comprising the steps of:
a) blending antioxidant (for example, vitamin E) with UHMWPE resin, powder, or flake;
b) consolidating the blend;
c) irradiating the consolidated polymeric material at a temperature below the melting point; and
d) quenching the residual free radicals by mechanical deformation in air or under an inert environment at a temperature below the melting temperature of the polymeric material, thereby forming a highly cross-linked, oxidatively stable, and highly crystalline polymeric material.

In another embodiment, the invention provides a highly cross-linked, oxidatively stable highly crystalline UHMWPE, made by a process comprising the steps of:
a) blending antioxidant (for example, vitamin E) with UHMWPE resin, powder, or flake;
b) consolidating the blend;
c) irradiating the consolidated polymeric material at a temperature below the melting point;
d) quenching the residual free radicals by mechanical deformation in air or under an inert environment at a temperature below the melting temperature of the polymeric material; and
e) annealing the consolidated polymeric material in air or under an inert environment at a temperature below the melting temperature of the polymeric material, thereby forming a highly cross-linked, oxidatively stable, and highly crystalline polymeric material.

In another embodiment, the invention provides a highly cross-linked, oxidatively stable highly crystalline UHMWPE, made by a process comprising the steps of:
a) blending antioxidant (for example, vitamin E) with UHMWPE resin, powder, or flake;
b) mixing the blend with virgin UHMWPE resin, powder, or flake, thereby forming a composition having antioxidant rich and poor regions/domains;
c) consolidating the composition, thereby forming a polymeric material having antioxidant rich and poor regions/domains;

d) irradiating the consolidated polymeric material at temperature below the melting point; and e) annealing the consolidated polymeric material in air or under an inert environment at a temperature below the melting temperature of the polymeric material, thereby forming a highly cross-linked, oxidatively stable, and highly crystalline polymeric material.

In another embodiment, the invention provides a highly cross-linked, oxidatively stable highly crystalline UHMWPE, made by a process comprising the steps of:

a) blending antioxidant (for example, vitamin E) with UHMWPE resin, powder, or flake;

b) mixing the blend with virgin UHMWPE resin, powder, or flake, thereby forming a composition having antioxidant rich and poor regions/domains;

c) consolidating the composition, thereby forming a polymeric material having antioxidant rich and poor regions/domains;

d) irradiating the consolidated polymeric material at temperature below the melting point; and e) quenching the residual free radicals by mechanical deformation in air or under an inert environment at a temperature below the melting temperature of the polymeric material, thereby forming a highly cross-linked, oxidatively stable, and highly crystalline polymeric material.

In another embodiment, the invention provides a highly cross-linked, oxidatively stable polymeric blend, wherein the polymeric material and an additive such as an antioxidant (vitamin E, for example) blend is radiation cross-linked above room temperature and providing a crosslink density above about 0.13 mol/dm$^3$.

In another embodiment, the invention provides a highly cross-linked, oxidatively stable polymeric blend, wherein the polymeric material and an additive such as an antioxidant (vitamin E, for example) blend is radiation cross-linked with at least about 100 kGy dose above room temperature such that its crosslink density is above that of room temperature irradiated UHMWPE.

In another embodiment, the invention provides a highly cross-linked, oxidatively stable polymeric blend, wherein the polymeric material and an additive such as an antioxidant (vitamin E, for example) blend is radiation cross-linked above room temperature and providing at least 2 melting peaks during the first melting cycle (for example, during the first heating in DSC).

In another embodiment, the invention provides a highly cross-linked, oxidatively stable polymeric blend, wherein the polymeric material and an additive such as an antioxidant (vitamin E, for example) blend is radiation cross-linked above room temperature and providing a crystallinity of less than about 58% after one melting cycle (for example, during the second or later heating step in DSC).

In another embodiment, the invention provides a highly cross-linked, oxidatively stable polymeric blend, wherein the polymeric material and an additive such as an antioxidant (vitamin E, for example) blend is radiation cross-linked above room temperature and providing at least 2 melting peaks during the re-melting cycle (for example, during the second or later heating step in DSC).

In another embodiment, the invention provides a highly cross-linked, oxidatively stable polymeric blend, wherein the polymeric material and an additive such as an antioxidant (vitamin E, for example) blend is sequentially irradiated and annealed.

In another embodiment, the invention provides a highly cross-linked, oxidatively stable polymeric blend, wherein the polymeric material and an additive such as an antioxidant (vitamin E, for example) is radiation cross-linked such that at least some portion of the radiation dose is administered below 100° C. and the remaining radiation dose is administered above 40° C. so as to minimize warm irradiation induced fracture of the polyethylene.

The consolidated polymeric materials according to any of the methods described herein can be irradiated at room temperature or at an elevated temperature below the melting point of the polymeric material.

In certain embodiments of the present invention any of the method steps disclosed herein, including blending, mixing, consolidating, quenching, irradiating, annealing, mechanically deforming, doping, homogenizing, heating, melting, and packaging of the finished product, such as a medical implant, can be carried out in presence of a sensitizing gas and/or liquid or a mixture thereof, inert gas, air, vacuum, and/or a supercritical fluid.

The consolidated and irradiation cross-linked polymeric materials according to any of the methods described herein can be further doped with an antioxidant.

The consolidated and irradiation cross-linked polymeric materials according to any of the methods described herein can be further doped with an antioxidant and homogenized at a temperature below the melting point of the polymeric material.

In another embodiment, the invention provides a highly cross-linked, oxidatively stable highly crystalline medical device, made by any of the above methods.

In another embodiment, the invention provides a highly cross-linked, oxidatively stable highly crystalline medical device, wherein the polymeric material is machined subsequently after the consolidation, irradiation, heating and/or annealing or the quenching step.

In another embodiment, the invention provides a highly cross-linked, oxidatively stable highly crystalline medical device, wherein the crystallinity of the polymeric material is greater than about 51%.

According to an aspect of the invention, the limitations of α-tocopherol diffusion in polymeric material is overcome by shortening the diffusion path of α-tocopherol necessary after irradiation. This is achieved by creating a polymeric article that has higher α-tocopherol concentration in the bulk (generally the interior regions) and lower α-tocopherol concentration on the surface (exterior regions). When this polymeric article is irradiated, the α-tocopherol rich regions in the bulk, in which wear reduction through cross-linking is not necessary, have a lower final cross-link density than they would have in the absence or lessened presence of α-tocopherol. On the other hand, the surface contains either no α-tocopherol or lower concentrations of α-tocopherol. Therefore, the surface is cross-linked during irradiation to levels similar to material irradiated in the absence of α-tocopherol and the wear rate is reduced. Cross-linking is only needed on and near the articular surfaces to improve the wear resistance of the implant. Although the surface and the bulk of a polymeric material generally refer to exterior regions and the interior regions, respectively, there generally is no discrete boundary between these two regions. The regions are more of a gradient-like transition, can differ based upon the size and shape of the object and the resin used.

Irradiation of UHMWPE with α-tocopherol reduces the cross-linking efficiency of polymeric material and also reduces the antioxidant potency of α-tocopherol. Still, in some embodiments, there is enough α-tocopherol in the bulk such that after the irradiation step(s) there is still enough antioxidant potency to prevent oxidation in the bulk of the polymeric material. Thus, after irradiation, the polymeric article is oxidation-resistant in the bulk and is highly cross-linked on the surface. However, the surface may still contain unstabilized free radicals that can oxidize and reduce the mechanical properties of the article. To prevent oxidation on the α-tocopherol poor surface region, the irradiated article can be treated by using one or more of the following methods:

(1) doping with α-tocopherol through diffusion at an elevated temperature below the melting point of the irradiated polymeric material;

(2) mechanically deforming of the UHMWPE followed by heating below or above the melting point of the article; and/or (3) high pressure crystallization or high pressure annealing of the article;

After one or more of these treatments, the free radicals are stabilized or practically eliminated everywhere in the article.

In some embodiments none of the above mentioned four stabilization techniques are used because there is still enough antioxidant potency left in the polymeric material both at the surface and in the bulk so as not to compromise oxidation stability of the polymeric material in the long-term. For instance, the polymeric material with spatially varying antioxidant concentration is irradiated at an elevated temperature above room temperature, preferably at about 40° C., at above 40° C., at 75° C., at above 75° C., at about 100° C., at about 110° C., or at about 120° C.

Another advantage of this approach where cross-linking is constrained to a thin surface layer is that the overall bulk mechanical properties of the polymeric article are not altered compared to unirradiated UHMWPE as they would be if the cross-links were uniformly distributed throughout the entire article.

Another added benefit of this invention is that the α-tocopherol doping can be carried out at elevated temperatures to shorten the diffusion time.

All of the embodiments are described with α-tocopherol as the antioxidant but any other antioxidant or mixtures of antioxidants also can be used.

According to one embodiment, the polymeric material is an article having a shape of an implant, a preform that can be machined to an implant shape, or any other shape.

In one embodiment, the polymeric article is prepared with α-tocopherol-rich and α-tocopherol-poor regions where the α-tocopherol-poor regions are located at one or more of the surface (exterior regions) and the α-tocopherol-rich regions are in the bulk (generally the interior regions).

An advantage of starting with α-tocopherol-rich and α-tocopherol-poor regions in the polymeric article is that the radiation cross-linking is primarily be limited to the α-tocopherol poor regions (in most embodiments the articular surfaces) and therefore the reduction in the mechanical properties of the implant due to cross-linking is minimized.

In another embodiment, the consolidated polymeric material is fabricated through direct compression molding (DCM). The DCM mold is filled with a combination of polyethylene resin, powder, or flake containing α-tocopherol and with virgin polyethylene resin, powder, or flake, that is without α-tocopherol. The mold is then heated and pressurized to complete the DCM process. The consolidated polymeric material thus formed consists of α-tocopherol rich and α-tocopherol poor regions. The concentration of α-tocopherol in the initial α-tocopherol-containing resin, powder, or flake may be sufficiently high to retain its antioxidant efficiency throughout the DCM process, and any subsequent irradiation and cleaning steps. This concentration is between about 0.0005 wt % and about 20 wt % or higher, preferably between about 0.005 wt % and about 5.0 wt %, preferably about 0.3 wt %, or preferably about 0.5 wt %. The DCM mold is filled with either or both of the resins, powders, or flakes to tailor the spatial distribution of the α-tocopherol rich and poor regions in the consolidated polymeric article. One issue is the diffusion of α-tocopherol from the blended resin, powder, or flake regions to the virgin resin, powder, or flake regions, especially during consolidation where high temperatures and durations are typical. Any such diffusion would reduce the efficiency of subsequent cross-linking in the affected virgin resin, powder, or flake regions. One can control the diffusion process by tailoring the spatial distribution of the α-tocopherol rich and α-tocopherol poor regions, by optimizing the content of α-tocopherol in the blended regions, by reducing the temperature of consolidation, and/or reducing the time of consolidation.

In some embodiments the α-tocopherol rich region is confined to the core of the polymeric article and the virgin polymeric material is confined to the outer shell whereby the thickness of the α-tocopherol-poor region is between about 0.01 mm and 20 mm, more preferably between about 1 mm and 5 mm, or more preferably about 3 mm.

In some embodiments the outer layer is limited to only one or more faces of the polymeric article. For example a polymeric article is made through DCM process by compression molding two layers of polyethylene resin, powder, or flake, one containing 0.3 or 0.5 wt % α-tocopherol and one virgin with no α-tocopherol. The order in which the two resins, powders, or flakes are placed into the mold determines which faces of the polymeric article are α-tocopherol poor and the thickness of the α-tocopherol-poor region is determined by the amount of virgin resin, powder, or flake used. This polymeric article is subsequently irradiated, doped with α-tocopherol, homogenized, machined on one or more of the faces to shape a polymeric implant, packaged and sterilized.

In some embodiments, the α-tocopherol-rich region is molded from a blend of α-tocopherol-containing resin, powder, or flake and virgin polyethylene resin, powder, or flake.

In some embodiments, the resin, powder, or flake containing α-tocopherol and the virgin polyethylene resin, powder, or flake are dry-mixed prior to molding, thereby creating a distribution of α-tocopherol-rich and α-tocopherol-poor regions throughout the polymeric article.

In some embodiments, the virgin polymeric region is confined to the articular bearing surface of the implant.

In some embodiments, the resin, powder, or flake containing α-tocopherol undergoes partial or complete consolidation prior to the DCM process. This preformed piece of α-tocopherol-containing polymeric material allows more precise control over the spatial distribution of α-tocopherol in the finished part. For example, the partially or completely consolidated resin, powder, or flake is placed in a mold surrounded by virgin resin, powder, or flake and further consolidated, creating a polymeric article with an α-tocopherol-poor region on the outer shell and α-tocopherol-rich region in the bulk of the polymeric article.

In another embodiment a polymeric component is fabricated through DCM as described above with spatially-controlled α-tocopherol-rich and α-tocopherol-poor regions. This component is subsequently treated by e-beam irradiation. E-beam irradiation is known to have a gradient cross-linking effect in the direction of the irradiation, but this is not always optimized in components which have curved surfaces, such as acetabular cups, where the cross-linking is different at different points on the articulating surface. The spatial distribution of α-tocopherol-rich regions is used in conjunction with e-beam irradiation to create uniform surface cross-linking which gradually decreases to minimal cross-linking in the bulk. After irradiation, the polymeric component is doped with α-tocopherol. This component is cross-linked and stabilized at the surface and transitions to the uncross-linked and stabilized material with increasing depth from the surface.

In some embodiments the vitamin-E/polymeric material blended resin, powder, or flake mixture has a very high vitamin-E concentration such that when this resin, powder, or flake mixture is consolidated with neat resin, powder, or flake there is a steep gradient of vitamin-E across the interface. The consolidated piece is then irradiated to cross-link the polymer preferably in the neat α-tocopherol-poor region. Subsequently, the piece is heated to drive diffusion of α-tocopherol from the α-tocopherol-rich bulk region to the α-tocopherol-poor surface region.

In some embodiments, a vitamin-E-polymeric material (for example, UHMWPE) blend and virgin polymeric resin, powder, or flake are molded together to create an interface. The quantities of the blend and/or the virgin resins are tailored to obtain a desired virgin polymeric material thickness. Alternatively, the molded piece/material is machined to obtain the desired thickness of the virgin polymeric layer. The machined-molded piece/material is irradiated followed by:

Either doping with vitamin E and homogenized below the melting point of the polymeric material,
or heated below the melt without doping to eliminate the free radicals (for example, for different durations),
or heated below the melt for long enough duration, to diffuse the bulk vitamin E from the blend layer into the virgin layer (for example, for different durations, different blend compositions are used to accelerate the diffusion from the blend region to the virgin region),
or high pressure crystallized/annealed, thereby forming a medical device. The medical device can be used at this stage or can be machined further to remove any oxidized surface layers to obtain a net shaped implant. The device/implant also can be packaged and sterilized.

In another embodiment, the antioxidant-doped or -blended polymeric material is homogenized at a temperature below the melting point of the polymeric material for a desired period of time, for example, the antioxidant-doped or -blended polymeric material is homogenized for about an hour to several days to one week or more than one week at room temperature to about 135° C. to 137° C. (for example for UHMWPE). Preferably, the homogenization is carried out above room temperature, preferably at about 90° C. to about 135° C., more preferably about 80° C. to about 100° C., more preferably about 120° C. to about 125° C., most preferably about 130° C.

A purpose of homogenization is to make the concentration profile of α-tocopherol throughout the interior of a consolidated polymeric material more spatially uniform. After doping of the polymeric material is completed, the consolidated polymeric material is removed from the bath of α-tocopherol and wiped thoroughly to remove excess α-tocopherol from the surfaces of the polymeric material. The polymeric material is kept in an inert atmosphere (nitrogen, argon, and/or the like) or in air during the homogenization process. The homogenization also can be performed in a chamber with supercritical fluids, such as carbon dioxide or the like.

In another embodiment, the DCM process is conducted with a metal piece that becomes an integral part of the consolidated polymeric article. For example, a combination of α-tocopherol-containing polyethylene resin, powder, or flake and virgin polyethylene resin, powder, or flake is direct compression molded into a metallic acetabular cup or a tibial base plate with a spatially controlled distribution of α-tocopherol-rich and α-tocopherol-poor regions so that cross-linking of the polymeric material during the subsequent irradiation step is not hindered at the articular surfaces. For example, the porous tibial metal base plate is placed in the mold, α-tocopherol blended polymeric resin, powder, or flake is added on top and then virgin polymeric resin, powder, or flake is added last. Following consolidation the article is α-tocopherol-rich near the metal piece and also in the bulk but the articular surface is α-tocopherol-poor, which allows cross-linking of the surface layer during subsequent irradiation. Doping of the article with α-tocopherol is carried out after irradiation to stabilize the free radicals near the articular surface. Prior to the DCM consolidation, the pores of the metal piece can be filled with a waxy or plaster substance through half the thickness to achieve polyethylene interlocking through the other unfilled half of the metallic piece. The pore filler is maintained through the irradiation and subsequent α-tocopherol doping steps to prevent infusion of α-tocopherol in to the pores of the metal. In some embodiments, the article is machined after doping to shape an implant.

In another embodiment, there are more than one metal pieces integral to the polymeric article.

In another embodiment, one or some or all of the metal pieces integral to the polymeric article is a porous metal piece that allows bone in-growth when implanted into the human body.

In some embodiments, one or some or all of the metal pieces integral to the polymeric article is a non-porous metal piece.

In one embodiment, the consolidated polymeric article is irradiated using ionizing radiation such as gamma, electron-beam, or x-ray to a dose level between about 1 and about 10,000 kGy, preferably about 25 to about 250 kGy, preferably about 50 to about 150 kGy, preferably about 65 kGy, preferably about 85 kGy, or preferably about 100 kGy.

In another embodiment, the irradiated polymeric article is doped with α-tocopherol by placing the article in an α-tocopherol bath at room temperature or at an elevated temperature for a given amount of time.

In another embodiment, the doped polymeric article is heated below the melting point of the polymeric article.

In one embodiment, the metal mesh of the implant is sealed using a sealant to prevent or reduce the infusion of α-tocopherol into the pores of the mesh during the selective doping of the implant. Preferably, the sealant is water soluble. But other sealants are also used. The final cleaning step that the implant is subjected to also removes the sealant. Alternatively, an additional sealant removal step is used. Such sealants as water, saline, aqueous solutions of water soluble polymers such as poly-vinyl alcohol, water soluble waxes, plaster of Paris, or others are used. In addition, a photoresist like SU-8, or other, may be cured within the pores of the porous metal component. Following processing, the sealant may be removed via an acid etch or a plasma etch.

In another embodiment, the polyethylene-porous metal mono-block is doped so that the polymeric material is fully immersed in α-tocopherol but the porous metal is either completely above the α-tocopherol surface or only partially immersed during doping. This reduces infusion of α-tocopherol into the pores of the metal mesh.

In yet another embodiment, the doped polymeric article is machined to form a medical implant. In some embodiments, the machining is carried out on sides with no metallic piece if at least one is present.

In many embodiments, the medical devices are packaged and sterilized.

In another aspect of the invention, the medical device is cleaned before packaging and sterilization.

In other embodiments, the antioxidant, such as vitamin E, concentration profiles in implant components can be controlled in several different ways, following various processing steps and in different orders, for example:

I. Blending the antioxidant and polyethylene resin, powder, or flakes, consolidating the blend, machining of implants, radiation cross-linking (at a temperature below the melting point of the polymeric material), and doping with the antioxidant;

II. Blending the antioxidant and polyethylene resin, powder, or flakes, consolidating the blend, machining of implants, radiation cross-linking (at a temperature below the melting point of the polymeric material), doping with the antioxidant and homogenizing;

III. Blending the antioxidant and polyethylene resin, powder, or flakes, consolidating the blend, machining of implants, radiation cross-linking (at a temperature below the melting point of the polymeric material), doping with the antioxidant and homogenizing, extracting/eluting out the excess antioxidant or at least a portion of the antioxidant;

IV. Blending the antioxidant and polyethylene resin, powder, or flakes, consolidating the blend, machining of preforms, radiation cross-linking (at a temperature below the melting point of the polymeric material), doping with the antioxidant, machining of implants;

V. Blending the antioxidant and polyethylene resin, powder, or flakes, consolidating the blend, machining of preforms, radiation cross-linking (at a temperature below the melting point of the polymeric material), doping with the antioxidant and homogenizing, machining of implants;

VI. Blending the antioxidant and polyethylene resin, powder, or flakes, consolidating the blend, machining of preforms, radiation cross-linking (at a temperature below the melting point of the polymeric material), doping with the antioxidant and homogenizing, machining of implants, extraction of the antioxidant;

VII. Radiation cross-linking of consolidated polymeric material (at a temperature below the melting point of the polymeric material), machining implant, doping with the antioxidant, extracting/eluting out the excess antioxidant or at least a portion of the antioxidant;

VIII. Radiation cross-linking of consolidated polymeric material (at a temperature below the melting point of the polymeric material), machining implants, doping with the antioxidant and homogenizing, extracting/eluting out the excess antioxidant or at least a portion of the antioxidant;

IX. Radiation cross-linking of consolidated polymeric material (at a temperature below the melting point of the polymeric material), machining preforms, doping with the antioxidant, extraction of the antioxidant, machining of implants;

X. Radiation cross-linking of consolidated polymeric material (at a temperature below the melting point of the polymeric material), machining preforms, doping with the antioxidant and homogenizing, extracting/eluting out the excess antioxidant or at least a portion of the antioxidant, machining of implants;

XI. Radiation cross-linking of consolidated polymeric material (at a temperature below the melting point of the polymeric material), machining preforms, doping with the antioxidant, machining of implants, extracting/eluting out the excess antioxidant or at least a portion of the antioxidant; and/or XII. Radiation cross-linking of consolidated polymeric material (at a temperature below the melting point of the polymeric material), machining preforms, doping with the antioxidant and homogenizing, machining of implants, homogenizing, extracting/eluting out the excess antioxidant or at least a portion of the antioxidant.

In another embodiment, all of the above processes are further followed by cleaning, packaging and sterilization (gamma irradiation, e-beam irradiation, ethylene oxide or gas plasma sterilization).

Methods and Sequence of Irradiation:

The selective, controlled manipulation of polymers and polymer alloys using radiation chemistry can, in another aspect, be achieved by the selection of the method by which the polymer is irradiated. The particular method of irradiation employed, either alone or in combination with other aspects of the invention, such as the polymer or polymer alloy chosen, contribute to the overall properties of the irradiated polymer.

Gamma irradiation or electron radiation may be used. In general, gamma irradiation results in a higher radiation penetration depth than electron irradiation. Gamma irradiation, however, generally provides low radiation dose rate and requires a longer duration of time, which can result in more in-depth and extensive oxidation, particularly if the gamma irradiation is carried out in air. Oxidation can be reduced or prevented by carrying out the gamma irradiation in an inert gas, such as nitrogen, argon, neon, or helium, or under vacuum. Electron irradiation, in general, results in more limited dose penetration depth, but requires less time and, therefore, reduces the risk of extensive oxidation if the irradiation is carried out in air. In addition if the desired dose levels are high, for instance 20 Mrad, the irradiation with gamma may take place over one day, leading to impractical production times. On the other hand, the dose rate of the electron beam can be adjusted by varying the irradiation parameters, such as conveyor speed, scan width, and/or beam power. With the appropriate parameters, a 20 Mrad melt-irradiation can be completed in for instance less than 10 minutes. The penetration of the electron beam depends on the beam energy measured by million electron-volts (MeV). Most polymers exhibit a density of about 1 g/cm$^3$, which leads to the penetration of about 1 cm with a beam energy of 2-3 MeV and about 4 cm with a beam energy of 10 MeV. If electron irradiation is preferred, the desired depth of penetration can be adjusted based on the beam energy. Accordingly, gamma irradiation or electron irradiation may be used based upon the depth of penetration preferred, time limitations and tolerable oxidation levels.

According to certain embodiments, the cross-linked polymeric material can have a melt history, meaning that the polymeric material is melted concurrently with or subsequent to irradiation for cross-linking. According to other embodiments, the cross-linked polymeric material has no such melt history.

Various irradiation methods including IMS, CIR, CISM, WIR, and WIAM are defined and described in greater detail below for cross-linked polymeric materials with a melt history, that is irradiated with concurrent or subsequent melting:

(i) Irradiation in the Molten State (IMS):

Melt-irradiation (MIR), or irradiation in the molten state ("IMS"), is described in detail in U.S. Pat. No. 5,879,400. In the IMS process, the polymer to be irradiated is heated to at or above its melting point. Then, the polymer is irradiated. Following irradiation, the polymer is cooled.

Prior to irradiation, the polymer is heated to at or above its melting temperature and maintained at this temperature for a time sufficient to allow the polymer chains to achieve an entangled state. A sufficient time period may range, for example, from about 5 minutes to about 3 hours.

Gamma irradiation or electron radiation may be used. In general, gamma irradiation results in a higher radiation penetration depth than electron irradiation. Gamma irradiation, however, generally provides low radiation dose rate and requires a longer duration of time, which can result in more in-depth oxidation, particularly if the gamma irradiation is carried out in air. Oxidation can be reduced or prevented by carrying out the gamma irradiation in an inert gas, such as nitrogen, argon, neon, or helium, or under vacuum. Electron irradiation, in general, results in more limited dose penetration depth, but requires less time and, therefore, reduces the risk of extensive oxidation if the irradiation is carried out in air. In addition if the desired dose levels are high, for instance 20 Mrad, the irradiation with gamma may take place over one day, leading to impractical production times. On the other hand, the dose rate of the electron beam can be adjusted by varying the irradiation parameters, such as conveyor speed, scan width, and/or beam power. With the appropriate parameters, a 20 Mrad melt-irradiation can be completed in for instance in less than 10 minutes. The penetration of the electron beam depends on the beam energy measured by million electron-volts (MeV). Most polymers exhibit a density of about 1 g/cm$^3$, which leads to the penetration of about 1 cm with a beam energy of 2-3 MeV and about 4 cm with a beam energy of 10 MeV. The penetration of e-beam is known to increase slightly with increased irradiation temperatures. If electron irradiation is preferred, the desired depth of penetration can be adjusted based on the beam energy. Accordingly, gamma irradiation or electron irradiation may be used based upon the depth of penetration preferred, time limitations and tolerable oxidation levels.

The temperature of melt-irradiation for a given polymer depends on the DSC (measured at a heating rate of 10° C./min during the first heating cycle) peak melting temperature ("PMT") for that polymer. In general, the irradiation temperature in the IMS process is at least about 2° C. higher than the PMT, more preferably between about 2° C. and about 20° C. higher than the PMT, and most preferably between about 5° C. and about 10° C. higher than the PMT.

Exemplary ranges of acceptable total dosages are disclosed in greater detail in U.S. Pat. Nos. 5,879,400, and 6,641,617, and International Application WO 97/29793. For example, preferably a total dose of about or greater than 1 MRad is used. More preferably, a total dose of greater than about 20 Mrad is used.

In electron beam IMS, some energy deposited by the electrons is converted to heat. This primarily depends on how well the sample is thermally insulated during the irradiation. With good thermal insulation, most of the heat generated is not lost to the surroundings and leads to the radiation generated heating (including adiabatic and partially adiabatic) of the polymer to a higher temperature than the irradiation temperature. The heating could also be induced by using a high enough dose rate to minimize the heat loss to the surroundings. In some circumstance, heating may be detrimental to the sample that is being irradiated. Gaseous by-products, such as hydrogen gas when the polymer is irradiated, are formed during the irradiation. During irradiation, if the heating is rapid and high enough to cause rapid expansion of the gaseous by-products, and thereby not allowing them to diffuse out of the polymer, the polymer may cavitate. The cavitation is not desirable in that it leads to the formation of defects (such as air pockets, cracks) in the structure that could in turn adversely affect the mechanical properties of the polymer and in vivo performance of the device made thereof.

The temperature rise depends on the dose level, level of insulation, and/or dose rate. The dose level used in the irradiation stage is determined based on the desired properties. In general, the thermal insulation is used to avoid cooling of the polymer and maintaining the temperature of the polymer at the desired irradiation temperature. Therefore, the temperature rise can be controlled by determining an upper dose rate for the irradiation.

In embodiments of the present invention in which electron radiation is utilized, the energy of the electrons can be varied to alter the depth of penetration of the electrons, thereby controlling the degree of cross-linking following irradiation. The range of suitable electron energies is disclosed in greater detail in U.S. Pat. Nos. 5,879,400, 6,641,617, and International Application WO 97/29793. In one embodiment, the energy is about 0.5 MeV to about 12 MeV. In another embodiment the energy is about 1 MeV to 10 MeV. In another embodiment, the energy is about 10 MeV.

(ii) Cold Irradiation (CIR):

Cold irradiation is described in detail in U.S. Pat. Nos. 6,641,617, 6,852,772, and WO 97/29793. In the cold irradiation process, a polymer is provided at room temperature or below room temperature. Preferably, the temperature of the polymer is about 20° C. Then, the polymer is irradiated. In one embodiment of cold irradiation, the polymer may be irradiated at a high enough total dose and/or at a fast enough dose rate to generate enough heat in the polymer to result in at least a partial melting of the crystals of the polymer.

Gamma irradiation or electron radiation may be used. In general, gamma irradiation results in a higher dose penetration depth than electron irradiation. Gamma irradiation, however, generally requires a longer duration of time, which can result in more in-depth oxidation, particularly if the gamma irradiation is carried out in air. Oxidation can be reduced or prevented by carrying out the gamma irradiation in an inert gas, such as nitrogen, argon, neon, or helium, or under vacuum. Electron irradiation, in general, results in more limited dose penetration depths, but requires less time and, therefore, reduces the risk of extensive oxidation. Accordingly, gamma irradiation or electron irradiation may be used based upon the depth of penetration preferred, time limitations and tolerable oxidation levels.

The total dose of irradiation may be selected as a parameter in controlling the properties of the irradiated polymer. In particular, the dose of irradiation can be varied to control the degree of cross-linking in the irradiated polymer. The preferred dose level depends on the molecular weight of the polymer and the desired properties that can be achieved following irradiation. In general, increasing the dose level with CIR leads to an increase in wear resistance.

Exemplary ranges of acceptable total dosages are disclosed in greater detail in U.S. Pat. Nos. 6,641,617 and 6,852,772, International Application WO 97/29793, and in the embodiments below. In one embodiment, the total dose is about 0.5 MRad to about 1,000 Mrad. In another embodiment, the total dose is about 1 MRad to about 100 MRad. In yet another embodiment, the total dose is about 4 MRad to about 30 MRad. In still other embodiments, the total dose is about 20 MRad or about 15 MRad.

If electron radiation is utilized, the energy of the electrons also is a parameter that can be varied to tailor the properties of the irradiated polymer. In particular, differing electron energies results in different depths of penetration of the electrons into the polymer. The practical electron energies range from about 0.1 MeV to 16 MeV giving approximate iso-dose penetration levels of 0.5 mm to 8 cm, respectively. A preferred electron energy for maximum penetration is about 10 MeV, which is commercially available through vendors such as Studer (Daniken, Switzerland) or E-Beam Services (New Jersey, USA). The lower electron energies may be preferred for embodiments where a surface layer of the polymer is preferentially cross-linked with gradient in cross-link density as a function of distance away from the surface.

(iii) Warm Irradiation (WIR):

Warm irradiation is described in detail in U.S. Pat. No. 6,641,617 and WO 97/29793. In the warm irradiation process, a polymer is provided at a temperature above room temperature and below the melting temperature of the polymer. Then, the polymer is irradiated. In one embodiment of warm irradiation, which has been termed "warm irradiation adiabatic melting" or "WIAM." In a theoretical sense, adiabatic means an absence of heat transfer to the surroundings. In a practical sense, such heating can be achieved by the combination of insulation, irradiation dose rates and irradiation time periods, as disclosed herein and in the documents cited herein. However, there are situations where irradiation causes heating, but there is still a loss of energy to the surroundings. Also, not all warm irradiation refers to an adiabatic. Warm irradiation also can have non-adiabatic or partially (such as about 10-75% of the heat generated is lost to the surroundings) adiabatic heating. In all embodiments of WIR, the polymer may be irradiated at a high enough total dose and/or a high enough dose rate to generate enough heat in the polymer to result in at least a partial melting of the crystals of the polymer, meaning some but not all molecules transition from the crystalline to the amorphous state.

The polymer may be provided at any temperature below its melting point but preferably above room temperature. The temperature selection depends on the specific heat and the enthalpy of melting of the polymer and the total dose level used. The equation provided in U.S. Pat. No. 6,641,617 and International Application WO 97/29793 may be used to calculate the preferred temperature range with the criterion that the final temperature of polymer maybe below or above the melting point. Preheating of the polymer to the desired temperature may be done in an inert (such as under nitrogen, argon, neon, or helium, or the like, or a combination thereof) or non-inert environment (such as air).

In general terms, the pre-irradiation heating temperature of the polymer can be adjusted based on the peak melting temperature (PMT) measure on the DSC at a heating rate of 10° C./min during the first heat. In one embodiment the polymer is heated to about 20° C. to about PMT. In another embodiment, the polymer is pre-heated to about 90° C. In another embodiment, the polymer is heated to about 100° C. In another embodiment, the polymer is pre-heated to about 30° C. below PMT and 2° C. below PMT. In another embodiment, the polymer is pre-heated to about 12° C. below PMT.

In the WIAM embodiment of WIR, the temperature of the polymer following irradiation is at or above the melting temperature of the polymer. Exemplary ranges of acceptable temperatures following irradiation are disclosed in greater detail in U.S. Pat. No. 6,641,617 and International Application WO 97/29793. In one embodiment, the temperature following irradiation is about room temperature to PMT, or about 40° C. to PMT, or about 100° C. to PMT, or about 110° C. to PMT, or about 120° C. to PMT, or about PMT to about 200° C. These temperature ranges depend on the polymer's PMT and is much higher with reduced level of hydration. In another embodiment, the temperature following irradiation is about 145° C. to about 190° C. In yet another embodiment, the temperature following irradiation is about 145° C. to about 190° C. In still another embodiment, the temperature following irradiation is about 150° C.

In WIR, gamma irradiation or electron radiation may be used. In general, gamma irradiation results in a higher dose penetration depth than electron irradiation. Gamma irradiation, however, generally requires a longer duration of time, which can result in more in-depth oxidation, particularly if the gamma irradiation is carried out in air. Oxidation can be reduced or prevented by carrying out the gamma irradiation in an inert gas, such as nitrogen, argon, neon, or helium, or under vacuum. Electron irradiation, in general, results in more limited dose penetration depths, but requires less time and, therefore, reduces the risk of extensive oxidation. Accordingly, gamma irradiation or electron irradiation may be used based upon the depth of penetration preferred, time limitations and tolerable oxidation levels. In the WIAM embodiment of WIR, electron radiation is used.

The total dose of irradiation may also be selected as a parameter in controlling the properties of the irradiated polymer. In particular, the dose of irradiation can be varied to control the degree of cross-linking in the irradiated polymer. Exemplary ranges of acceptable total dosages are disclosed in greater detail in U.S. Pat. No. 6,641,617 and International Application WO 97/29793.

The dose rate of irradiation also may be varied to achieve a desired result. The dose rate is a prominent variable in the WIAM process. The preferred dose rate of irradiation would be to administer the total desired dose level in one pass under the electron-beam. One also can deliver the total dose level with multiple passes under the beam, delivering a (equal or unequal) portion of the total dose at each time. This would lead to a lower effective dose rate.

Ranges of acceptable dose rates are exemplified in greater detail in U.S. Pat. No. 6,641,617 and International Application WO 97/29793. In general, the dose rates vary between 0.5 Mrad/pass and 50 Mrad/pass. The upper limit of the dose rate depends on the resistance of the polymer to cavitation/cracking induced by the irradiation.

If electron radiation is utilized, the energy of the electrons also is a parameter that can be varied to tailor the properties of the irradiated polymer. In particular, differing electron energies result in different depths of penetration of the electrons into the polymer. The practical electron energies range from about 0.1 MeV to 16 MeV giving approximate iso-dose penetration levels of 0.5 mm to 8 cm, respectively. The preferred electron energy for maximum penetration is about 10 MeV, which is commercially available through vendors such as Studer (Daniken, Switzerland) or E-Beam Services New Jersey, USA). The lower electron energies may be preferred for embodiments where a surface layer of the polymer is preferentially cross-linked with gradient in cross-link density as a function of distance away from the surface.

(iv) Subsequent Melting (SM)—Substantial Elimination of Detectable Residual Free Radicals:

Depending on the polymer or polymer alloy used, and whether the polymer was irradiated below its melting point, there may be residual free radicals left in the material following the irradiation process. A polymer irradiated below its melting point with ionizing radiation contains cross-links as well as long-lived trapped free radicals. Some of the free radicals generated during irradiation become trapped in the crystalline regions and/or at crystalline lamellae surfaces leading to oxidation-induced instabilities in the long-term (see Kashiwabara, H. S. Shimada, and Y. Hori, *Radiat. Phys. Chem.*, 1991, 37(1): p. 43-46; Jahan, M. S, and C. Wang, *Journal of Biomedical Materials Research*, 1991, 25: p. 1005-1017; Sutula, L. C., et al., *Clinical Orthopedic Related Research*, 1995, 3129: p. 1681-1689.). The elimination of these residual, trapped free radicals through heating can be, therefore, desirable in precluding long-term oxidative instability of the polymer. Jahan M. S, and C. Wang, *Journal of Biomedical Materials Research*, 1991, 25: p. 1005-1017; Sutula, L. C., et al., *Clinical Orthopedic Related Research*, 1995, 319: p. 28-4.

Residual free radicals may be reduced by heating the polymer above the melting point of the polymer used. The heating allows the residual free radicals to recombine with each other. If for a given system the preform does not have substantially any detectable residual free radicals following irradiation, then a later heating step may be omitted. Also, if for a given system the concentration of the residual free radicals is low enough to not lead to degradation of device performance, the heating step may be omitted.

The reduction of free radicals to the point where there are substantially no detectable free radicals can be achieved by heating the polymer to above the melting point. The heating provides the molecules with sufficient mobility so as to eliminate the constraints derived from the crystals of the polymer, thereby allowing essentially all of the residual free radicals to recombine. Preferably, the polymer is heated to a temperature between the peak melting temperature (PMT) and degradation temperature ($T_d$) of the polymer, more preferably between about 3° C. above PMT and $T_d$, more preferably between about 10° C. above PMT and 50° C. above PMT, more preferably between about 10° C. and 12° C. above PMT and most preferably about 15° C. above PMT.

In certain embodiments, there may be an acceptable level of residual free radicals in which case, the post-irradiation annealing also can be carried out below the melting point of the polymer, the effects of such free radicals can be minimized or eliminated by an antioxidant.

(v) Sequential Irradiation:

The polymer is irradiated with either gamma or e-beam radiation in a sequential manner. With e-beam the irradiation is carried out with multiple passes under the beam and with gamma radiation the irradiation is carried out in multiple passes through the gamma source. Optionally, the polymer is thermally treated in between each or some of the irradiation passes. The thermal treatment can be heating below the melting point or at the melting point of the polymer. The irradiation at any of the steps can be warm irradiation, cold irradiation, or melt irradiation, or any combination thereof. For example the polymer is irradiated with 30 kGy at each step of the cross-linking and it is first heated to about 120° C. and then annealed at about 120° C. for about 5 hours after each irradiation cycle.

(vi) Blending and Doping:

As stated above, the cross-liked polymeric material can optionally have a melt history, meaning it is melted concurrent with or subsequent to irradiation. The polymeric material can be blended with an antioxidant prior to consolidation and irradiation. Also, the consolidated polymeric material can be doped with an antioxidant prior to or after irradiation, and optionally can have been melted concurrent with or subsequent to irradiation. Furthermore, a polymeric material can both be blended with an antioxidant prior to consolidation and doped with an antioxidant after consolidation (before or after irradiation and optional melting). The polymeric material can be subjected to extraction at different times during the process, and can be extracted multiple times as well.

The polymeric material can be blended with any of the antioxidants, including alpha-ocopherol (such as vitamin E), delta-tocopherol; propyl, octyl, or dedocyl gallates; lactic, citric, ascorbic, tartaric acids, and organic acids, and their salts; orthophosphates; tocopherol acetate; lycopene; or a combination thereof.

Definitions and other Embodiments

"Antioxidant" refers to what is known in the art as (see, for example, WO 01/80778, U.S. Pat. No. 6,448,315). Alpha- and delta-tocopherol; propyl, octyl, or dedocyl gallates; lactic, citric, ascorbic, tartaric acids, and organic acids, and their salts; orthophosphates, lycopene, tocopherol acetate. Vitamin E is a preferred antioxidant.

"High-pressure crystallization" refers to a method of making high pressure crystallized polyethylene, according to the invention, as described herein.

"High-pressure annealing" refers to a method of making high pressure crystallized polyethylene, according to the invention, as described herein.

The phrase "spatially controlled antioxidant distribution" refers to distribution of antioxidant in a controlled manner, such as a desired amount of an antioxidant or a mixture of antioxidants is(are) diffused in or blended in a polymeric material, in order to have a gradient of antioxidant distribution. A spatial distribution of the antioxidant allows formation of regions within a polymeric material having some regions rich and other regions poor in antioxidant content, which also can be termed as a medical implant or preform containing the spatially controlled antioxidant distribution.

"Supercritical fluid" refers to what is known in the art, for example, supercritical propane, acetylene, carbon dioxide ($CO_2$). In this connection the critical temperature is that temperature above which a gas cannot be liquefied by pressure alone. The pressure under which a substance may exist as a gas in equilibrium with the liquid at the critical temperature is the critical pressure. Supercritical fluid condition generally means that the fluid is subjected to such a temperature and such a pressure that a supercritical fluid and thereby a supercritical fluid mixture is obtained, the temperature being above the supercritical temperature, which for $CO_2$ is 31.3° C., and the pressure being above the supercritical pressure, which for $CO_2$ is 73.8 bar. More specifically, supercritical condition refers to a condition of a mixture, for example, UHMWPE with an antioxidant, at an elevated temperature and pressure, when a supercritical fluid mixture is formed; and then evaporate $CO_2$ from the mixture, UHMWPE doped with an antioxidant is obtained (see, for example, U.S. Pat. No. 6,448,315 and WO 02/26464)

The term "compression molding" as referred herein related generally to what is known in the art and specifically relates to high temperature molding polymeric material wherein polymeric material is in any physical state, including resin, powder, or flake form, is compressed into a slab form or mold of a medical implant, for example, a tibial insert, an acetabular liner, a glenoid liner, a patella, or an unicompartmental insert, an interpositional device for any joint can be machined.

The term "direct compression molding" (DCM) as referred herein related generally to what is known in the art and specifically relates to molding applicable in polyethylene-based devices, for example, medical implants wherein polyethylene in any physical state, including resin, powder, or flake form, is compressed to solid support, for example, a metallic back, metallic mesh, or metal surface containing grooves, undercuts, or cutouts. The compression molding also includes high temperature compression molding of polyethylene at various states, including resin, powder, flakes and particles, to make a component of a medical implant, for example, a tibial insert, an acetabular liner, a glenoid liner, a patella, an interpositional device for any joint or an unicompartmental insert.

The term "Mechanical deformation" refers to a deformation taking place below the melting point of the material, essentially 'cold-working' the material. The deformation modes include uniaxial, channel flow, uniaxial compression, biaxial compression, oscillatory compression, tension, uniaxial tension, biaxial tension, ultra-sonic oscillation, bending, plane stress compression (channel die), torsion or a combination of any of the above. The deformation could be static or dynamic. The dynamic deformation can be a combination of the deformation modes in small or large amplitude oscillatory fashion. Ultrasonic frequencies can be used. All deformations can be performed in the presence of sensitizing gases and/or at elevated temperatures.

The term "deformed state" refers to a state of the polymeric material following a deformation process, such as a mechanical deformation, as described herein, at solid or at melt. Following the deformation process, deformed polymeric material at a solid state or at melt is be allowed to solidify/crystallize while still maintains the deformed shape or the newly acquired deformed state.

"IBMA" refers to irradiation below the melt and mechanical annealing. "IBMA" was formerly referred to as "CIMA" (Cold Irradiation and Mechanically Annealed).

The term "mechanically interlocked" refers generally to interlocking of polymeric material and the counterface, that are produced by various methods, including compression molding, heat and irradiation, thereby forming an interlocking interface, resulting into a 'shape memory' of the interlocked polymeric material. Components of a device having such an interlocking interface can be referred to as a "hybrid material". Medical implants having such a hybrid material contain a substantially sterile interface.

The term "substantially sterile" refers to a condition of an object, for example, an interface or a hybrid material or a medical implant containing interface(s), wherein the interface is sufficiently sterile to be medically acceptable, i.e., will not cause an infection or require revision surgery.

"Metallic mesh" refers to a porous metallic surface of various pore sizes, for example, 0.1-3 mm. The porous surface can be obtained through several different methods, for example, sintering of metallic powder with a binder that is subsequently removed to leave behind a porous surface; sintering of short metallic fibers of diameter 0.1-3 mm; or sintering of different size metallic meshes on top of each other to provide an open continuous pore structure.

"Bone cement" refers to what is known in the art as an adhesive used in bonding medical devices to bone. Typically, bone cement is made out of polymethylmethacrylate (PMMA). Bone cement can also be made out of calcium phosphate.

"High temperature compression molding" refers to the compression molding of polymeric material in any form, for example, resin, powder, flakes or particles, to impart new geometry under pressure and temperature. During the high temperature (above the melting point of polymeric material) compression molding, polymeric material is heated to above its melting point, pressurized into a mold of desired shape and allowed to cool down under pressure to maintain a desired shape.

"Shape memory" refers to what is known in the art as the property of polymeric material, for example, an UHMWPE, that attains a preferred high entropy shape when melted. The preferred high entropy shape is achieved when the resin, powder, or flake is consolidated through compression molding.

The phrase "substantially no detectable residual free radicals" refers to a state of a polymeric component, wherein enough free radicals are eliminated to avoid oxidative degradation, which can be evaluated by electron spin resonance (ESR). The phrase "detectable residual free radicals" refers to the lowest level of free radicals detectable by ESR or more. The lowest level of free radicals detectable with state-of-the-art instruments is about $10^{14}$ spins/gram and thus the term "detectable" refers to a detection limit of $10^{14}$ spins/gram by ESR.

The terms "about" or "approximately" in the context of numerical values and ranges refers to values or ranges that approximate or are close to the recited values or ranges such that the invention can perform as intended, such as having a desired degree of cross-linking and/or a desired lack of or quenching of free radicals, as is apparent to the skilled person from the teachings contained herein. This is due, at least in part, to the varying properties of polymer compositions. Thus these terms encompass values beyond those resulting from systematic error. These terms make explicit what is implicit.

"Polymeric materials" or "polymer" include polyethylene, for example, Ultra-high molecular weight polyethylene (UHMWPE) refers to linear non-branched chains of ethylene having molecular weights in excess of about 500,000, preferably above about 1,000,000, and more preferably above about 2,000,000. Often the molecular weights can reach about 8,000,000 or more. By initial average molecular weight is meant the average molecular weight of the UHMWPE starting material, prior to any irradiation. See U.S. Pat. No. 5,879,400, PCT/US99/16070, filed on Jul. 16, 1999, and PCT/US97/02220, filed Feb. 11, 1997. The term "polyethylene article" or "polymeric article" or "polymer" generally refers to articles comprising any "polymeric material" disclosed herein.

"Polymeric materials" or "polymer" also include hydrogels, such as poly (vinyl alcohol), poly (acrylamide), poly (acrylic acid), poly(ethylene glycol), blends thereof, or interpenetrating networks thereof, which can absorb water such that water constitutes at least 1 to 10,000% of their original weight, typically 100 wt % of their original weight or 99% or less of their weight after equilibration in water.

"Polymeric material" or "polymer" can be in the form of resin, flakes, powder, consolidated stock, implant, and can contain additives such as antioxidant(s). The "polymeric material" or "polymer" also can be a blend of one or more of different resin, flakes or powder containing different concentrations of an additive such as an antioxidant. The blending of resin, flakes or powder can be achieved by the blending techniques known in the art. The "polymeric material" also can be a consolidated stock of these blends.

"Blending" generally refers to mixing of a polyolefin in its pre-consolidated form with an additive. If both constituents are solid, blending can be done by using a third component such as a liquid to mediate the mixing of the two components, after which the liquid is removed by evaporating. If the additive is liquid, for example α-tocopherol, then the solid can be mixed with large quantities of liquid, then diluted down to desired concentrations with the solid polymer to obtain uniformity in the blend. In the case where an additive is also an antioxidant, for example vitamin E, or α-tocopherol, then blended polymeric material is also antioxidant-doped. Polymeric material, as used herein, also applies to blends of a polyolefin and a plasticizing agent, for example a blend of UHMWPE resin powder blended with α-tocopherol and consolidated. Polymeric material, as used herein, also applies to blends of an additive, a polyolefin and a plasticizing agent, for example UHMWPE soaked in α-tocopherol.

In one embodiment UHMWPE flakes are blended with α-tocopherol; preferably the UHMWPE/α-tocopherol blend is heated to diffuse the α-tocopherol into the flakes. The UHMWPE/α-tocopherol blend is further blended with virgin UHMWPE flakes to obtain a blend of UHMWPE flakes where some flakes are poor in α-tocopherol and others are rich in α-tocopherol. This blend is then consolidated and irradiated. During irradiation the α-tocopherol poor regions are more highly cross-linked than the α-tocopherol poor regions. Following irradiation the blend is homogenized to diffuse α-tocopherol from the α-tocopherol rich to α-tocopherol poor regions and achieve oxidative stability throughout the polymer.

The products and processes of this invention also apply to various types of polymeric materials, for example, any polypropylene, any polyamide, any polyether ketone, or any polyolefin, including high-density-polyethylene, low-density-polyethylene, linear-low-density-polyethylene, ultra-high molecular weight polyethylene (UHMWPE), copolymers or mixtures thereof. The products and processes of this invention also apply to various types of hydrogels, for example, poly(vinyl alcohol), poly(ethylene glycol), poly(ethylene oxide), poly(acrylic acid), poly(methacrylic acid), poly(acrylamide), copolymers or mixtures thereof, or copolymers or mixtures of these with any polyolefin. Polymeric materials, as used herein, also applies to polyethylene of various forms, for example, resin, powder, flakes, particles, powder, or a mixture thereof, or a consolidated form derived from any of the above. Polymeric materials, as used herein, also applies to hydrogels of various forms, for example, film, extrudate, flakes, particles, powder, or a mixture thereof, or a consolidated form derived from any of the above.

The term "additive" refers to any material that can be added to a base polymer in less than 50 v/v %. This material can be organic or inorganic material with a molecular weight less than that of the base polymer. An additive can impart different properties to the polymeric material, for example, it can be a plasticizing agent, a nucleating agent, or an antioxidant.

The term "plasticizing agent" refers to what is known in the art, a material with a molecular weight less than that of the base polymer, for example vitamin E (α-tocopherol) in unirradiated or cross-linked ultrahigh molecular weight polyethylene or low molecular weight polyethylene in high molecular weight polyethylene, in both cases ultrahigh molecular weight polyethylene being the base polymer. The plasticizing agent is typically added to the base polymer in less than about 20 weight percent. The plasticizing agent generally increases flexibility and softens the polymeric material.

The term "plasticization" or "plasticizing" refers to the properties that a plasticizing agent imparts on the polymeric material to which it has been contacted with. These properties may include but are not limited to increased elongation at break, reduced stiffness and increased ductility.

A "nucleating agent' refers to an additive known in the art, an organic or inorganic material with a molecular weight less than that of the base polymer, which increases the rate of crystallization in the polymeric material. Typically, organocarboxylic acid salts, for example calcium carbonate, are good nucleation agents for polyolefins. Also, nucleating agents are typically used in small concentrations such as 0.5 wt %.

"Cross-linking Polymeric Materials" refers to polymeric materials, for example, UHMWPE can be cross-linked by a variety of approaches, including those employing cross-linking chemicals (such as peroxides and/or silane) and/or irradiation. Preferred approaches for cross-linking employ irradiation. Cross-linked UHMWPE also can be obtained through cold irradiation, warm irradiation, or melt irradiation according to the teachings of U.S. Pat. Nos. 5,879,400, 6,641,617, and PCT/US97/02220.

"Consolidated polymeric material refers" to a solid, consolidated bar stock, solid material machined from stock, or semi-solid form of polymeric material derived from any forms as described herein, for example, resin, powder, flakes, particles, or a mixture thereof, that can be consolidated. The consolidated polymeric material also can be in the form of a slab, block, solid bar stock, machined component, film, tube, balloon, preform, implant, finished medical device or unfinished device.

By "crystallinity" is meant the fraction of the polymer that is crystalline. The crystallinity is calculated by knowing the weight of the sample (weight in grams), the heat absorbed by the sample in melting (E, in J/g) and the heat of melting of polyethylene crystals ($\Delta H = 291$ J/g), and using the following equation according to ASTM F2625 and the like or their successors:

$$\% \text{ Crystallinity} = E/w \cdot \Delta H$$

By tensile "elastic modulus" is meant the ratio of the nominal stress to corresponding strain for strains as determined using the standard test ASTM 638 M III and the like or their successors.

The term "non-permanent device" refers to what is known in the art as a device that is intended for implantation in the body for a period of time shorter than several months. Some non-permanent devices could be in the body for a few seconds to several minutes, while other may be implanted for days, weeks, or up to several months. Non-permanent devices include catheters, tubing, intravenous tubing, and sutures, for example.

"Pharmaceutical compound", as described herein, refers to a drug in the form of a powder, suspension, emulsion, particle, film, cake, or molded form. The drug can be free-standing or incorporated as a component of a medical device.

The term "pressure chamber" refers to a vessel or a chamber in which the interior pressure can be raised to levels above atmospheric pressure.

The term "packaging" refers to the container or containers in which a medical device is packaged and/or shipped. Packaging can include several levels of materials, including bags, blister packs, heat-shrink packaging, boxes, ampoules, bottles, tubes, trays, or the like or a combination thereof. A single component may be shipped in several individual types of package, for example, the component can be placed in a bag, which in turn is placed in a tray, which in turn is placed in a box. The whole assembly can be sterilized and shipped. The packaging materials include, but not limited to, vegetable parchments, multi-layer polyethylene, Nylon 6, polyethylene terephthalate (PET), and polyvinyl chloride-vinyl acetate copolymer films, polypropylene, polystyrene, and ethylene-vinyl acetate (EVA) copolymers.

The term "sealing" refers to the process of isolating a chamber or a package from the outside atmosphere by closing an opening in the chamber or the package. Sealing can be accomplished by a variety of means, including application of heat (for example, thermally-sealing), use of adhesive, crimping, cold-molding, stapling, or application of pressure.

The term "blister packs" refers to a packaging comprised of a rigid plastic bowl with a lid or the like that is either peeled or punctured to remove the packaged contents. The lid is often made of aluminum, or a gas-permeable membrane such as a Tyvek. The blister packs are often blow-molded, a process where the plastic is heated above its deformation temperature, at which point pressurized gas forces the plastic into the required shape.

The term "heat-shrinkable packaging" refers to plastic films, bags, or tubes that have a high degree of orientation in them. Upon application of heat, the packaging shrinks down as the oriented chains retract, often wrapping tightly around the medical device.

The term "intervertebral disc system" refers to an artificial disc that separates the vertebrae in the spine. This system can either be composed of one type of material, or can be a composite structure, for example, cross-linked UHMWPE with metal edges.

The term "balloon catheters" refers to what is known in the art as a device used to expand the space inside blood vessels or similar. Balloon catheters are usually thin wall polymeric devices with an inflatable tip, and can expand blocked arteries, stents, or can be used to measure blood pressure. Commonly used polymeric balloons include, for example, polyether-block co-polyamide polymer (PeBAX®), Nylon, and polyethylene terephthalate (PET) balloons. Commonly used polymeric material used in the balloons and catheters include, for example, co-polymers of polyether and polyamide (for example, PeBAX®), Polyamides, Polyesters (for example, PET), and ethylene vinyl alcohol (EVA) used in catheter fabrication.

Medical device tubing: Materials used in medical device tubing, including an intravenous tubing include, polyvinyl chloride (PVC), polyurethane, polyolefins, and blends or alloys such as thermoplastic elastomers, polyamide/imide, polyester, polycarbonate, or various fluoropolymers.

The term "stent" refers to what is known in the art as a metallic or polymeric cage-like device that is used to hold bodily vessels, such as blood vessels, open. Stents are usually introduced into the body in a collapsed state, and are inflated at the desired location in the body with a balloon catheter, where they remain.

"Melt transition temperature" refers to the lowest temperature at which all the crystalline domains in a material disappear.

The term "interface" in this invention is defined as the niche in medical devices formed when an implant is in a configuration where a component is in contact with another piece (such as a metallic or a non-metallic component), which forms an interface between the polymer and the metal or another polymeric material. For example, interfaces of polymer-polymer or polymer-metal are in medical prosthesis, such as orthopedic joints and bone replacement parts, for example, hip, knee, elbow or ankle replacements.

Medical implants containing factory-assembled pieces that are in close contact with the polyethylene form interfaces. In most cases, the interfaces are not readily accessible to ethylene oxide gas or the gas plasma during a gas sterilization process.

"Irradiation", in one aspect of the invention, the type of radiation, preferably ionizing, is used. According to another aspect of the invention, a dose of ionizing radiation ranging from about 25 kGy to about 1000 kGy is used. The radiation dose can be about 25 kGy, about 50 kGy, about 65 kGy, about 75 kGy, about 100 kGy, about 150, kGy, about 200 kGy, about 300 kGy, about 400 kGy, about 500 kGy, about 600 kGy, about 700 kGy, about 800 kGy, about 900 kGy, or about 1000 kGy, or above 1000 kGy, or any value thereabout or therebetween. Preferably, the radiation dose can be between about 25 kGy and about 150 kGy or between about 50 kGy and about 100 kGy. These types of radiation, including gamma, x-ray, and/or electron beam, kills or inactivates bacteria, viruses, or other microbial agents potentially contaminating medical implants, including the interfaces, thereby achieving product sterility. The irradiation, which may be electron or gamma irradiation, in accordance with the present invention can be carried out in air atmosphere containing oxygen, wherein the oxygen concentration in the atmosphere is at least 1%, 2%, 4%, or up to about 22%, or any value thereabout or therebetween. In another aspect, the irradiation can be carried out in an inert atmosphere, wherein the atmosphere contains gas selected from the group consisting of nitrogen, argon, helium, neon, or the like, or a combination thereof. The irradiation also can be carried out in a sensitizing gas such as acetylene or mixture or a sensitizing gas with an inert gas or inert gases. The irradiation also can be carried out in a vacuum. The irradiation can also be carried out at room temperature, or at between room temperature and the melting point of the polymeric material, or at above the melting point of the polymeric material. The irradiation can be carried out at any temperature or at any dose rate using e-beam, gamma, and/or x-ray. The irradiation temperature can be below or above the melting point of the polymer. The polymer can be first heated and then irradiated. Alternatively, the heat generated by the beam, i.e., radiation generated heating (including adiabatic and partially adiabatic) can increase the temperature of the polymer. Subsequent to the irradiation step the polymer can be heated to melt or heated to a temperature below its melting point for annealing. These post-irradiation thermal treatments can be carried out in air, inert gas and/or in vacuum. Also the irradiation can be carried out in small increments of radiation dose and in some embodiments these sequences of incremental irradiation can be interrupted with a thermal treatment. The sequential irradiation can be carried out with about 1, 10, 20, 30, 40, 50, 100 kGy, or higher radiation dose increments. Between each or some of the increments the polymer can be thermally treated by melting and/or annealing steps. The thermal treatment after irradiation is mostly to reduce or to eliminate the residual free radicals in the polymers created by irradiation, and/or eliminate the crystalline matter, and/or help in the removal of any extractables that may be present in the polymer.

In accordance with a preferred feature of this invention, the irradiation may be carried out in a sensitizing atmosphere. This may comprise a gaseous substance which is of sufficiently small molecular size to diffuse into the polymer and which, on irradiation, acts as a polyfunctional grafting moiety. Examples include substituted or unsubstituted polyunsaturated hydrocarbons; for example, acetylenic hydrocarbons such as acetylene; conjugated or unconjugated olefinic hydrocarbons such as butadiene and (meth)acrylate monomers; sulphur monochloride, with chloro-tri-fluoroethylene (CTFE) or acetylene being particularly preferred. By "gaseous" is meant herein that the sensitizing atmosphere is in the gas phase, either above or below its critical temperature, at the irradiation temperature.

If electron radiation is used, the energy of the electrons also is a parameter that can be varied to tailor the properties of the irradiated polymer. In particular, differing electron energies result in different depths of penetration of the electrons into the polymer. The practical electron energies range from about 0.1 MeV to 16 MeV giving approximate iso-dose penetration levels of 0.5 mm to 8 cm, respectively. The preferred electron energy for maximum penetration is about 10 MeV, which is commercially available through vendors such as Studer (Daniken, Switzerland) or E-Beam Services New Jersey, USA). The lower electron energies may be preferred for embodiments where a surface layer of the polymer is preferentially cross-linked with gradient in cross-link density as a function of distance away from the surface.

The term "dose rate" refers to a rate at which the radiation is carried out. Dose rate can be controlled in a number of ways. One way is by changing the power of the e-beam, scan width, conveyor speed, and/or the distance between the sample and the scan horn. Another way is by carrying out the irradiation in multiple passes with, if desired, cooling or heating steps in-between. With gamma and x-ray radiations the dose rate is controlled by how close the sample is to the radiation source, how intense is the source, the speed at which the sample passes by the source.

Gamma irradiation, however, generally provides low radiation dose rate and requires a longer duration of time, which can result in more in-depth oxidation, particularly if the gamma irradiation is carried out in air. Electron irradiation, in general, results in a more limited dose penetration depth, but requires less time and, therefore, reduces the risk of extensive oxidation if the irradiation is carried out in air. In addition if the desired dose levels are high, for instance 20 Mrad, the irradiation with gamma may take place over one day, leading to impractical production times. On the other hand, the dose rate of the electron beam can be adjusted by varying the irradiation parameters, such as conveyor speed, scan width, and/or beam power. With the appropriate parameters, a 20 Mrad melt-irradiation can be completed in for instance less than 10 minutes. The penetration of the electron beam depends on the beam energy measured by million electron-volts (MeV). Most polymers exhibit a density of about 1 g/cm$^3$, which leads to the penetration of about 1 cm with a beam energy of 2-3 MeV and about 4 cm with a beam energy of 10 MeV. The penetration of e-beam is known to increase slightly with increased irradiation temperatures. If electron irradiation is preferred, the desired depth of penetration can be adjusted based on the beam energy. Accordingly, gamma irradiation or electron irradiation may be used based upon the depth of penetration preferred, time limitations and tolerable oxidation levels.

Ranges of acceptable dose rates are exemplified in International Application WO 97/29793. In general, the dose rates vary between 0.5 Mrad/pass and 50 Mrad/pass. The upper limit of the dose rate depends on the resistance of the polymer to cavitation/cracking induced by the irradiation.

If electron radiation is utilized, the energy of the electrons also is a parameter that can be varied to tailor the properties of the irradiated polymer. In particular, differing electron energies result in different depths of penetration of the electrons into the polymer. The practical electron energies range from about 0.1 MeV to 16 MeV giving approximate iso-dose penetration levels of 0.5 mm to 8 cm, respectively. The preferred electron energy for maximum penetration is about 10 MeV, which is commercially available through vendors such as Studer (Daniken, Switzerland) or E-Beam Services New Jersey, USA). The lower electron energies may be preferred for embodiments where a surface layer of the polymer is preferentially cross-linked with gradient in cross-link density as a function of distance away from the surface.

In accordance with another aspect of the invention, the polymeric preform also has a gradient of cross-link density in a direction perpendicular to the direction of irradiation, wherein a part of the polymeric preform was preferentially shielded to partially block radiation during irradiation in order to provide the gradient of cross-link density, wherein the preferential shielding is used where a gradient of cross-link density is desired and the gradient of cross-link density is in a direction perpendicular to the direction of irradiation on the preferentially shielded polymeric preform, such as is disclosed in allowed U.S. Pat. No. 7,205,339, the methodologies of which are hereby incorporated by reference.

"Metal Piece", in accordance with the invention, the piece forming an interface with polymeric material is, for example, a metal. The metal piece in functional relation with polymeric material, according to the present invention, can be made of a cobalt chrome alloy, stainless steel, titanium, titanium alloy or nickel cobalt alloy, for example.

"Non-metallic Piece", in accordance with the invention, the piece forming an interface with polymeric material is, for example, a non-metal. The non-metal piece in functional relation with polymeric material, according to the present invention, can be made of ceramic material, for example.

The term "inert atmosphere" refers to an environment having no more than 1% oxygen and more preferably, an oxidant-free condition that allows free radicals in polymeric materials to form cross links without oxidation during a process of sterilization. An inert atmosphere is used to avoid $O_2$, which would otherwise oxidize the medical device comprising a polymeric material, such as UHMWPE. Inert atmospheric conditions such as nitrogen, argon, helium, or neon are used for sterilizing polymeric medical implants by ionizing radiation.

Inert atmospheric conditions such as nitrogen, argon, helium, neon, or vacuum are also used for sterilizing interfaces of polymeric-metallic and/or polymeric-polymeric in medical implants by ionizing radiation.

Inert atmospheric conditions also refer to an inert gas, inert fluid, or inert liquid medium, such as nitrogen gas or silicon oil.

"Anoxic environment" refers to an environment containing gas, such as nitrogen, with less than 21%-22% oxygen, preferably with less than 2% oxygen. The oxygen concentration in an anoxic environment also can be at least about 1%, 2%, 4%, 6%, 8%, 10%, 12% 14%, 16%, 18%, 20%, or up to about 22%, or any value thereabout or therebetween.

The term "vacuum" refers to an environment having no appreciable amount of gas, which otherwise would allow free radicals in polymeric materials to form cross links without oxidation during a process of sterilization. A vacuum is used to avoid $O_2$, which would otherwise oxidize the medical device comprising a polymeric material, such as UHMWPE. A vacuum condition can be used for sterilizing polymeric medical implants by ionizing radiation.

A vacuum condition can be created using a commercially available vacuum pump. A vacuum condition also can be used when sterilizing interfaces of polymeric-metallic and/or polymeric-polymeric in medical implants by ionizing radiation.

A "sensitizing environment" or "sensitizing atmosphere" refers to a mixture of gases and/or liquids (at room temperature) that contain sensitizing gaseous and/or liquid component(s) that can react with residual free radicals to assist in the recombination of the residual free radicals. The gases maybe acetylene, chloro-trifluoro ethylene (CTFE), ethylene, or like. The gases or the mixtures of gases thereof may contain noble gases such as nitrogen, argon, neon and like. Other gases such as, carbon dioxide or carbon monoxide may also be present in the mixture. In applications where the surface of a treated material is machined away during the device manufacture, the gas blend could also contain oxidizing gases such as oxygen. The sensitizing environment can be dienes with different number of carbons, or mixtures of liquids and/or gases thereof. An example of a sensitizing liquid component is octadiene or other dienes, which can be mixed with other sensitizing liquids and/or non-sensitizing liquids such as a hexane or a heptane. A sensitizing environment can include a sensitizing gas, such as acetylene, ethylene, or a similar gas or mixture of gases, or a sensitizing liquid, for example, a diene. The environment is heated to a temperature ranging from room temperature to a temperature below the melting point of the material.

In certain embodiments of the present invention in which the sensitizing gases and/or liquids or a mixture thereof, inert gas, air, vacuum, and/or a supercritical fluid can be present at any of the method steps disclosed herein, including blending, mixing, consolidating, quenching, irradiating, annealing, mechanically deforming, doping, homogenizing, heating, melting, and packaging of the finished product, such as a medical implant.

"Residual free radicals" refers to free radicals that are generated when a polymer is exposed to ionizing radiation such as gamma or e-beam irradiation. While some of the free radicals recombine with each other to from cross-links, some become trapped in crystalline domains. The trapped free radicals are also known as residual free radicals.

According to one aspect of the invention, the levels of residual free radicals in the polymer generated during an ionizing radiation (such as gamma or electron beam) is preferably determined using electron spin resonance and treated appropriately to reduce the free radicals.

"Sterilization", one aspect of the present invention discloses a process of sterilization of medical implants containing polymeric material, such as cross-linked UHMWPE. The process comprises sterilizing the medical implants by ionizing sterilization with gamma or electron beam radiation, for example, at a dose level ranging from about 25-70 kGy, or by gas sterilization with ethylene oxide or gas plasma.

Another aspect of the present invention discloses a process of sterilization of medical implants containing polymeric material, such as cross-linked UHMWPE. The process comprises sterilizing the medical implants by ionizing sterilization with gamma or electron beam radiation, for example, at a dose level ranging from 25-200 kGy. The dose level of sterilization is higher than standard levels used in irradiation. This is to allow cross-linking or further cross-linking of the medical implants during sterilization.

One aspect of the present invention discloses a process of increasing the uniformity of the antioxidant following doping in polymeric component of a medical implant during the manufacturing process by heating for a time period depending on the melting temperature of the polymeric material. For example, the preferred temperature is about 137° C. or less. Another aspect of the invention discloses a heating step that can be carried in the air, in an atmosphere, containing oxygen, wherein the oxygen concentration is at least about 1%, 2%, 4%, or up to about 22%, or any value thereabout or therebetween. In another aspect, the invention discloses a heating step that can be carried while the implant is in contact with an inert atmosphere, wherein the inert atmosphere contains gas selected from the group consisting of nitrogen, argon, helium, neon, or the like, or a combination thereof. In another aspect, the invention discloses a heating step that can be carried while the implant is in contact with a non-oxidizing medium, such as an inert fluid medium, wherein the medium contains no more than about 1% oxygen. In another aspect, the invention discloses a heating step that can be carried while the implant is in a vacuum.

The term "radiation generated heat" refers to the heat generated as a result of conversion of some of the energies deposited by the electrons or gamma rays to heat during an irradiation process. Radiation generated heating, which includes adiabatic and partially adiabatic heating, primarily depends on how well the sample is thermally insulated during the irradiation. With good thermal insulation, most of the heat generated is not lost to the surroundings and leads to the radiation generated heating (adiabatic and partially adiabatic) of the polymer to a higher temperature than the irradiation temperature. The heating also could be induced by using a high enough dose rate to minimize the heat loss to the surroundings. The radiation generated heating (including adiabatic and partially adiabatic) depends on a number of processing parameters such as dose rate, initial temperature of the sample, absorbed radiation dose, and the like. Radiation generated heating (including adiabatic and partially adiabatic) is a result of the conversion of the radiation dose to heat in the irradiated sample. If the temperature of the sample is high enough during melting, radiation generated heating (including adiabatic and partially adiabatic) results in melting of the crystals. Even when the initial temperature of the polymer is low, for example, near room temperature or 40° C., the radiation generated heating (including adiabatic and partially adiabatic) can be high enough to increase the temperature of the polymer during irradiation. If the initial temperature and radiation dose are too high, radiation generated heating (including adiabatic and partially adiabatic) may result in complete melting of the polymer.

It should be noted that in theoretical thermodynamics, "adiabatic heating" refers to an absence of heat transfer to the surroundings. In the practice, such as in the creation of new polymeric materials, "adiabatic heating" refers to situations where a sufficient majority of thermal energy is imparted on the starting material and is not transferred to the surroundings. Such can be achieved by the combination of insulation, irradiation dose rates and irradiation time periods, as disclosed herein and in the documents cited herein. Thus, what may approach adiabatic heating in the theoretical sense achieves it in the practical sense. However, not all warm irradiation refers to an "adiabatic heating." Warm irradiation also can have non-adiabatic or partially (such as 10-75% of the heat generated are lost to the surroundings) adiabatic heating.

In an aspect of this invention, room temperature irradiation refers that the polymeric material is at ambient temperature is not heated by an external heating element before or during irradiation. However, the irradiation itself may heat up the polymeric material. In some cases the radiation dose is lower, which only results in minor rise in temperature in the polymeric material, and in some other cases the radiation dose is higher, which results in large increases in temperature in the polymeric material. Similarly the dose rate also plays an important role in the heating of the polymeric material during irradiation. At low dose rate the temperature rise is smaller while with larger dose rates the radiation imparted heating becomes more adiabatic and leads to larger increases in the temperature of the polymeric material. In any of these cases, as long as there is no other heating source other than radiation itself, the process is considered as room temperature irradiation.

In another aspect of this invention, there is described the heating method of implants to increase the uniformity of the antioxidant. The medical device comprising a polymeric raw material, such as UHMWPE, is generally heated to a temperature of about 137° C. or less following the step of doping with the antioxidant. The medical device is kept heated in the inert medium until the desired uniformity of the antioxidant is reached.

The term "below melting point" or "below the melt" refers to a temperature below the melting point of a polymeric material, for example, polyethylene such as UHMWPE. The term "below melting point" or "below the melt" refers to a temperature less than about 145° C., which may vary depending on the melting temperature of the polymeric material, for example, about 145° C., 140° C. or 135° C., which again depends on the properties of the polymeric material being treated, for example, molecular weight averages and ranges, batch variations, etc. The melting temperature is typically measured using a differential scanning calorimeter (DSC) at a heating rate of 10° C. per minute. The peak melting temperature thus measured is referred to as melting point, also referred as transition range in temperature from crystalline to amorphous phase, and occurs, for example, at approximately 137° C. for some grades of UHMWPE. It may be desirable to conduct a melting study on the starting polymeric material in order to determine the melting temperature and to decide upon an irradiation and annealing temperature. Generally, the melting temperature of polymeric material is increased when the polymeric material is under pressure.

The term "heating" refers to thermal treatment of the polymer at or to a desired heating temperature. In one aspect, heating can be carried out at a rate of about 10° C. per minute to the desired heating temperature. In another aspect, the heating can be carried out at the desired heating temperature for desired period of time. In other words, heated polymers can be continued to heat at the desired temperature, below or above the melt, for a desired period of time. Heating time at or to a desired heating temperature can be at least 1 minute to 48 hours to several weeks long. In one aspect the heating time is about 1 hour to about 24 hours. In another aspect, the heating can be carried out for any time period as set forth herein, before or after irradiation. Heating temperature refers to the thermal condition for heating in accordance with the invention. Heating can be performed at any time in a process, including during, before and/or after irradiation. Heating can be done with a heating element. Other sources of energy include the environment and irradiation.

The term "annealing" refers to heating or a thermal treatment condition of the polymers in accordance with the invention. Annealing generally refers to continued heating the polymers at a desired temperature below its peak melting point for a desired period of time. Annealing time can be at least 1 minute to several weeks long. In one aspect the annealing time is about 4 hours to about 48 hours, preferably 24 to 48 hours and more preferably about 24 hours. "Annealing temperature" refers to the thermal condition for annealing in accordance with the invention. Annealing can be performed at any time in a process, including during, before and/or after irradiation.

In certain embodiments of the present invention in which annealing can be carried out, for example, in an inert gas, e.g., nitrogen, argon or helium, in a vacuum, in air, and/or in a sensitizing atmosphere, for example, acetylene.

The term "contacted" includes physical proximity with or touching such that the sensitizing agent can perform its intended function. Preferably, a polymeric composition or preform is sufficiently contacted such that it is soaked in the sensitizing agent, which ensures that the contact is sufficient. Soaking is defined as placing the sample in a specific environment for a sufficient period of time at an appropriate temperature, for example, soaking the sample in a solution of an antioxidant. The environment is heated to a temperature ranging from room temperature to a temperature below the melting point of the material. The contact period ranges from at least about 1 minute to several weeks and the duration depending on the temperature of the environment.

The term "non-oxidizing" refers to a state of polymeric material having an oxidation index (A.U.) of less than about 0.5, according to ASTM F2102 or equivalent, following aging polymeric materials for 5 weeks in air at 80° C. oven. Thus, a non-oxidizing cross-linked polymeric material generally shows an oxidation index (A.U.) of less than about 0.5 after the aging period.

The term "oxidatively stable" or "oxidative stability" or "oxidation-resistant" refers a state of polymeric material having an oxidation index (A.U.) of less than about 0.1 following aging polymeric materials for 5 weeks in air at 80° C. oven. Thus, a oxidatively stable or oxidation-resistant cross-linked polymeric material generally shows an oxidation index (A.U.) of less than about 0.1 after the aging period.

The term "surface" of a polymeric material refers generally to the exterior region of the material having a thickness of about 1.0 µm to about 2 cm, preferably about 1.0 mm to about 5 mm, more preferably about 2 mm of a polymeric material or a polymeric sample or a medical device comprising polymeric material.

The term "bulk" of a polymeric material refers generally to an interior region of the material having a thickness of about 1.0 µm to about 2 cm, preferably about 1.0 mm to about 5 mm, more preferably about 2 mm, from the surface of the polymeric material to the center of the polymeric material. However, the bulk may include selected sides or faces of the polymeric material including any selected surface, which may be contacted with a higher concentration of antioxidant.

Although the terms "surface" and "bulk" of a polymeric material generally refer to exterior regions and the interior regions, respectively, there generally is no discrete boundary between the two regions. But, rather the regions are more of a gradient-like transition. These can differ based upon the size and shape of the object and the resin used.

The term "doping" refers to a general process known in the art (see, for example, U.S. Pat. Nos. 6,448,315 and 5,827,904). In this connection, doping generally refers to contacting a polymeric material with an antioxidant under certain conditions, as set forth herein, for example, doping UHMWPE with an antioxidant under supercritical conditions.

In certain embodiments of the present invention in which doping of antioxidant is carried out at a temperature above the melting point of the polymeric material, the antioxidant-doped polymeric material can be further heated above the melt or annealed to eliminate residual free radicals after irradiation. Melt-irradiation of polymeric material in presence of an antioxidant, such as vitamin E, can change the distribution of the vitamin E concentration and also can change the mechanical properties of the polymeric material. These changes can be induced by changes in crystallinity and/or by the plasticization effect of vitamin E at certain concentrations.

According to one embodiment, the surface of the polymeric material is contacted with little or no antioxidant and bulk of the polymeric material is contacted with a higher concentration of antioxidant.

According to another embodiment, the surface of the polymeric material is contacted with no antioxidant and bulk of the polymeric material is contacted with a higher concentration of antioxidant.

According to one embodiment, the bulk of the polymeric material is contacted with little or no antioxidant and surface of the polymeric material is contacted with a higher concentration of antioxidant.

According to another embodiment, the bulk of the polymeric material is contacted with no antioxidant and surface of the polymeric material is contacted with a higher concentration of antioxidant.

According to another embodiment, the surface of the polymeric material and the bulk of the polymeric material are contacted with the same concentration of antioxidant.

According to one embodiment, the surface of the polymeric material may contain from about 0 wt % to about 50 wt % antioxidant, preferably about 0.001 wt % to about 10 wt %, preferably between about 0.01 wt % to about 0.5 wt %, more preferably about 0.2 wt %. According to another embodiment, the bulk of the polymeric material may contain from about 0 wt % to about 50 wt %, preferably about 0.001 wt % to about 10 wt %, preferably between about 0.01 wt % to about 0.5 wt %, more preferably about 0.2 wt %, preferably between about 0.2 wt % and about 1% wt %, preferably about 0.5 wt %.

According to another embodiment, the antioxidant concentration in the polymeric material can be about 1 ppm to about 10,000 ppm, preferably about 100 ppm, about 500 ppm, about 1000 ppm, about 2000 ppm, about 3000 ppm, about 5000 ppm, or to any value thereabout or therebetween.

According to another embodiment, the radiation dose is adjusted depending on the concentration of the antioxidant to achieve a desired cross-link density. At higher antioxidant concentrations, generally a higher dose level is required in order to reach the same cross-link density.

According to another embodiment, the surface of the polymeric material and the bulk of the polymeric material contain the same concentration of antioxidant.

More specifically, consolidated polymeric material can be doped with an antioxidant by soaking the material in a solution of the antioxidant. This allows the antioxidant to diffuse into the polymer. For instance, the material can be soaked in 100% antioxidant. The material also can be soaked in an antioxidant solution where a carrier solvent can be used to dilute the antioxidant concentration. To increase the depth of diffusion of the antioxidant, the material can be doped for longer durations, at higher temperatures, at higher pressures, and/or in presence of a supercritical fluid.

The antioxidant can be diffused to a depth of about 5 mm or more from the surface, for example, to a depth of about 3-5 mm, about 1-3 mm, or to any depth thereabout or therebetween.

The doping process can involve soaking of a polymeric material, medical implant or device with an antioxidant, such as vitamin E, for about half an hour up to several days, preferably for about one hour to 24 hours, more preferably for one hour to 16 hours. The antioxidant can be at room temperature or heated up to about 137° C. and the doping can be carried out at room temperature or at a temperature up to about 137° C. Preferably the antioxidant solution is heated to a temperature between about 100° C. and 135° C. or between about 110° C. and 130° C., and the doping is carried out at a temperature between about 100° C. and 135° C. or between about 110° C. and 130° C. More preferably, the antioxidant solution is heated to about 120° C. and the doping is carried out at about 120° C.

Doping with α-tocopherol through diffusion at a temperature above the melting point of the irradiated polymeric material (for example, at a temperature above 137° C. for UHMWPE) can be carried out under reduced pressure, ambient pressure, elevated pressure, and/or in a sealed chamber, for about 0.1 hours up to several days, preferably for about 0.5 hours to 6 hours or more, more preferably for about 1 hour to 5 hours. The antioxidant can be at a temperature of about 137° C. to about 400° C., more preferably about 137° C. to about 200° C., more preferably about 137° C. to about 160° C.

The doping and/or the irradiation steps can be followed by an additional step of homogenization. The term "homogenization" refers to a heating step in air or in anoxic environment to improve the spatial uniformity of the antioxidant concentration within the polymeric material, medical implant or device. Homogenization also can be carried out before and/or after the irradiation step. The heating may be carried out above or below or at the peak melting point. Antioxidant-doped or -blended polymeric material can be homogenized at a temperature below or above or at the peak melting point of the polymeric material for a desired period of time, for example, the antioxidant-doped or -blended polymeric material can be homogenized for about an hour to several days at room temperature to about 400° C. Preferably, the homogenization is carried out at 90° C. to 180° C., more preferably 100° C. to 137° C., more preferably 120° C. to 135° C., most preferably 130° C. Homogenization is preferably carried out for about one hour to several days to two weeks or more, more preferably about 12 hours to 300 hours or more, more preferably about 280 hours, or more preferably about 200 hours. More preferably, the homogenization is carried out at about 130° C. for about 36 hours or at about 120° C. for about 24 hours. The polymeric material, medical implant or device is kept in an inert atmosphere (nitrogen, argon, and/or the like), under vacuum, or in air during the homogenization process. The homogenization also can be performed in a chamber with supercritical fluids such as carbon dioxide or the like. The pressure of the supercritical fluid can be about 1000 to about 3000 psi or more, more preferably about 1500 psi. It is also known that pressurization increases the melting point of UHMWPE. A temperature higher than 137° C. can be used for homogenization below the melting point if applied pressure has increased the melting point of UHMWPE beyond 137° C.

Homogenization enhances the diffusion of the antioxidant from antioxidant-rich regions to antioxidant poor regions. The diffusion is generally faster at higher temperatures. At a temperature above the melting point the hindrance of diffusion from the crystalline domains is eliminated and the homogenization occurs faster. Melt-homogenization and subsequent recrystallization may reduce the mechanical properties mostly due to a decline in the crystallinity of the polymer. This may be acceptable or even desirable for certain applications. For example, applications where the decline in mechanical properties is not desirable the homogenization can be carried out below the melting point. Alternatively, below or above the melt homogenized samples may be subjected to high pressure crystallization to further improve their mechanical properties.

The polymeric material, medical implant or device is kept in an inert atmosphere (nitrogen, argon, neon, and/or the like), under vacuum, or in air during the homogenization process. The homogenization also can be performed in a chamber with supercritical fluids such as carbon dioxide or the like. The pressure of the supercritical fluid can be 1000 to 3000 psi or more, more preferably about 1500 psi. The homogenization can be performed before and/or after and/or during the diffusion of the antioxidant.

Each composition and aspects, and each method and aspects, which are described above can be combined with another in various manners consistent with the teachings contained herein. According to the embodiments and aspects of the inventions, all methods and the steps in each method can be applied in any order and repeated as many times in a manner consistent with the teachings contained herein.

The invention is further described by the following examples, which do not limit the invention in any manner.

EXAMPLES

VITAMIN E: Vitamin E (Acros™ 99% D-α-Tocopherol, Fisher Brand), was used in the experiments described herein, unless otherwise specified. The vitamin E used is very light yellow in color and is a viscous fluid at room temperature. Its melting point is 2-3° C.

DETERMINATION OF VITAMIN E INDEX (A.U.): Fourier transform infrared spectroscopy (FTIR) is used to quantify the Vitamin E content in the UHMWPE. The FTIR, in other words also known as infra-red microscopy, is used to quantify the Vitamin E content by measuring the vitamin E index, which is a dimensionless parameter.

The absorption peak associated with the alpha-tocopherol is located at 1265 cm-1, which is then normalized with a methylene peak at 1895 cm-1. This ratio is reported as a vitamin E index.

The sample is prepared by microtoming a slice between 100 and 200 micrometers thick through the thickness of the sample. The section must be microtomed orthogonally to the scan direction to prevent spreading the alpha-tocopherol in the through-thickness direction. The slice is mounted on the translating stage of a FTIR microscope, and FTIR spectra are collected a specified intervals from the surface into the bulk of the sample.

The vitamin E index can be converted into an absolute concentration by comparing the index to a calibration curve prepared from UHMWPE sections containing known amounts of Vitamin E.

Example 1

Shelf Aging of Irradiated UHMWPE/Vitamin E Blends 0.02 wt %, 0.05 wt %, and 0.1 wt % vitamin-E/UHMWPE blends were prepared by compression molding. The blends were gamma irradiated in air at room temperature to 150 and 200 kGy and test samples were then machined. The blends were then aged by immersing in a water tank kept at 40° C. for 10 months. Controls samples were made by gamma irradiating UHMWPE in air at room temperature to either 150 or 200 kGy followed by soaking in vitamin-E at 120° C. for two hours and subsequently homogenizing at 120° C. for two hours. The controls samples were gamma sterilized in air and aged in the same water tank kept at 40° C. for 10 months.

The test samples were cut, microtomed, and analyzed using infra-red microscopy per ASTM F2102. The irradiated blends had oxidized; in contrast the controls showed no detectable oxidation (See FIG. 1). FIG. 1 shows oxidation profile as a function of depth of UHMWPE samples made from powder containing varying levels of Vitamin E. Following consolidation, samples were irradiated to differing dose levels, then aged for 10 months at 40° C. in a water tank. The controls were irradiated, then doped in Vitamin E prior to aging (see FIG. 1). FIG. 1 shows that after 10 months of real time aging in water at 40° C. the vitamin-E blended and irradiated samples showed detectable oxidation. The oxidation was highest at the surface and decreased with depth away from the free surfaces. Oxidation was higher with higher radiation dose level and/or with lower vitamin E concentration. In contrast, with the blended and irradiated samples, the irradiated and then vitamin-E doped samples showed negligible oxidation levels after 10 months (detection limit of the IR method is an oxidation index of about 0.1). The difference between the irradiated and vitamin E doped samples and the blended then irradiated samples is that in the former samples the vitamin E is not exposed to irradiation. Hence, its antioxidant activity remains unaffected by radiation. In contrast, the with the latter samples vitamin E is exposed to irradiation and hence loose some of their antioxidant capacity, which results in the real-time oxidation as shown in FIG. 1. Therefore, further stabilization of irradiated blends is needed to prevent their long-term oxidative instability. Interestingly, accelerated aging tests on similar specimens were not able to detect the oxidation differences identified in the long-term test.

Example 2

Figure 2:
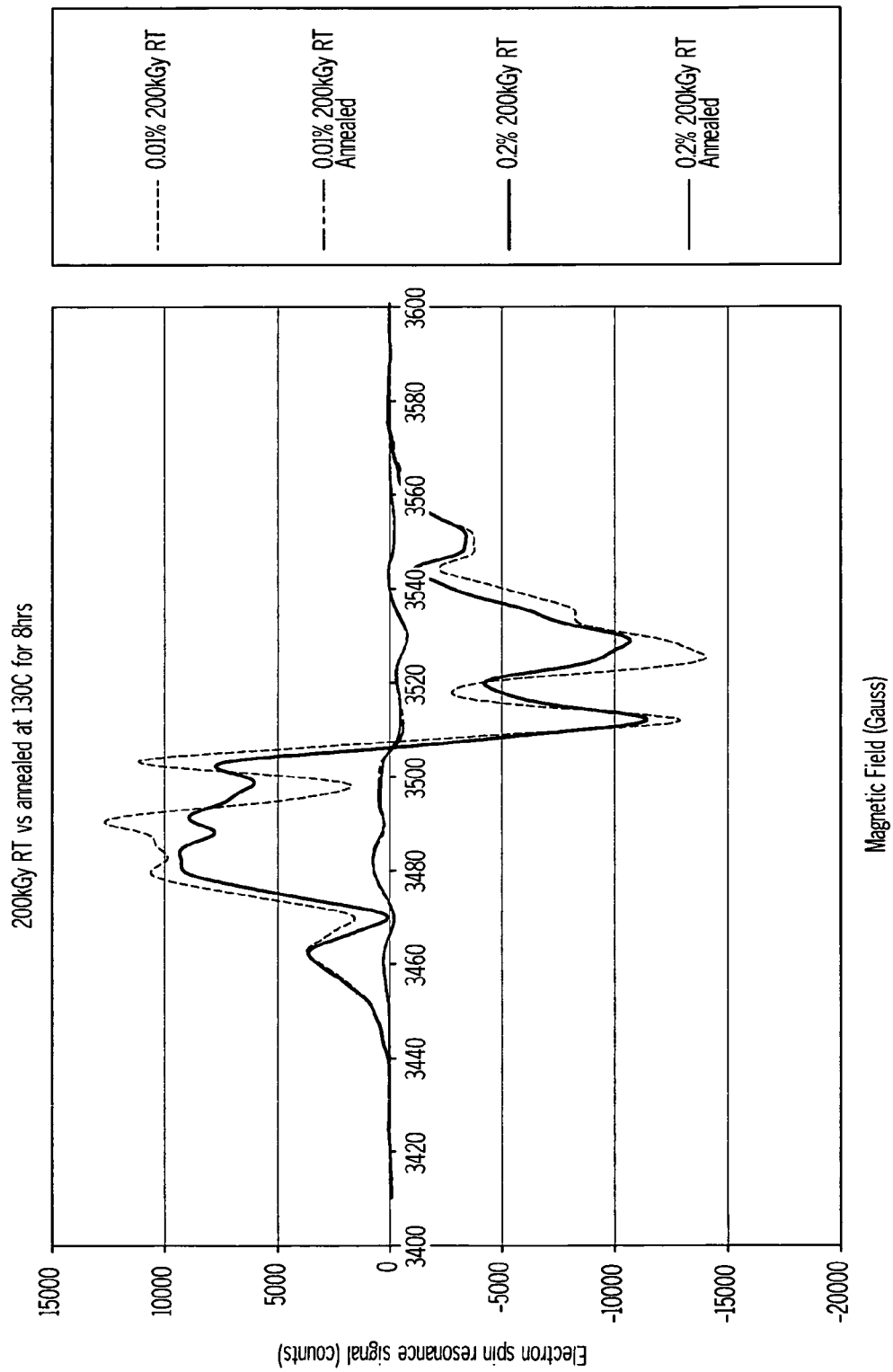
FIG. 2 shows electron spin resonance signal (counts vs. magnetic field (Gauss)) of blends of Vitamin E and UHMWPE powder that were irradiated to 200 kGy at room temperature after consolidation, then annealed at 130° C. for 8 hours. The decreasing peak size indicates the reduction in residual free radicals.
Figure 3:
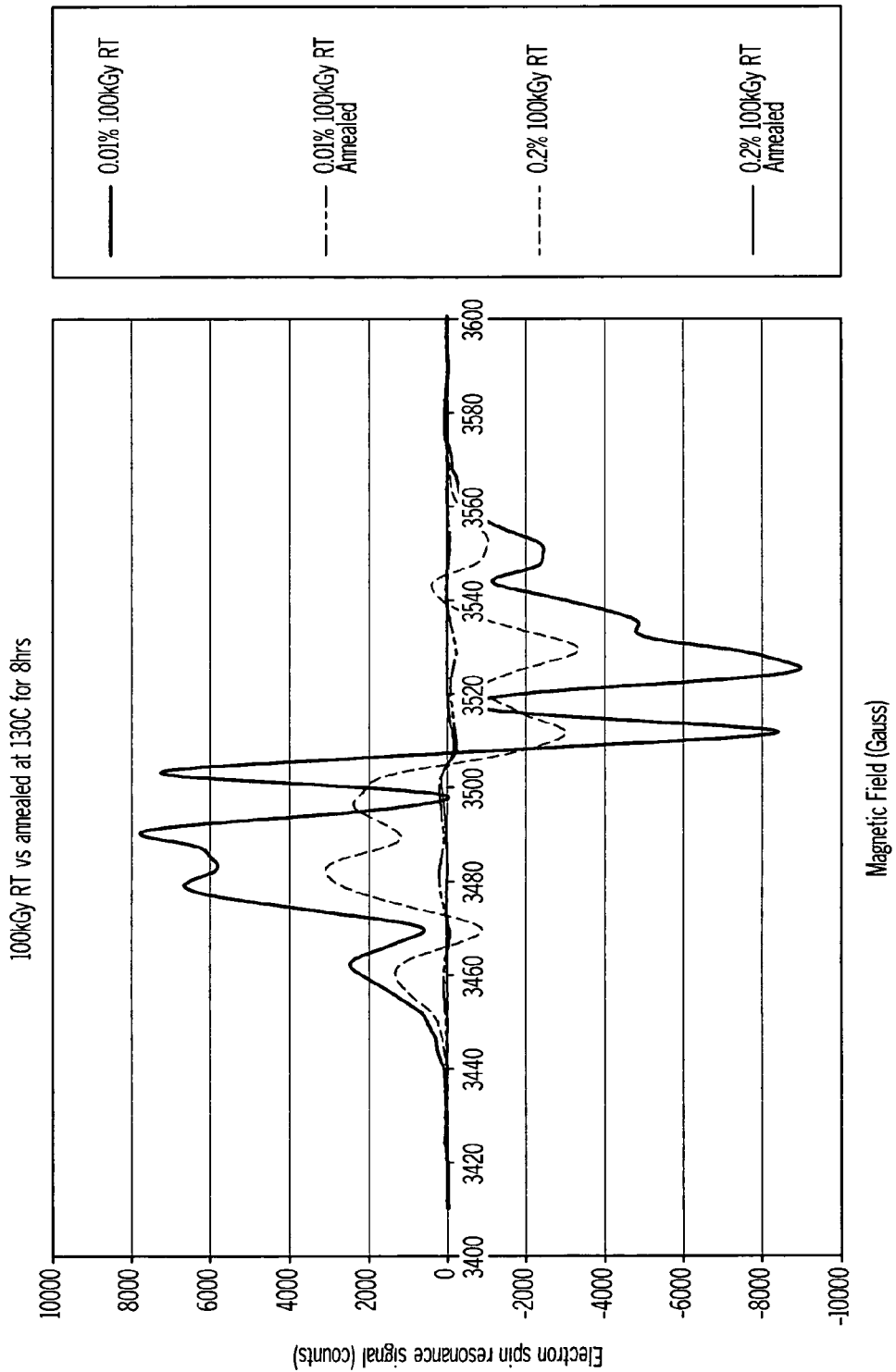
FIG. 3 depicts electron spin resonance signal (counts vs. magnetic field (Gauss)) of blends of Vitamin E and UHMWPE powder that were irradiated to 100 kGy at room temperature after consolidation, then annealed at 130° C. for 8 hours. The decreasing peak size indicates the reduction in residual free radicals.

Annealing of Irradiated UHMWPE/Vitamin-E Blends 0.01 wt % and 0.2 wt % vitamin-E/UHMWPE blends were prepared and irradiated with a Van de Graff electron beam generator operating at 2.5 MeV to a total absorbed radiation dose of either 200 kGy (See FIG. 2) or 100 kGy (See FIG. 3). The irradiation was in air at room temperature at a dose rate of 25 kGy/pass and a conveyor speed of 20 cm/min. Half of each sample was then annealed in air at 130° C. for 8 hours (See FIG. 4). Electron spin resonance (ESR) measurements were carried out in both the as-irradiated and irradiated-annealed samples. ESR showed a marked decrease in the concentration of residual free radicals with annealing.

TABLE 1

The free radical concentration of the irradiated vitamin E blends before and after annealing.

| Sample ID (Vitamin E concentration; radiation dose) | Free Radical Concentration (Spins per gram) |
| --- | --- |
| 0.01%; 100 kGy | 9.28E+16 |
| 0.01%; 100 kGy annealed | 1.75E+15 |
| 0.2%; 100 kGy | 4.31E+16 |
| 0.2%; 100 kGy annealed | 6.76E+13 |
| 0.01%; 200 kGy | 1.54E+17 |
| 0.01%; 200 kGy annealed | 1.09E+16 |
| 0.2%; 200 kGy | 1.23E+17 |
| 0.2%; 200 kGy annealed | 6.71E+15 |

Figure 4:
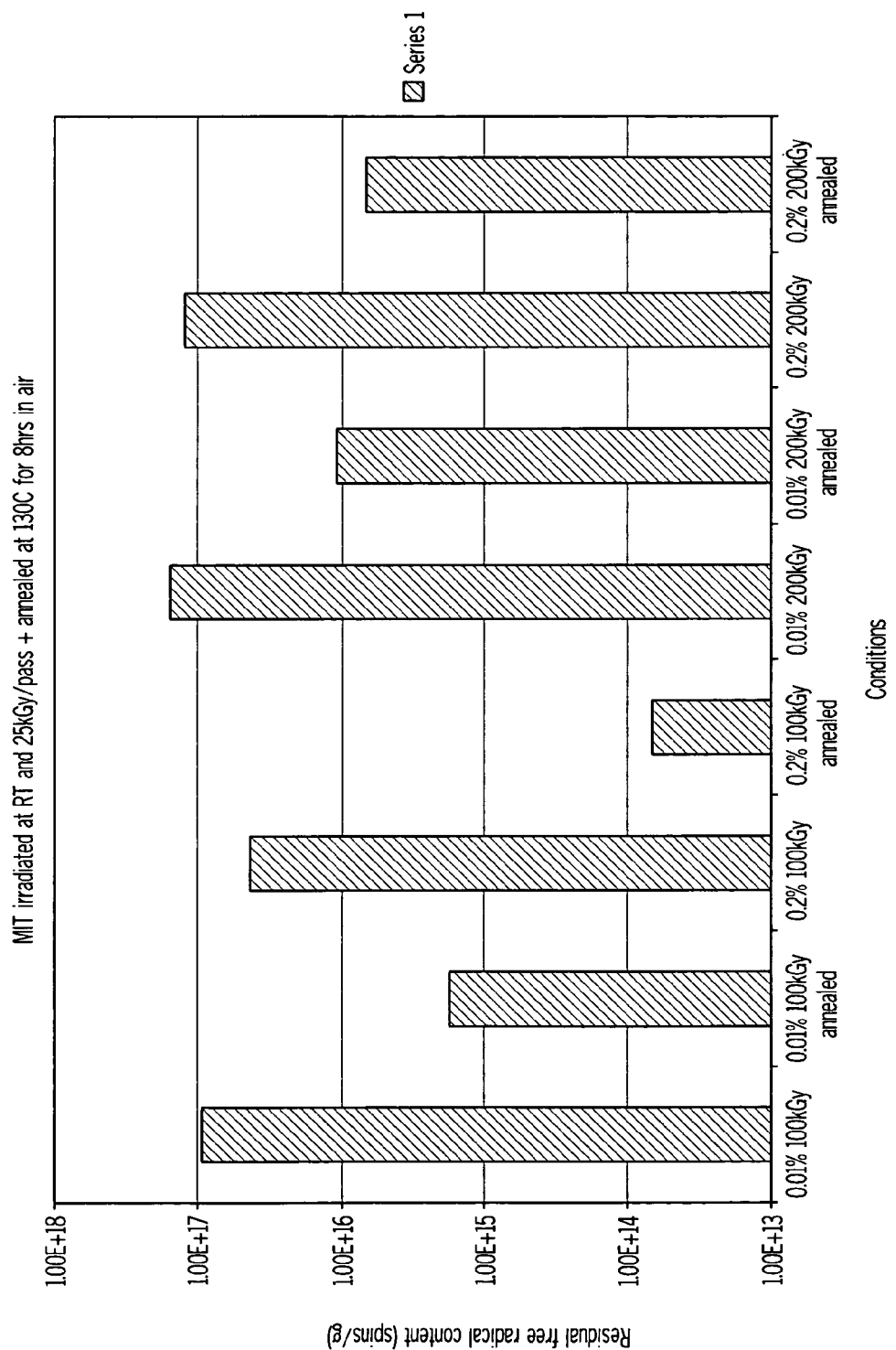
FIG. 4 illustrates residual free radical content (spins/g) as a function of processing conditions.

FIG. 2 shows electron spin resonance signal of blends of Vitamin E and UHMWPE powder that were irradiated to 200 kGy at room temperature after consolidation, then annealed at 130° C. for 8 hours. The decreasing peak size indicates the reduction in residual free radicals (see FIG. 2). FIG. 3 depicts electron spin resonance signal of blends of Vitamin E and UHMWPE powder that were irradiated to 100 kGy at room temperature after consolidation, then annealed at 130° C. for 8 hours. The decreasing peak size indicates the reduction in residual free radicals (see FIG. 3). FIG. 4 illustrates residual free radical content (spins/g) as a function of processing conditions. Table 1 shows the free radical concentration of the irradiated vitamin E blends before and after annealing. Annealing reduced the free radical content and the reduction was more effective with increasing vitamin E concentration.

Example 3

Figure 5:
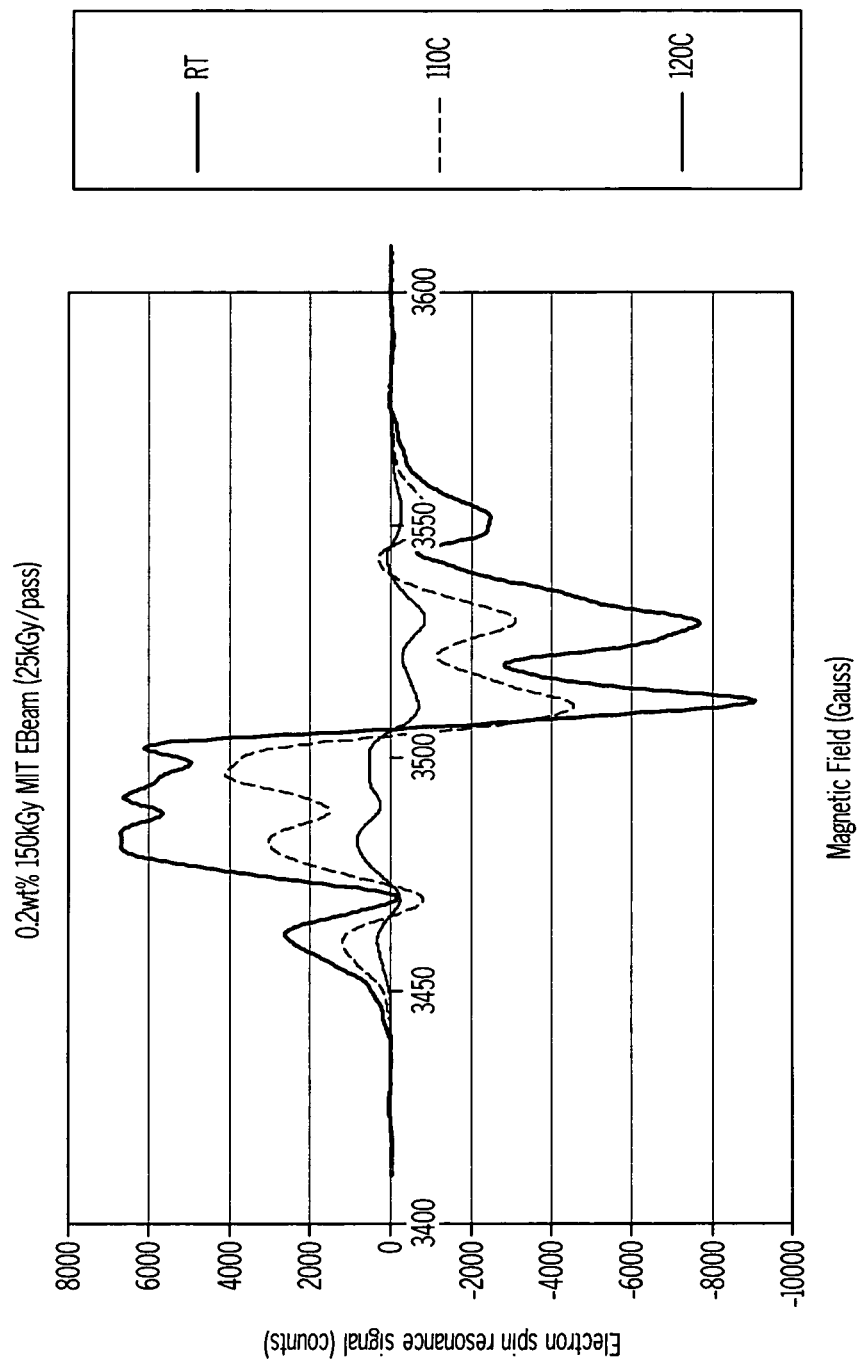
FIG. 5 shows electron spin resonance signal (counts vs. magnetic field (Gauss)) of blends of Vitamin E (0.2 wt %) and UHMWPE powder that were irradiated to 150 kGy at a dose rate of 25 kGy/pass at room temperature, 110° C., and 120° C. after consolidation. The ESR signal is due to the presence of residual free radicals. The decreasing peak size indicates the reduction in residual free radicals with increasing irradiation temperature.

Effect of Irradiation Temperature on the Residual Free Radical Concentration of Irradiated Blends 0.2 wt % vitamin-E/UHMWPE blends were prepared and irradiated with a Van de Graff electron beam generator operating at 2.5 MeV to a total absorbed radiation dose of either 200 kGy or 100 kGy. The irradiation was in air at room temperature, 1110° C., or 120° C. at a dose rate of 25 kGy/pass and a conveyor speed of 20 cm/min (See FIG. 5). FIG. 5 shows electron spin resonance signal of blends of Vitamin E (0.2 wt %) and UHMWPE powder that were irradiated to 150 kGy at room temperature, 110° C., and 120° C. after consolidation. The decreasing peak size indicates the reduction in residual free radicals with increasing irradiation temperature (See FIG. 5). Electron spin resonance (ESR) measurements were carried out with all three test samples. ESR showed a marked decrease in the concentration of residual freer radicals with increasing irradiation temperature.

Example 4

Comparison of Warm Irradiation to Post-Irradiation Annealing

Figure 6:
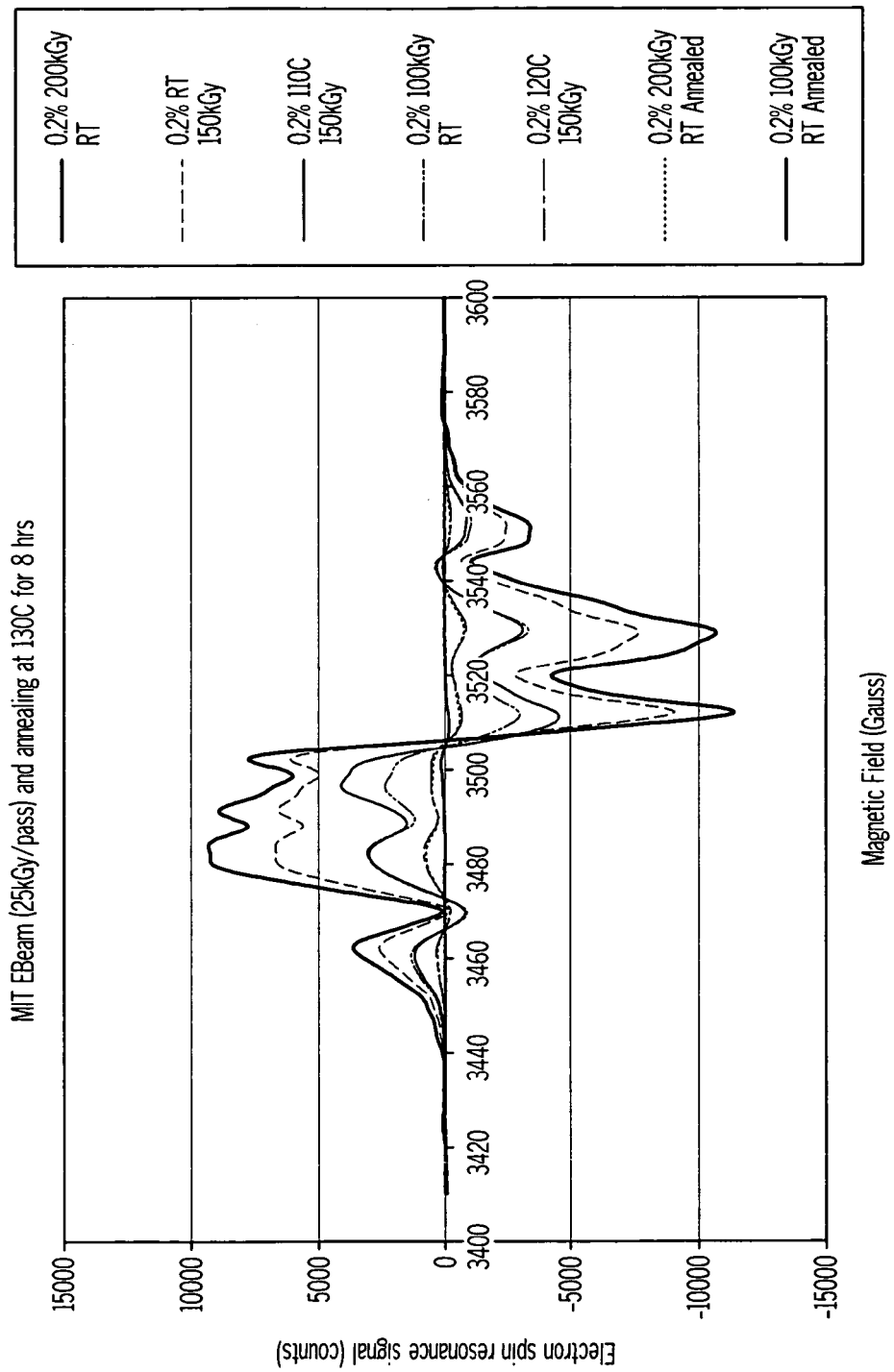
FIG. 6 shows electron spin resonance signal (counts vs. magnetic field (Gauss)) of blends of Vitamin E (0.2 wt %) and UHMWPE powder that were irradiated from 100 to 200 kGy at room temperature, 110° C., and 120° C. after consolidation compared with samples irradiated at 100 and 200 kGy at room temperature, followed by annealing at 130° C. for 8 hours.

The ESR data of the samples of Examples 2 and 3 above were compared (See FIG. 6). FIG. 6 shows electron spin resonance signal of blends of Vitamin E (0.2 wt %) and UHMWPE powder that were irradiated from 100 to 200 kGy at room temperature, 110° C., and 120° C. after consolidation compared with samples irradiated at 100 and 200 kGy at room temperature, followed by annealing at 130° C. for 8 hours (See FIG. 6). The annealing of cold-irradiated blends resulted in better quenching of free radicals than warm irradiation. Therefore, annealing of warm irradiated blends is beneficial as well to further improve the long-term stability of these blends.

Example 5

Long-Term Accelerated Aging of Irradiated Blends—Effect of Annealing

Samples from Example 4 are subjected to accelerated aging according to ASTM F2003-02 (70° C., 5 atm $O_2$ for 2 weeks). Annealed samples have significantly reduced oxidation when compared with unannealed samples.

Example 6

Vitamin-E Diffusion into Irradiated Blends

Samples from Example 3 are soaked in Vitamin E for 2 hours at 120° C. followed by homogenization in argon for 12 days at 130° C. Samples are subjected to accelerated aging according to ASTM F2003-02 (70° C., 5 atm $O_2$ for 2 weeks). Soaked/homogenized samples have reduced oxidation when compared with undoped samples.

Example 7

Room Temperature Mechanical Deformation of Irradiated Blends (i) Samples from Example 3 that were irradiated at room temperature are mechanically deformed at room temperature. Following deformation, the samples are heated to 120° C. to allow the material to recover its shape. Free radical concentrations are measured using ESR and found to be significantly reduced after mechanical deformation. Accelerated aging according to ASTM F2003-02 (70° C., 5 atm $O_2$ for 2 weeks) is performed. Mechanically deformed samples show significantly reduced oxidation compared with undeformed samples.

(ii) Samples from Example 3 that were irradiated at 120° C. are mechanically deformed at room temperature. Following deformation, the samples are heated to 120° C. to allow the material to recover its shape. Free radical concentrations are measured using ESR and found to be significantly reduced after mechanical deformation. Accelerated aging according to ASTM F2003-02 (70° C., 5 atm $O_2$ for 2 weeks) is performed. Mechanically deformed samples show significantly reduced oxidation compared with undeformed samples.

Example 8

Room Temperature Mechanical Deformation of Irradiated Blends Above Room Temperature (i) Samples from Example 3 that were irradiated at room temperature are mechanically deformed at a temperature below the melting point of the formulation. Following deformation, the samples are heated to 120° C. to allow the material to recover its shape. Free radical concentrations are measured using ESR and found to be significantly reduced after mechanical deformation. Accelerated aging according to ASTM F2003-02 (70° C., 5 atm $O_2$ for 2 weeks) is performed. Mechanically deformed samples show significantly reduced oxidation compared with undeformed samples.

(ii) Samples from Example 3 that were irradiated at 120° C. are mechanically deformed at a temperature below the melting point of the formulation. Following deformation, the samples are heated to 120° C. to allow the material to recover its shape. Free radical concentrations are measured using ESR and found to be significantly reduced after mechanical deformation. Accelerated aging according to ASTM F2003-02 (70° C., 5 atm $O_2$ for 2 weeks) is performed. Mechanically deformed samples show significantly reduced oxidation compared with undeformed samples.

Example 9

Blending of Vitamin E-UHMWPE Powder and Virgin UHMWPE Powder 0.2 wt % vitamin-E UHMWPE blended powder is mixed with virgin UHMWPE powder in a 50-50 mixture, followed by consolidation to form vitamin-E deficient regions.

The consolidated material is irradiated with electron-beam or gamma radiation to a dose up to 200 kGy at either room temperature or a temperature below the melting point of the material. The material is then annealed at 120° C. for 100 hours to homogenize the vitamin E in the material. The resultant material shows no measurable residual free radicals as determined by ESR, and exhibits significantly reduced oxidation compared with unstabilized irradiated samples annealed below the melting point.

Example 10

Preparation of UHMWPE/Vitamin E Blends

The UHMWPE vitamin-E blends were prepared by first mechanically blending the UHMWPE powder with vitamin-E and thus forming a high concentration UHMWPE/vitamin E blend. This high concentration blend was then diluted down with virgin UHMWPE powder not containing vitamin E to obtain the desired vitamin-E concentration. The diluted blend was then compression molded into blocks and test samples were machined from these blocks and used in the experiments described below.

Example 11

Figure 7:
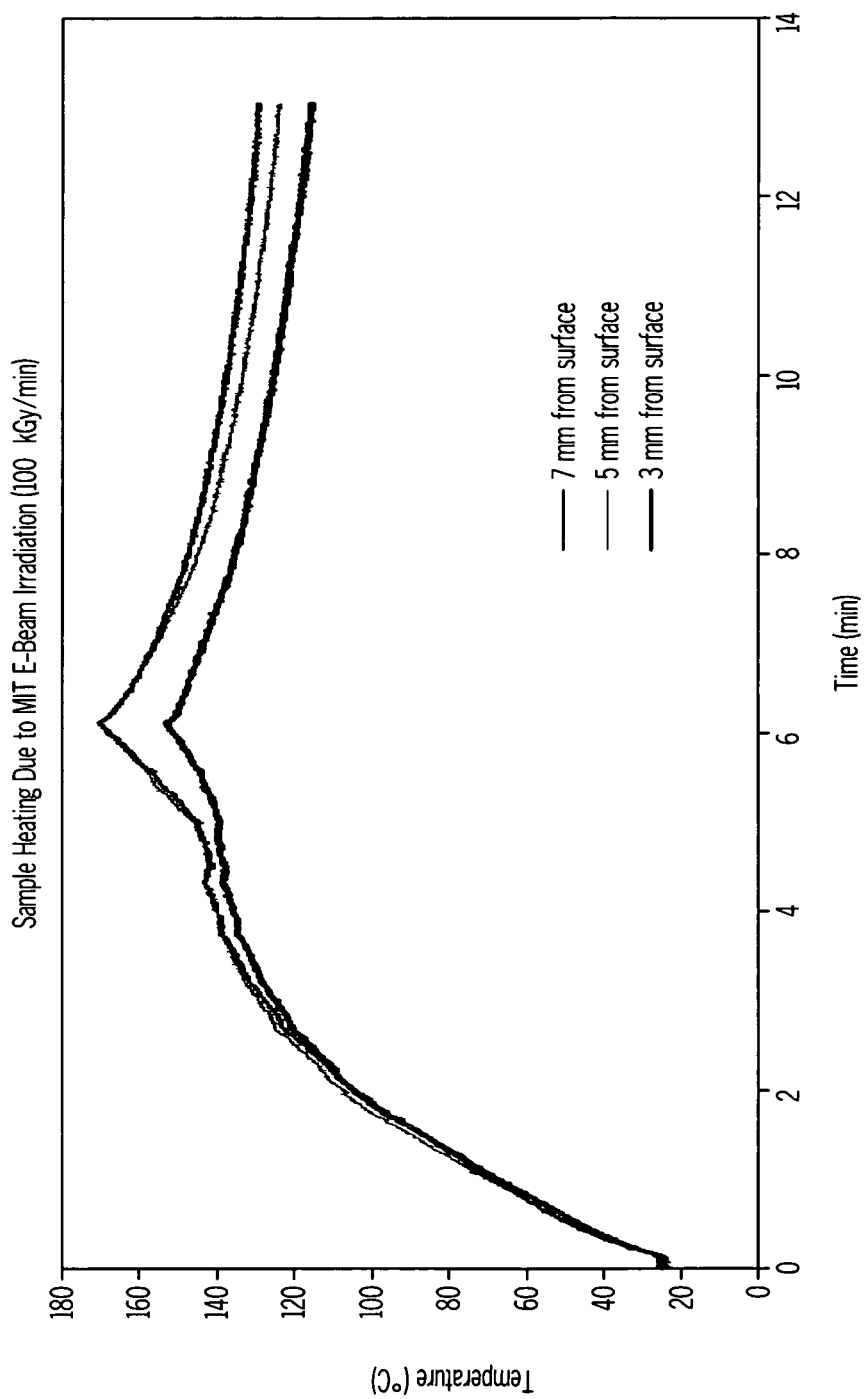
FIG. 7 shows the heating of a polyethylene samples during electron beam irradiation while the polyethylene sample was kept stationary under the beam. Thermocouples were placed at 3, 5, and 7 mm below the e-beam incidence surface.

Adiabatic Temperature Rise in E-Beam Irradiated Blend—Stationery Irradiation with 2.5 MeV 0.2 wt % vitamin E blended GUR 1050 UHMWPE was machined in to a rectangular block of 3 inch×3 inch×1 inch dimensions. Three holes were drilled at 2, 5 and 7 mm away from one of the 3"×3" surfaces, which was indicated as the e-beam incidence surface. Thermocouples were placed in these holes and secured in place with a high temperature tape. The said block was then wrapped in fiberglass insulation first and aluminum foil second. All surfaces were insulated in this manner with the exception of the e-beam incidence surface and real time temperature rise was measured during irradiation. The block was irradiated with a 2.5 MeV Van de Graff e-beam generator with the e-beam incidence surface of the block facing the e-beam. The conveyer belt was not utilized and irradiation was carried out with the block stationary under the beam. The radiation dose rate was about 100 kGy per minute. The temperature increase was recorded using a data acquisition board as a function of time during the irradiation at the three different depths away for the e-beam incidence surface. FIG. 7 shows the temperature rise measured during irradiation. The temperature rise was due to the conversion of e-beam radiation to thermal energy. Note that 1 kGy=1 J/g. Initially the temperature increased linearly following the equation: energy=specific heat×temperature change. Then near 90° C. melting of the polyethylene crystals started to take place slowing down the rate of temperature rise as some of the energy was used for the enthalpy of melting of the crystals. At around 140° C., there was a sharp increase in the rate of temperature rise because the polyethylene in the vicinity of the thermocouples had fully melted and the temperature continued to rise linearly following the equation above but with the specific heat of molten polyethylene, which is lower than that at below 90° C. Also note that the increase in temperature was faster at 5 mm below the e-beam incidence surface where the electrons peaked in their cascade (see example 12). At 3 mm depth the lag in temperature rise was mostly due to heat loss to the surroundings creating less than adiabatic heating. At 7 mm, the radiation generated heating conditions were better, however decline in the electron cascade resulted in a lower radiation dose rate and hence lower temperatures.

Example 12

Figure 8:
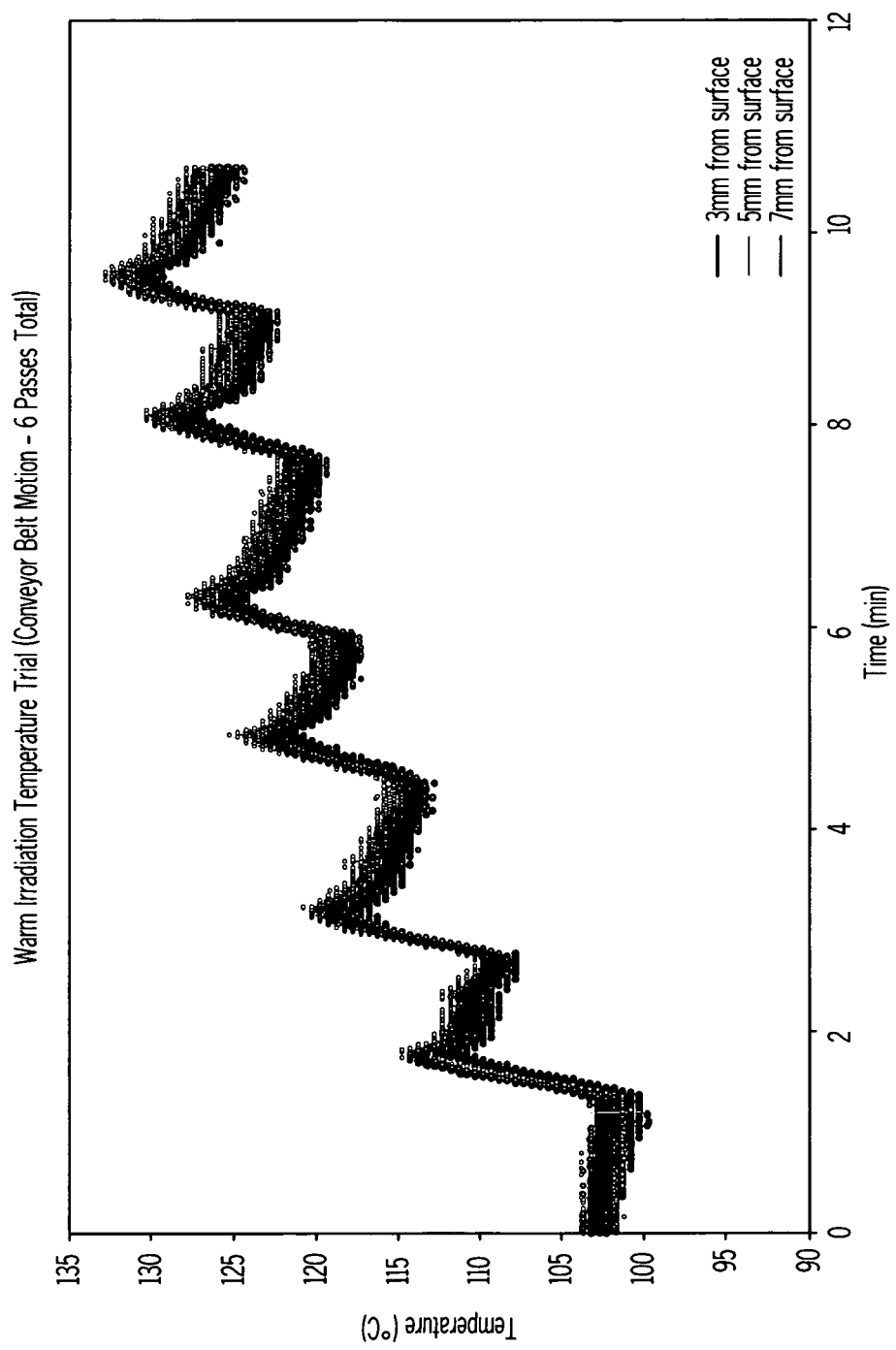
FIG. 8 shows the heating of a polyethylene sample that was irradiated with an electron beam. The irradiation was carried out in 6 passes under the beam and the polyethylene was heated prior to irradiation in a forced convection oven.

Adiabatic Temperature Rise in Cold and Warm E-Beam Irradiated Blend—25 kGy/Pass Irradiation with 2.5 MeV Two blocks (3 inch×3 inch×1 inch) of 0.2 w % UHMWPE/Vitamin E blended stock material was heated to about 100-105° C. in an air convection oven. Thermocouples were placed at 3, 5, and 7 mm from the e-beam incidence surface. The blocks were insulated as described in Example 11 and placed on the conveyor belt for irradiation. The dose rate was 25 kGy per pass. Temperature rise was recorded as a function of time during irradiation. The irradiation lasted for 6 passes for a total of about 250 kGy radiation dose. FIG. 8 shows the temperature rise recorded in both blocks that were instrumented with thermocouples. Temperature of the blocks declined slowly until the blocks reached the beam on the conveyor belt. Under the beam the temperature rise was quite rapid similar to the one described above in the stationary irradiation case. After the blocks passed under the beam the temperature decreased until the blocks returned back to the beam. The largest temperature rise was measured at 5 mm below the e-beam incidence surface where the electron cascade peaked. With additional passes under the beam there was a continued increase in the temperature of the blocks. In certain embodiments the polyethylene is irradiated in one pass and in others in multiple passes. The number of passes and the radiation dose per pass can be adjusted to achieve a desired final temperature in the polyethylene after irradiation.

Example 13

Cold and Warm Irradiation of Blends (2.5 MeV)

Blocks (3 inch×3 inch×1 inch) of Vitamin E/UHMWPE blends were irradiated using the 2.5 MeV Van de Graff generator (HVRL, MIT). The irradiation was carried out at three different temperatures namely room temperature, 110° C., and 120° C. For the room temperature irradiation there were 4 blocks that were machined from the 0.1, 0.2, 0.5 and 1 weight % Vitamin E/UHMWPE blends. At 110° C. irradiation there were 12 blocks as well with the same Vitamin E concentrations as those at room temperature. For both the room temperature irradiation and the 110° C. irradiation one block of each blend was irradiated to 75 kGy, 100 kGy, and 150 kGy. For the 120° C. irradiation the same Vitamin E blended blocks were used. The radiation dose levels for the 120° C. irradiation were 75 kGy, 100 kGy, 150 kGy, 175 kGy, and 200 kGy. The radiation dose rate was 25 kGy/pass. Some of these irradiated blocks were tested for the concentration of residual radicals using electron spin resonance, for the electron beam cascade effect using FTIR, for changes in thermal properties using DSC, and for cross-link density using swelling in hot xylene.

Example 14

Electron Cascade in Irradiated Blends (2.5 MeV)

Fourier Transform Infrared Spectroscopy (FTIR) was used to determine the penetration depth of the electron beam by quantifying the trans-vinylene unsaturation in the 0.5 wt % blend that was irradiated with the 2.5 MeV Van de Graff generator to 150 kGy at room temperature, 110° C., and 120° C. The FTIR also allows the determination of the electron cascade that occurs in the polymer during irradiation. The cascade is due to the increase in the number of secondary electrons that are ejected from the host atoms of the polymer. The generation of the secondary electrons increases the effective absorbed radiation dose resulting in a gradual rise in the effects of radiation in the polymer. With increasing depth, however, the primary electrons loose their energy, which results in a sharp decline in the effective penetration of the electrons.

Trans-vinylene analysis was performed using Fourier Transform Infrared Spectroscopy (FTIR, Bio-Rad FTS2000, Natick Mass.). Thin (~150 µm) sections were cut using a sledge microtome (Model 90-91-1177, LKB-Produkter AB, Bromma, Sweden) and were subsequently sanded on both faces with 400 grit sandpaper (Buehler Ltd., Lake Bluff Ill.) according to ASTM Standard F2381-04. FTIR was then performed on the thin sections. Infrared spectra were collected in depth intervals over the entire thickness. Trans-vinylene levels were quantified as a trans-vinylene index (TVI) calculated by integrating the absorbance over 950 $cm^{-1}$-980 $cm^{-1}$. According to ASTM Standard F2381-04, the integral was normalized to the absorbance over 1330 $cm^{-1}$-1396 $cm^{-1}$.

Figure 9:
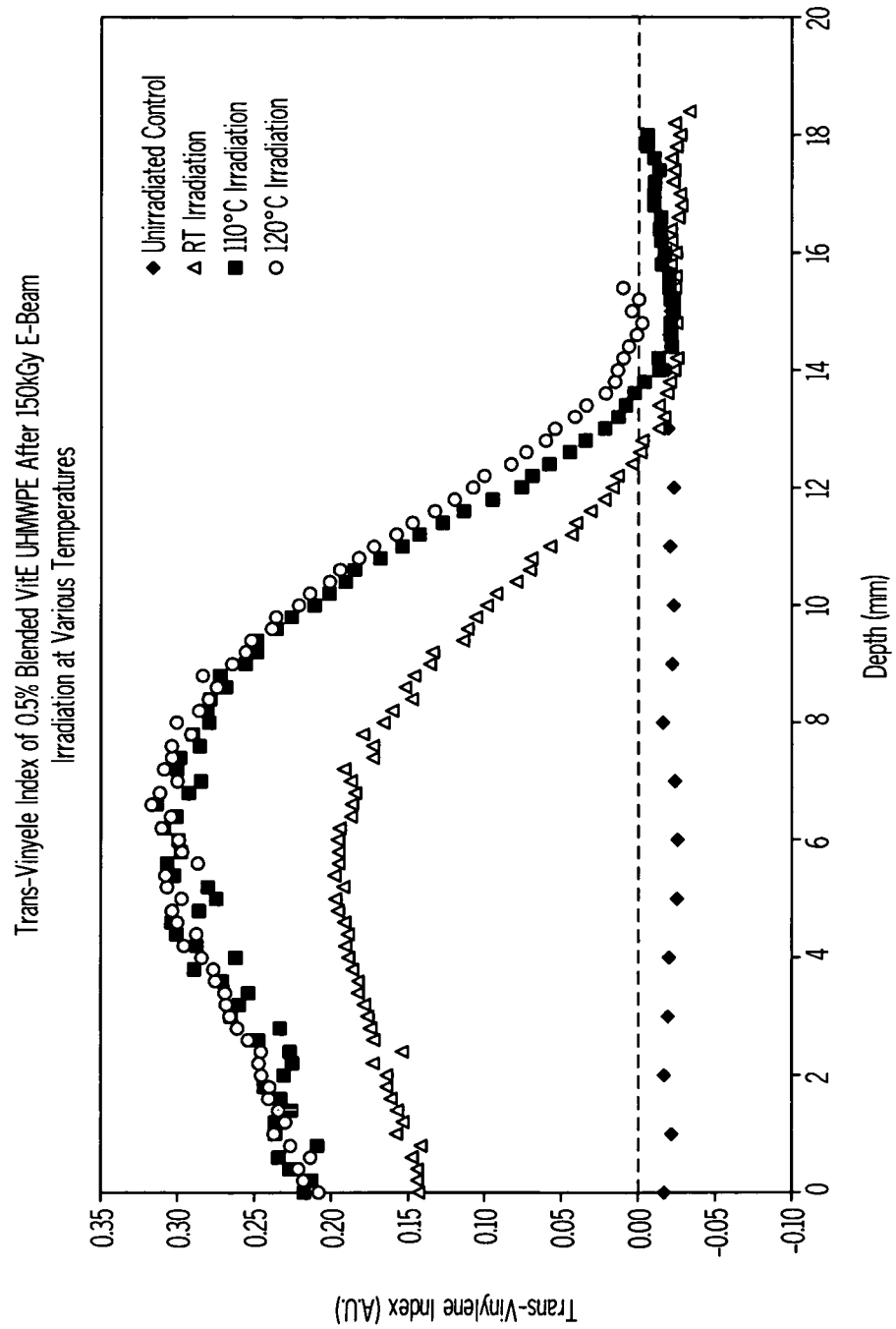
FIG. 9 shows the trans-vinylene unsaturations as a function of depth in 0.5% vitamin E/UHMWPE blend that was either not irradiated or e-beam irradiated to 150 kGy at room temperature (RT), 110° C., and 120° C.

FIG. 9 shows the TVI as a function of depth away from the e-beam incidence surface for the cold and 110° C. and 120° C. irradiated test samples. The cascade effect showed more of a gradient with the elevated temperature than it did with the room temperature irradiation. It also appeared that the warm irradiation provided increased penetration than irradiation at room temperature. There was increased TVI generation with increasing irradiation temperature.

Example 15

Residual Free Radicals in Warm and Cold Irradiated Blends (2.5 MeV)

Figure 10:
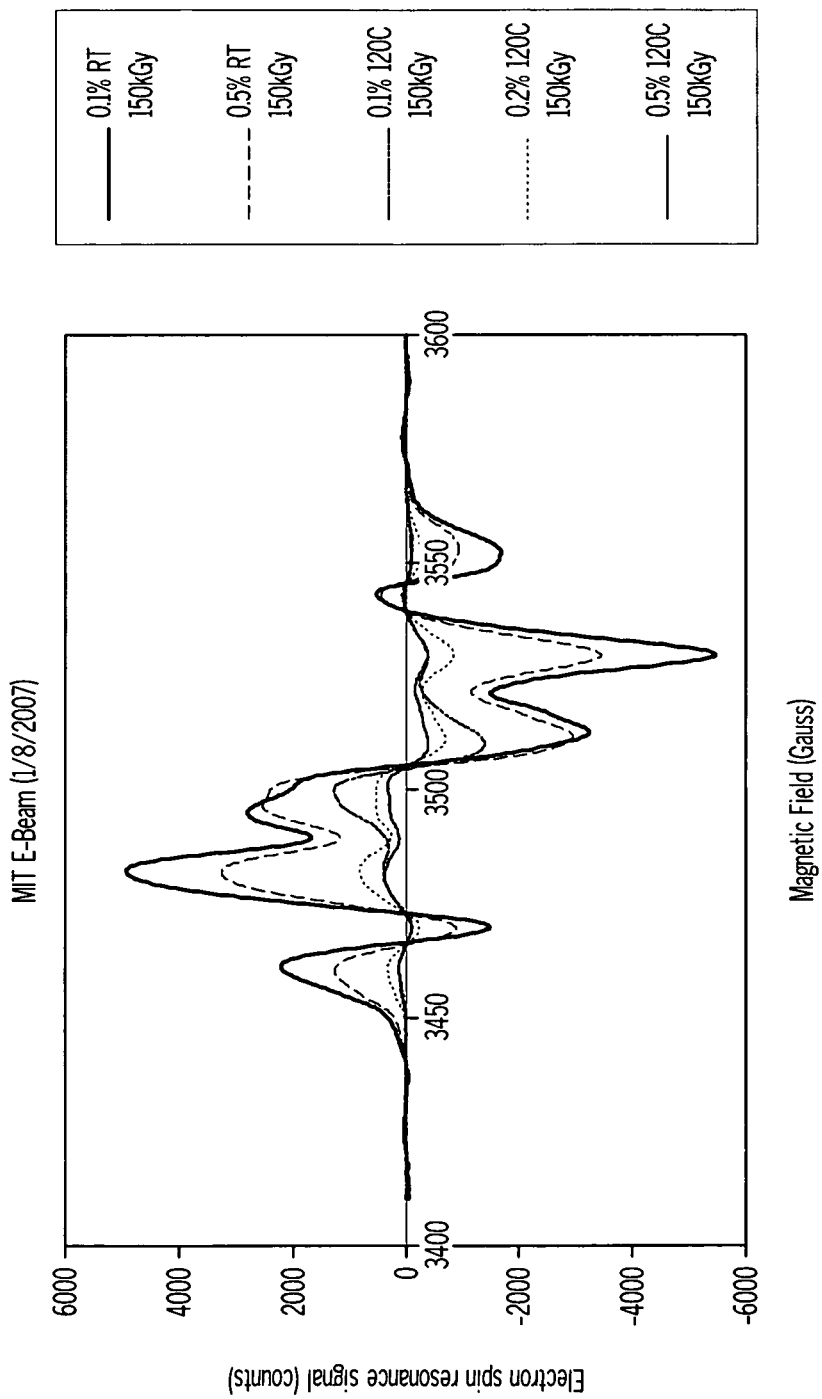
FIG. 10 shows the electron spin resonance (ESR) signal (counts vs. magnetic field (Gauss)) of 0.1, 0.2, and 0.5 wt % vitamin E/UHMWPE blends that were irradiated to 150 kGy at a dose rate of 25 kGy/pass at different temperatures as indicated in the legend. The ESR signal is due to the presence of residual free radicals.

Electron spin resonance of cold and warm irradiated UHMWP/Vitamin E blends were carried out to determine the effect of temperature and the concentration of Vitamin E on the concentration of the residual free radicals. The test samples included a 0.2 wt % blend that was irradiated to 150 kGy at room temperature, at 110° C., and at 120° C., a 0.1 wt % blend that was irradiated to 150 kGy at a room temperature and at 120° C., a 0.5% blend that was irradiated to 150 kGy at room temperature and at 120° C. The irradiation was carried out with the 2.3 MeV Van de Graff generator. The ESR test samples were machined in the form of a rectangular prism of 3 mm×3 mm×20 mm in dimensions. The long axis of ESR samples was within the plane of the e-beam incidence surface and they were approx. 3 to 6 mm below the e-beam incidence surface for all test samples. FIGS. 5 and 10 show the ESR signals recorded from the test samples. Table 2 shows the spin concentrations measured with ESR. With increasing irradiation temperature there was a marked decrease in the ESR signal, which is associated with a decrease in the spin concentration. The increase in the concentration of vitamin E also decreased the concentration of the residual free radicals.

TABLE 2

The spin concentrations measured with ESR.

| Sample ID (Vitamin E concentration; radiation dose; irradiation temperature) | Free Radical Concentration (Spins per gram) |
|---|---|
| 0.2 wt %; 150 kGy; 120° C. | 6.262E+15 |
| 0.2 wt %; 150 kGy; 110° C. | 2.084E+16 |
| 0.2 wt %; 150 kGy;; RT | 8.216E+16 |
| 0.1%; 120 C.; 150 kGy | 4.817E+15 |
| 0.5%; 120 C.; 150 kGy | 4.177E+15 |
| 0.1%; RT; 150 kGy | 4.717E+16 |
| 0.5%; RT; 150 kGy | 3.270E+16 |

Example 16

Thermal Properties of the Warm and Cold Irradiated blends (2.5 MeV)

Differential Scanning Calorimetry (DSC) was used to investigate the thermal properties of some of the irradiated blends. The test samples included the 0.2 wt % blend that was irradiated at room temperature to 250 kGy, 0.2 wt % blend that was irradiated at 110° C. to 100 kGy, 0.2 wt % blend that was irradiated at 120° C. to 150 kGy, 0.2 wt % blend that was irradiated at 120° C. to 17 5 kGy, and 0.2 wt % blend that was irradiated at 110° C. to 150 kGy.

For the DSC analysis the specimens were initially cooled to −20° C. and held at that temperature for 2 minutes. They were then heated to 180° C., subsequently cooled back to −20° C., and reheated to 180° C. Both the heating and cooling segments of this procedure were done at a rate of 10° C./minute. All analyses were based upon the thermogram of the first and second heating segments from −20° C. to 180° C. The peak melting point and the tangential onset melting point were recorded. Crystallinity was quantified by integrating the thermogram from 20° C. to 160° C., and crystallinity was calculated assuming a melting enthalpy of 291 J/g for 100% crystalline UHMWPE.

Figure 11:
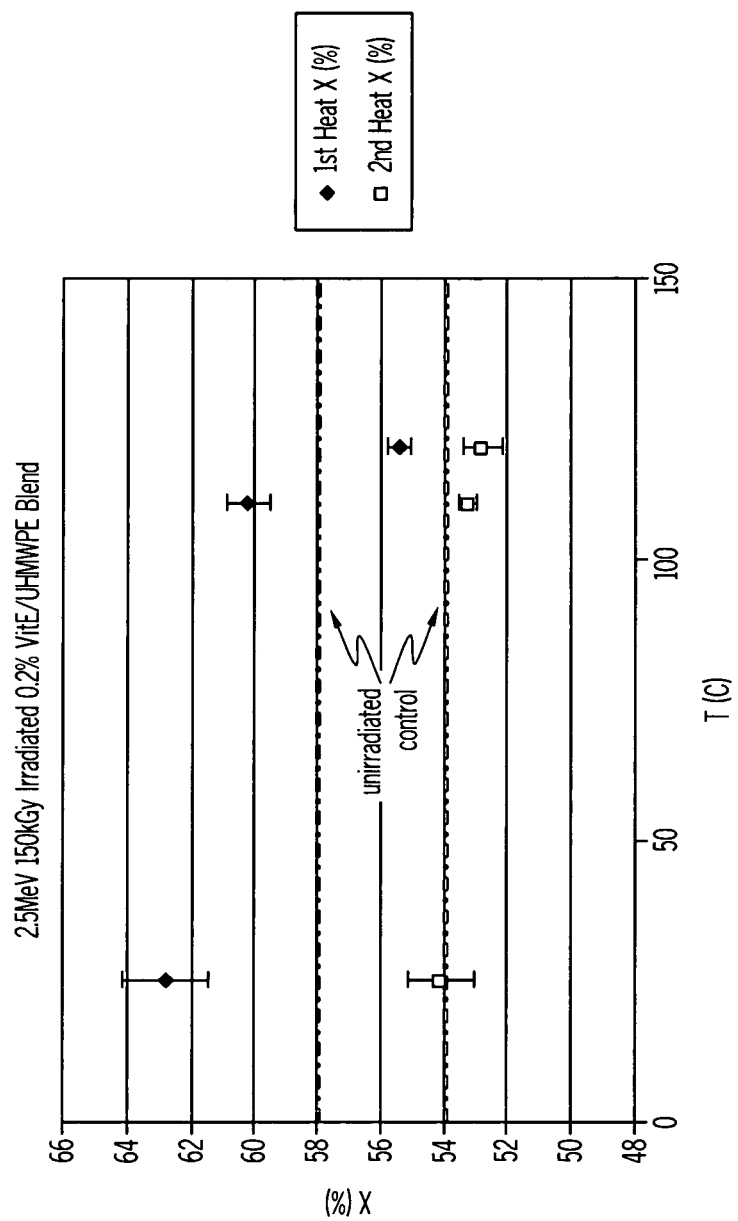
FIG. 11 shows the first heat and second heat DSC crystallinities (X) as a function of radiation dose of 0.2 wt % vitamin E/UHMWPE blend that was irradiated at RT at a dose rate of 25 kGy/pass. Unirradiated control samples are also included for reference.
Figure 12:
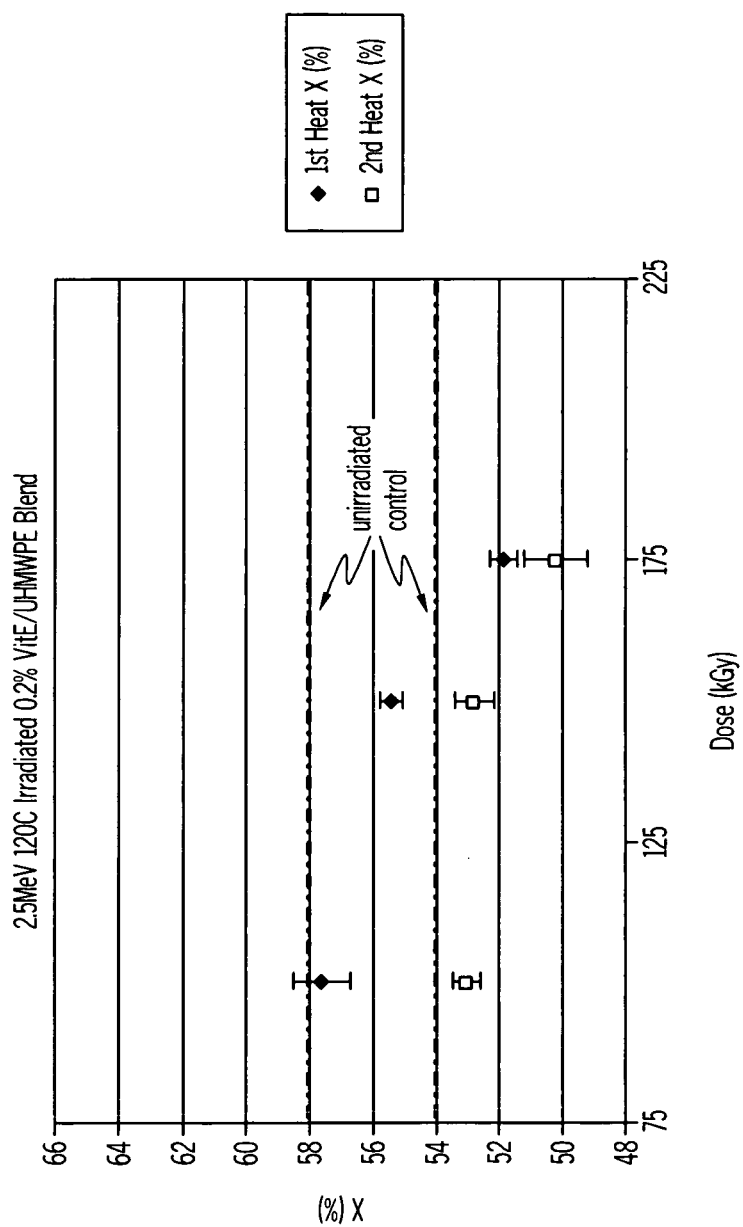
FIG. 12 shows the first heat and second heat DSC crystallinities (X) as a function of radiation dose of 0.2 wt % vitamin E/UHMWPE blend that was irradiated at 120° C. at a dose rate of 25 kGy/pass. Unirradiated control samples are also included for reference.

FIGS. 11 and 12 show the variation in the percent crystallinity (X) measured during the first and second heat DSC. With increasing irradiation temperature the crystallinity declined, which effect was more prominent in the first heat (FIG. 11). The crystallinity also declined with increasing radiation dose when the samples were irradiated at 120° C., with the rate of decline higher with the $1^{st}$ heat than the $2^{nd}$ heat.

Figure 13:
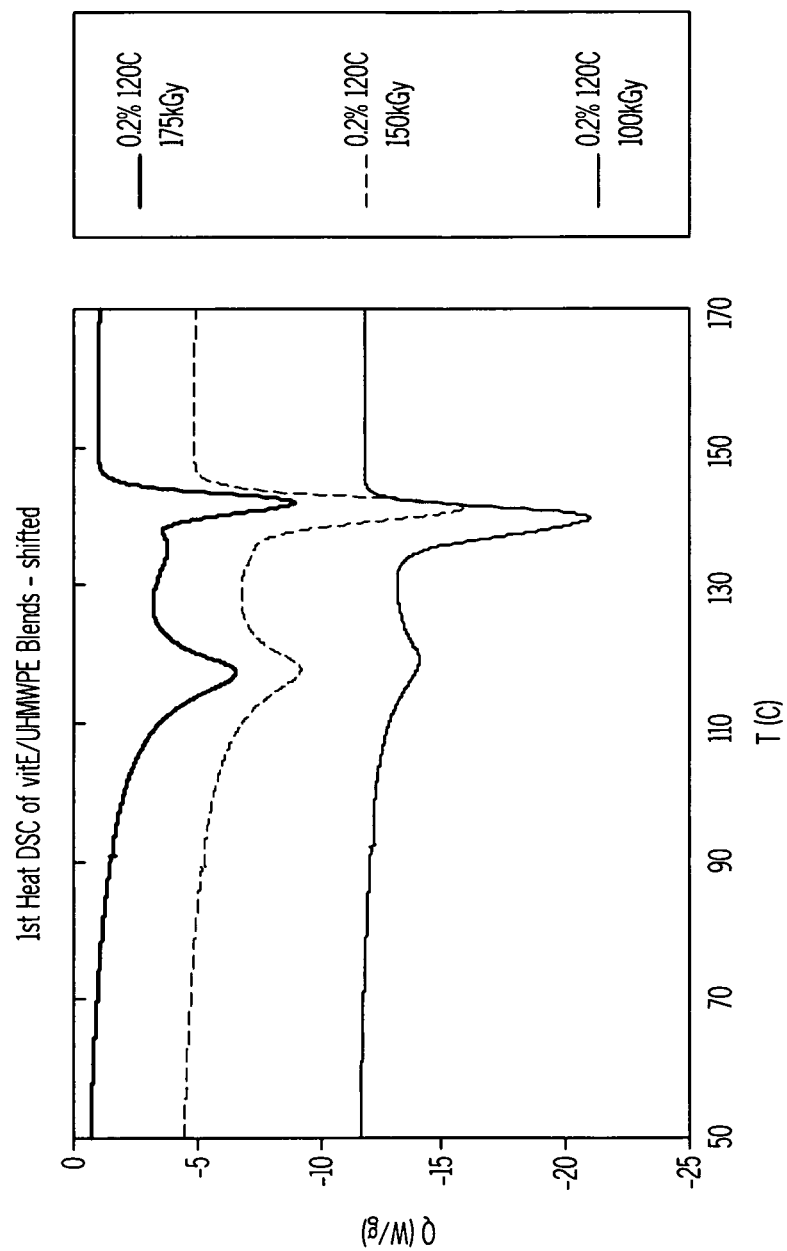
FIG. 13 shows the first heat DSC thermograms of 0.2 wt % vitamin E/UHMWPE blends irradiated at 120° C. to various radiation doses.
Figure 14:
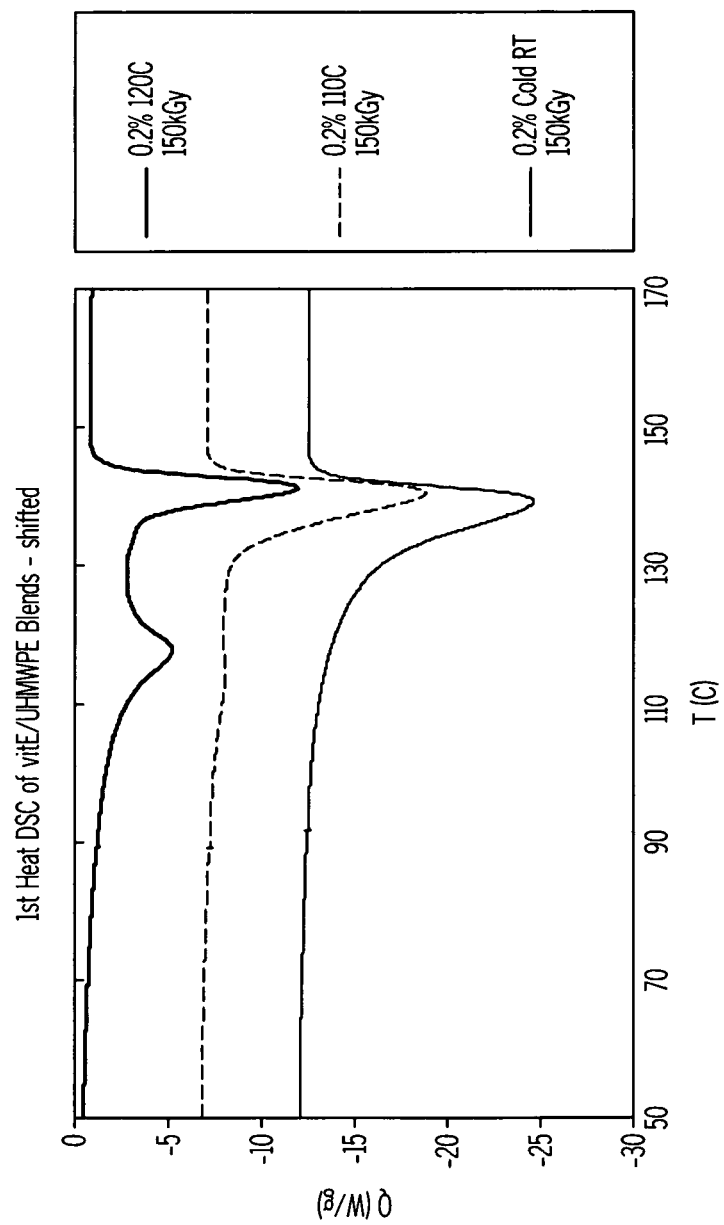
FIG. 14 shows the first heat DSC thermograms of 0.2 wt % vitamin E/UHMWPE blends irradiated to 150 kGy at various temperatures.
Figure 15:
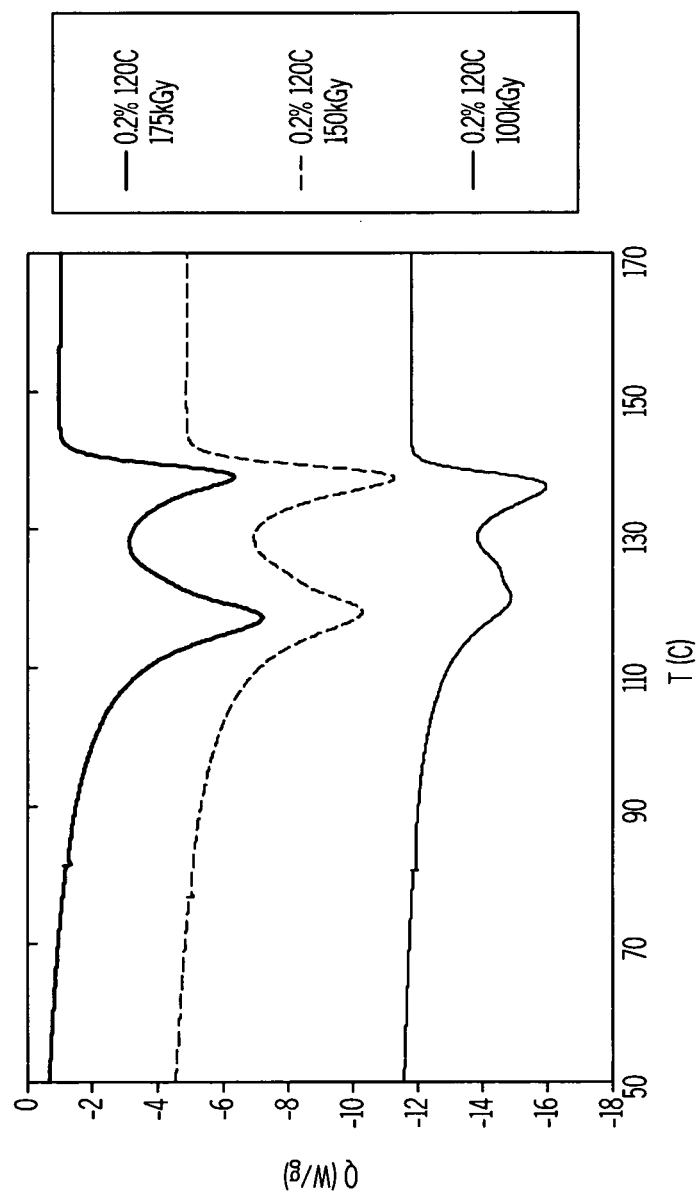
FIG. 15 shows the second heat DSC thermograms of 0.2 wt % vitamin E/UHMWPE blends irradiated at 120° C. to various radiation dose.
Figure 16:
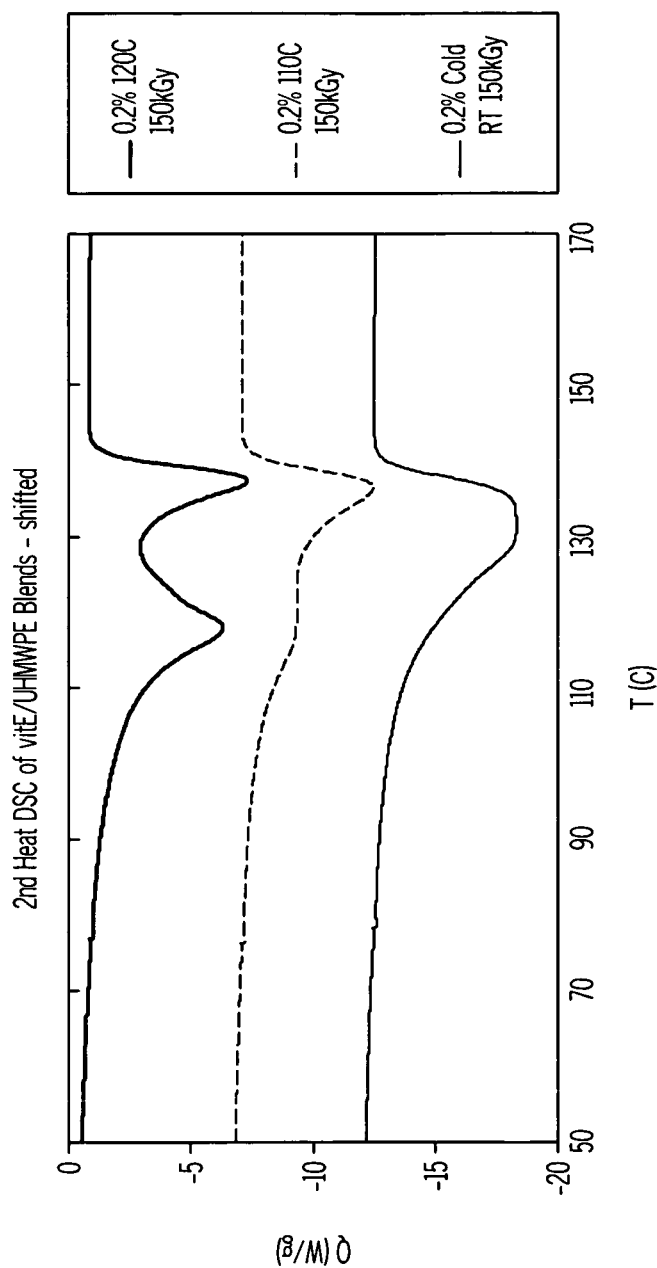
FIG. 16 shows the second heat DSC thermograms of 0.2 wt % vitamin E/UHMWPE blends irradiated to 150 kGy at various temperatures.

FIGS. 13 and 14 show the first heat thermograms and FIGS. 15 and 16 show the second heat thermograms of the test samples studied. With increasing radiation dose the intensity of the lower melting peak increased at the expense of the intensity of the higher melting peak, indicating that population of the higher melting crystals (these would be the thicker crystals) decreased and that these crystals were likely converted to lower melting point crystals. Similarly, with increasing irradiation temperatures the lower melting peak appeared on both the first and second DSC heat thermograms. The height of the lower temperature peak increased with radiation dose. Table 3 lists the peak melting point and crystallinity measured for the first and second heats of irradiated blends as well as the enthalpy of crystallization for the first cool cycle—note that the enthalpy of crystallization was converted to crystallinity by normalizing with 291 J/g.

TABLE 3

Peak melting point and crystallinity measured for the first and second heats of irradiated blends.

| | 1st Heat X (%) | | 1st Cool X (%) | | 2nd Heat X (%) | |
|---|---|---|---|---|---|---|
| | average | stdev | average | stdev | average | stdev |
| T (C.) | | | | | | |
| 25 | 63 | 1.34 | 54 | 1.14 | 54 | 1.05 |
| 110 | 60 | 0.68 | 53 | 0.41 | 53 | 0.26 |
| 120 | 55 | 0.35 | 52 | 0.66 | 53 | 0.64 |
| Dose | | | | | | |
| 100 | 58 | 0.91 | 53 | 0.99 | 53 | 0.44 |
| 150 | 55 | 0.35 | 52 | 0.66 | 53 | 0.64 |
| 175 | 52 | 0.42 | 50 | 0.66 | 50 | 1.03 |

Example 17

The Effect of Cold and Warm Irradiation on Vitamin-e in the blends (2.5 MeV).

FTIR was also used to quantify the changes in the Vitamin E concentration with irradiation by quantifying the Vitamin E absorbance at 1262 cm$^{-1}$. The α-tocopherol concentration profiles were determined using Fourier Transform Infrared Spectroscopy (FTIR, Bio-Rad FTS2000, Natick Mass.). Thin (~150 μm) sections were cut using a sledge microtome (Model 90-91-1177, LKB-Produkter AB, Bromma, Sweden) for analysis. Infrared spectra were collected from one edge of the sample to the other in depth intervals with each spectrum recorded as an average of 32 individual infrared scans. The spectra were analyzed to calculate an α-tocopherol index. The α-tocopherol index was defined as the area under the α-tocopherol absorbance at 1245 cm$^{-1}$-1275 cm$^{-1}$ normalized to the polyethylene skeletal absorbance at 1850 cm$^{-1}$-1985 cm$^{-1}$.

Figure 17:
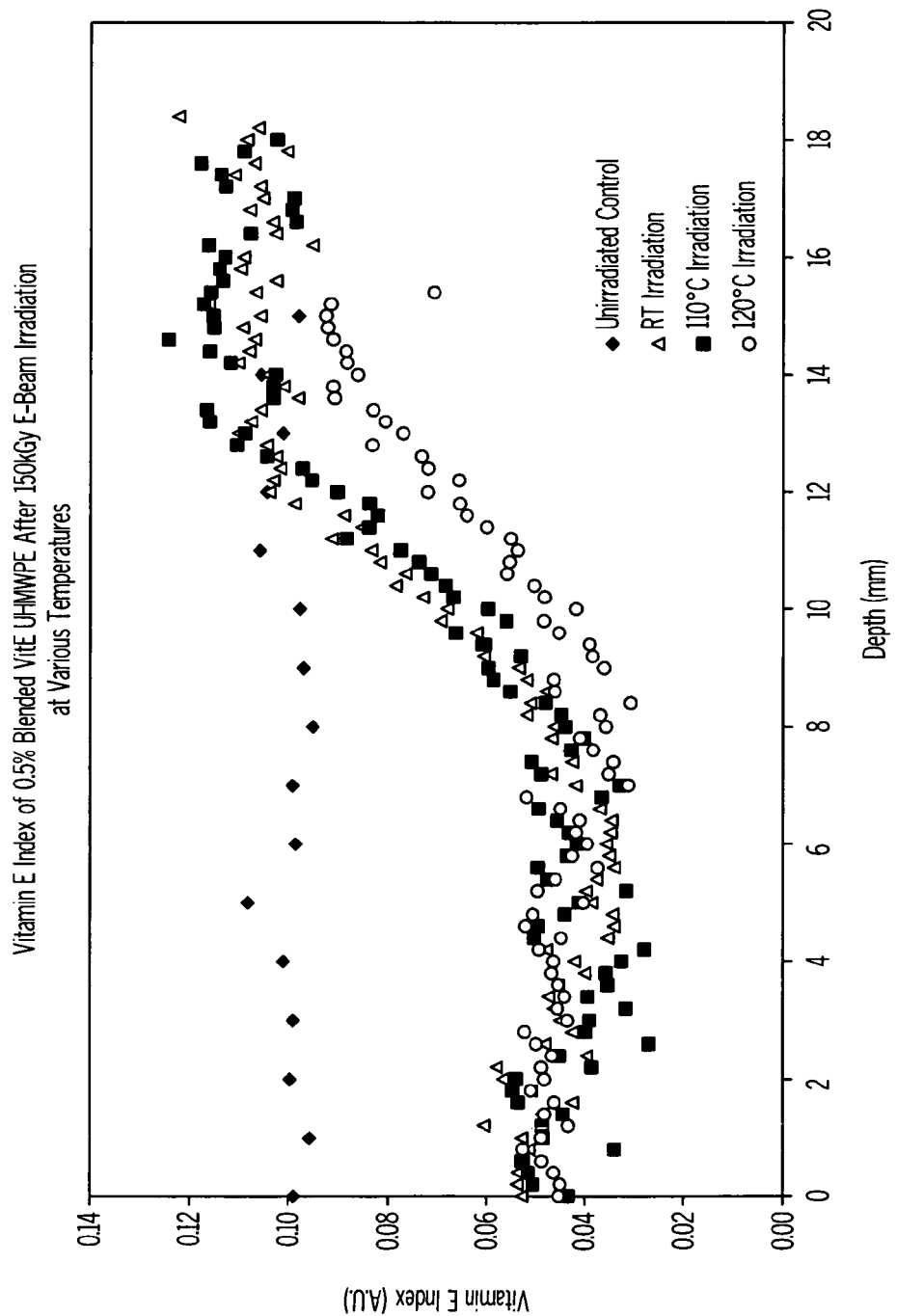
FIG. 17 shows the vitamin E index (a measure of vitamin E concentration) as a function of depth away from e-beam incidence surface of RT, 110° C., and 120° C. irradiated 0.5% vitamin E/UHMWPE blends along with the baseline vitamin E index profile of an unirradiated 0.5% vitamin E/UHMWPE blend sample.

FIG. 17 shows the Vitamin E index as a function of depth away from the e-beam incidence surface. Because the surface was thicker than the full penetration depth of electron beam, we were able to determine the effect of electron beam on the concentration of Vitamin E at different irradiation temperatures. The Vitamin E index profile analysis showed that in the unirradiated portion of the polyethylene, which resided approx. beyond the 1 cm away from the e-beam incidence surface, the Vitamin E index for the 0.5 weight % blends were approx. 0.1. However in the irradiated portions of the blocks the Vitamin E index decreased to a level of about 0.04 and the extent of the decrease was independent of irradiation temperature. Therefore, it seems like the effect of irradiation on the ability of FTIR to detect Vitamin E does not depend on irradiation temperature.

Example 18

Cross-Link Density of Warm and Cold Irradiated blends (2.5 MeV)

Figure 18:
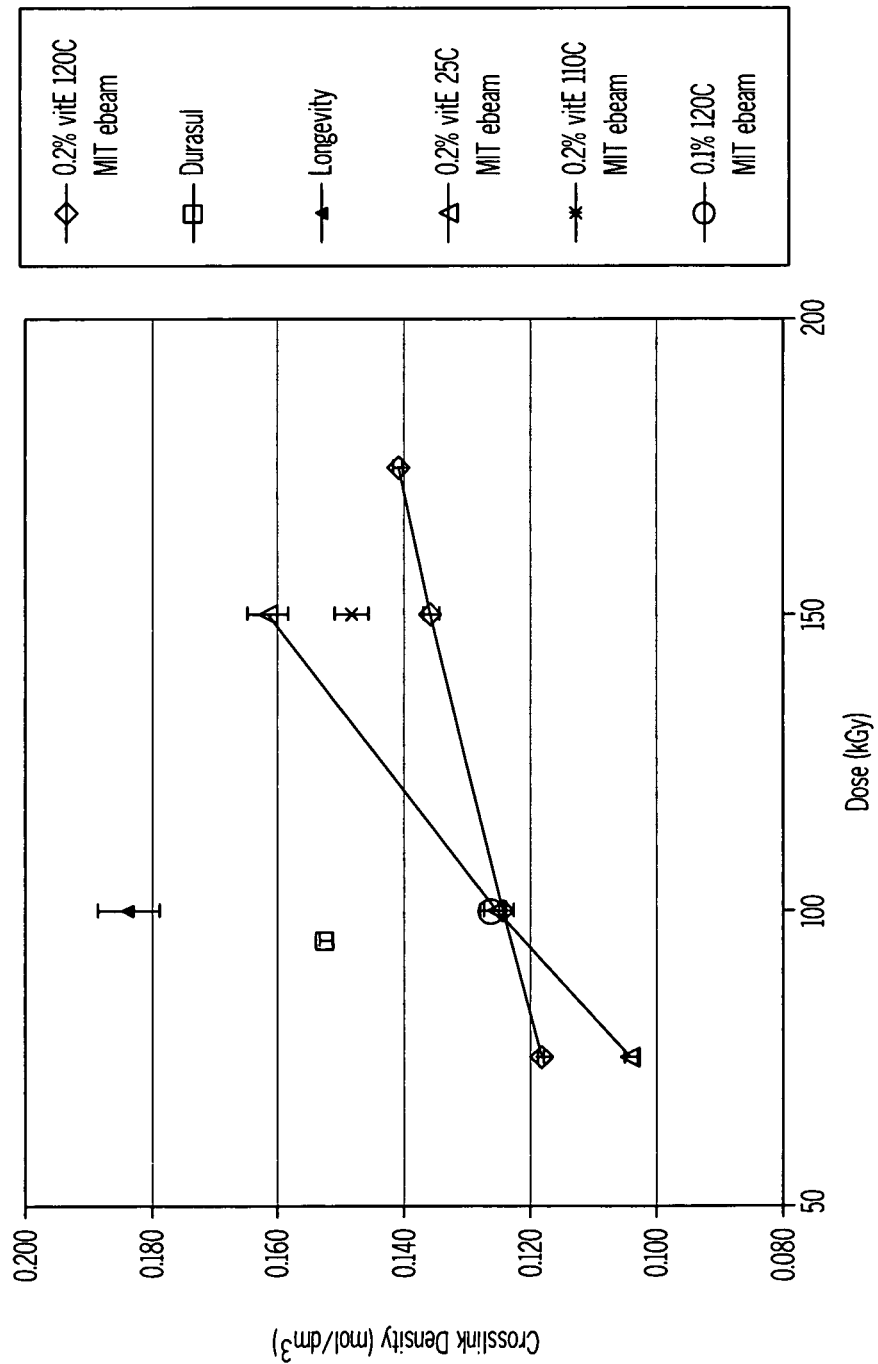
FIG. 18 shows the crosslink density as a function of dose for a variety of radiation cross-linked UHMWPE samples. LONGEVITY was e-beam irradiated at 40° C. to 100 kGy and subsequently melted. DURASUL was e-beam irradiated at 120° C. to 95 kGy and subsequently melted. The irradiation temperature and the vitamin E concentration of the blends are indicated in the legend.

FIG. 18 shows the effect of radiation dose on the crosslink density of different irradiated UHMWPEs. The cross-link density of some of the irradiated blends of UHMWPE/Vitamin E were investigated using hot xylene. Test samples were obtained from 3 to 6 mm below the E-Beam incidence surface of the irradiated blocks. The legend in FIG. 18 lists the test samples included in this investigation. The samples were cut and weighed in a microbalance and then placed in xylene at 130° C. for two hours. The samples were then moved from the hot xylene, blotted on a tissue paper and then immediately placed in a pre-weighed vial that was sealed to prevent evaporation of xylene. The pre-weighed vial was weighed and the weight of the swollen polyethylene test sample was determined. The extent of swelling was determined by calculating the swell ratio (ratio the final volume to the initial volume of the test sample). The density of the polyethylene and the density xylene at 134° C. were used to calculate the final volume of the test samples from the final weight of the test samples. Similarly the initial volume of the test samples was determined by using the density of polyethylene at room temperature. We assume that the density of polyethylene would be approx. 0.99 grams per cm$^3$ at both room temperature and 130° C. The density of xylene at 130° C. was taken to be 0.75 gram per cm$^3$. The swell ratio was used to calculate the cross-link density by using the equation supplied in ASTM F2565. Also included in the swelling experiments were a virgin UHMWPE block that was irradiated at 40° C. to 100 kGy and subsequently melted and the block of virgin UHMWPE that was irradiated at 120° C. to 95 kGy then melted, both irradiation being with election beam.

The virgin UHMWPE swelling experiments showed a higher apparent cross-link density for the samples that were irradiated to 100 kGy at room temperature and subsequently melted (compare LONGEVITY) vs. the one that was irradiated to 95 kGy at 120° C. and subsequently melted (compare DURASUL), even though the radiation dose levels were comparable. This difference in the cross-link density is attributed to the ratio of the H linkages vs. Y linkages that are formed by the cross-linking process. The H linkages are a result of the recombination of two carbon primary free-radicals, which results in a four arm cross-link. The Y linkages are the result of the reaction of a primary carbon free-radical along the backbone of a polyethylene chain with a free-radical that resides at a chain end of another polyethylene molecule resulting in the formation of a three arm cross-link. It has been reported that at elevated temperatures the ratio of Y linkages to H linkages increase during irradiation of ethylene based polymers. A Y linkage restricts the network less than an H linkage, as a result at comparable cross-link densities the swelling of the polymer with more Y linkage is higher than the one with more H linkages. Therefore, the difference between cold and warm irradiation at about the same radiation dose level in terms of apparent cross-link density measure is apparently related to the relative concentrations of H and Y linkages.

The crosslink density with increasing radiation dose level as expected. Surprisingly, the crosslink density of the vitamin E blends were higher when the irradiation was carried out at 120° C. vs. RT at doses above 100 kGy and the opposite was true at doses below 100 kGy. At 150 kGy the crosslink density increased with increasing radiation dose level. With DURASUL and LONGEVITY comparisons (no vitamin E added) the crosslink density was higher with the 120° C. irradiated DURASUL than the 40° C. LONGEVITY. It appears that addition of vitamin E shifts the crossover of the crosslink densities between low temperature and high temperature irradiated samples to higher radiation dose levels.

Example 19

Warm Vs. Cold Irradiated Pure Vitamin E Followed by IR, GC/MS

Pure aliquots of Vitamin E α-tocopherol) are placed in vials under ambient laboratory air conditions (20% oxygen, 79% nitrogen). One set of vials are heated to 120° C., then irradiated with an electron beam source to 100, 150, and 200 kGy. Another set of vials are irradiated at room temperature to the same irradiation doses. The vitamin E samples are then analyzed with infrared spectroscopy and gas chromatography/mass spectroscopy to quantitatively assess the loss of hydroxyl groups on the chroman group of the α-tocopherol as a function of irradiation temperature.

Example 20

Implant Examples

Hybrid implants for orthopedics, dental or other applications can be prepared by consolidating polyethylene powder or flake directly into a porous metal shell or backing. The porous metal backing encourages osseointegration into the implant, providing fixation. UHMWPE flake (GUR 1020 or GUR 1050) blended with Vitamin E according to example 1 can be compression molded into porous metal constructs in the shape of hip, knee, or upper and lower extremities implants. This hybrid system can then be warm irradiated to a dose between 50 and 200 kGy at a temperature below the melting point of the material (less than 140° C.) at a rate that prevents a temperature rise above the melting point of the material during irradiation. An irradiation dose of 150 kGy at a temperature of 100° C. in 1-2 passes under the electron beam can be used. Alternatively, the metal backing can be selectively cooled during irradiation so that while the polyethylene away from the backing rises above the melting point, the polyethylene in contact with the porous metal backing never rises above the melting point. The device can be further annealed below the melt, or used as is following cleaning and sterilization via ionizing radiation, ethylene oxide, or gas plasma.

A similar process can be used for polyethylene implants used in modular systems (locked into metal implants). In this manufacturing process, the vitamin E stabilized polyethylene is molded into a slab, bar, rod, or preform. The material can be warm-irradiated according to the above examples, then machined, or machined prior to warm irradiation. Alternatively, the vitamin E-stabilized polyethylene can be direct compression molded into a final finished shape, then warm-irradiated. The modular implants can be used in hip, knee, and upper and lower extremities.

Example 21

Sequential Irradiation and Annealing of UHMWPE Containing Vitamin E

Puck-shaped UHMWPE (GUR 1050) samples (2.5 in diameter, 1 cm thick) containing Vitamin E with concentrations of 0, 0.01, 0.02, 0.05, 0.1, 0.2, and 0.5 wt % were used. The pucks were subject to e-beam irradiation doses of 100, 150, and 200 kGy. The pucks were annealed at 130° C. for 8 hours in air after each 50 kGy increment of dose. Thus, for example, a 150 kGy irradiated sample was annealed 3 times. The list of samples prepared for the study is shown in Table 4.

TABLE 4

| Sample matrix for the study. | | | | | | | | |
|---|---|---|---|---|---|---|---|---|
| Dose [kGy] | # annealing steps | Vitamin E concentration [wt %] | | | | | | |
| | | 0 | 0.01 | 0.02 | 0.05 | 0.1 | 0.2 | 0.5 |
| Samples | | | | | | | | |
| 100 | 2 | • | • | • | • | • | • | • |
| 150 | 3 | • | • | • | • | • | • | • |
| 200 | 4 | • | • | • | • | • | • | • |
| 200 | 2 | | | | | • | | |
| Controls | | | | | | | | |
| 100 | 1 | • | | | | • | | |
| 100 | 2 | • | | | | | | |
| 100 | 0 | • | | | | • | | |

The crosslink density of the samples was determined gravimetrically by swelling in xylene at 130° C. The values of the crosslink density are plotted in FIG. 19. The data show the decrease in crosslink density with decreased dose and increased vitamin E content. Although there appears to be a slight increase in crosslink density with increasing vitamin E content at low vitamin E concentrations (0.01 to 0.02 wt %), these differences were not statistically significant.

Figure 19:
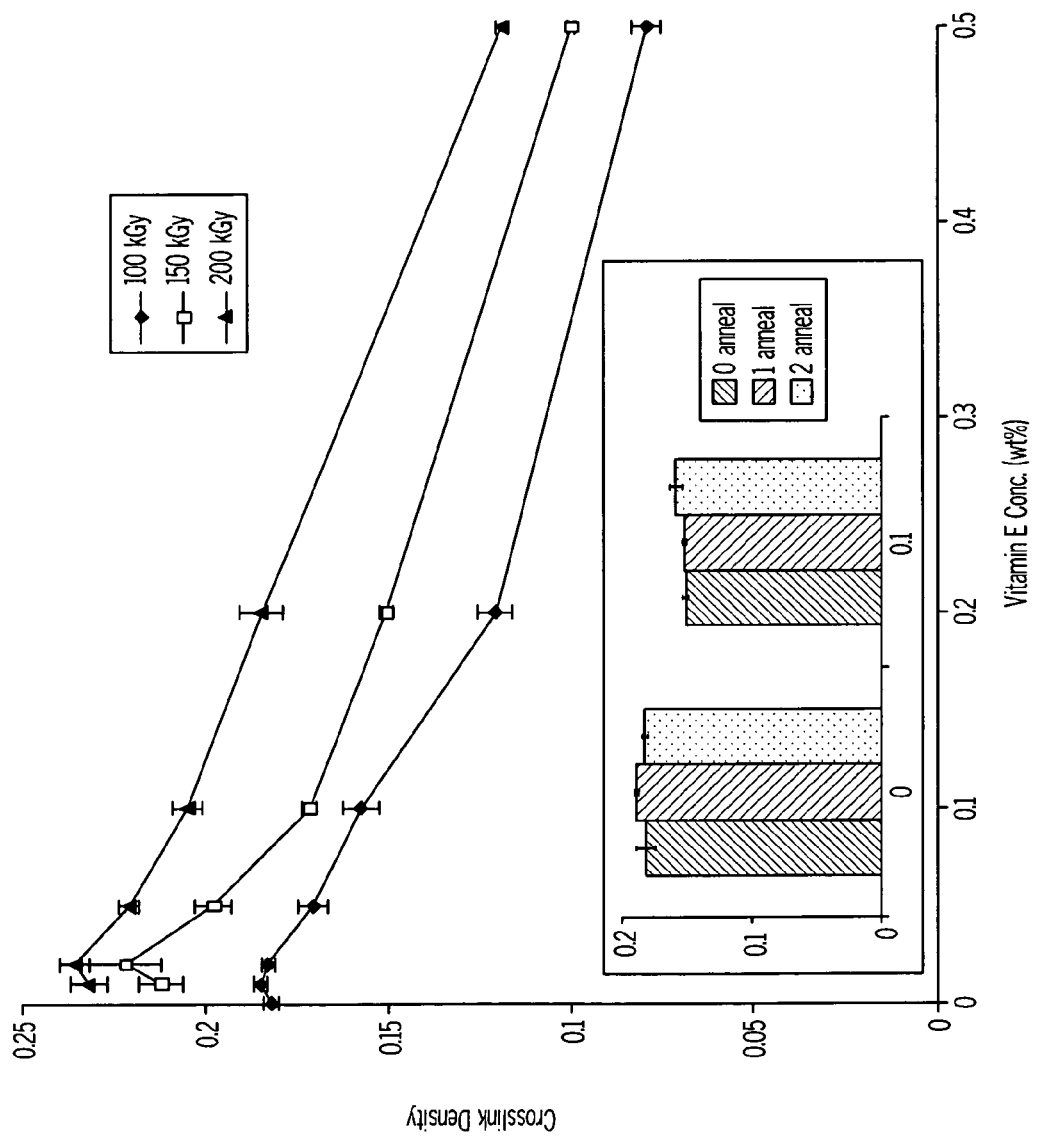
FIG. 19 shows crosslink density of samples from E″ sequential annealing study. All samples were annealed after each 50 kGy of e-beam dose applied. In the inset, a plot is shown for samples subjected to different numbers of annealing steps but with the same overall irradiation dose of 100 kGy. Two sample sets, one for samples containing no vitamin E and one for samples containing 0.1 wt % vitamin-E were tested.

In the inset to FIG. 19, the effect of annealing on the crosslink density for samples containing 0 and 0.1 wt % vitamin E is shown. These samples were irradiated to 100 kGy and subsequently annealed 0, 1, and 2 times. The samples annealed twice were annealed first after 50 kGy of dose, and again after the remaining 50 kGy of dose. The sample annealed once was annealed after the full 100 kGy of dose was applied. From these data no significant difference in crosslink density within either the virgin or 0.1 wt % sample sets is observed. Therefore, annealing appears to have a negligible effect on crosslink density.

Figure 20A:
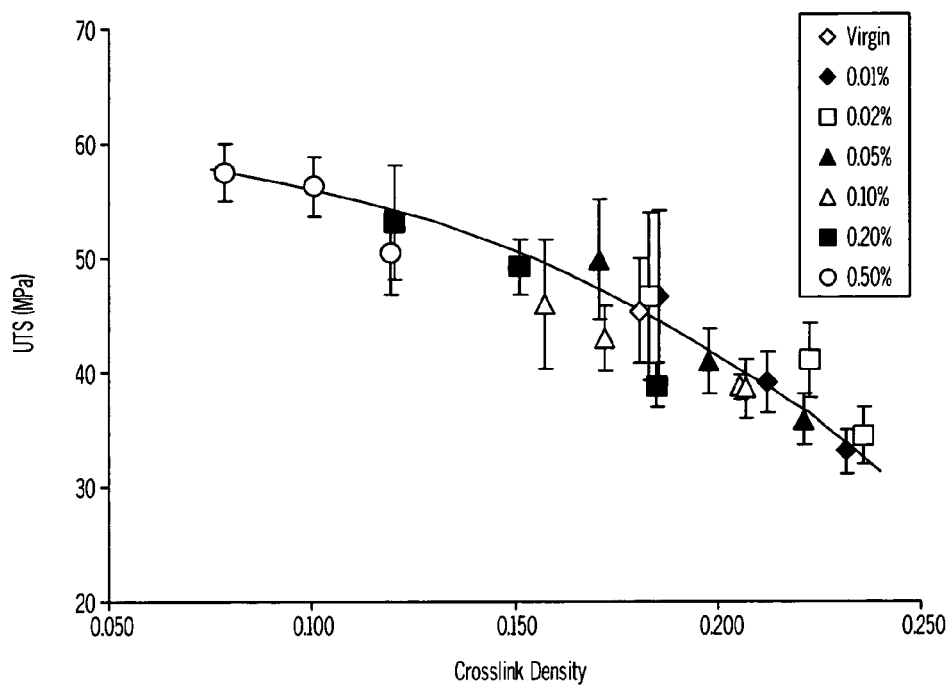
FIG. 20 (A & B) illustrates tensile properties of samples from the sequential irradiation/annealing study. Samples were annealed after each 50 kGy of dose. Both (20A) Ultimate Tensile Strength and (20B) Elongation at break are plotted as a function of crosslink density.
Figure 20B:
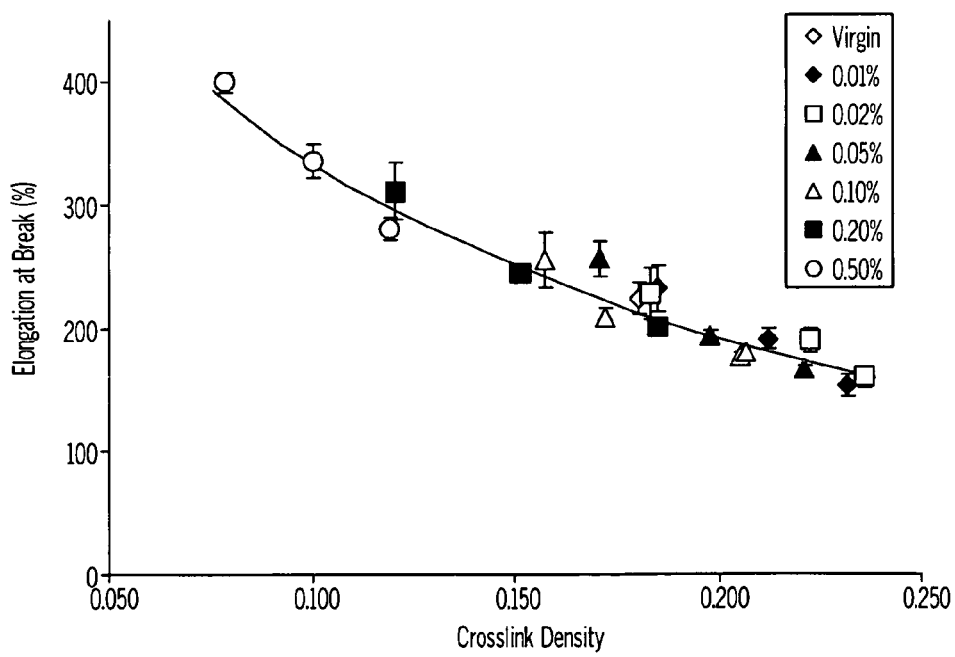

In FIGS. 20A and 20B show the ultimate tensile strength (UTS) and the elongation at break as a function of crosslink density for samples subjected to sequential irradiation and annealing. Both the UTS and the elongation data decrease with increasing crosslink density, which is expected. Interestingly, the UTS data follows a general trend with all data points falling essentially on the same trend-line. The elongation data follows its own distinct trend, with all data points again following it quite closely. This suggests that at a given crosslink density, similar mechanical properties can be expected, regardless of vitamin E concentration, number of annealing steps, and total irradiation dose.

Example 22

Cold Irradiation Followed by Warm Irradiation of Vitamin E/UHMWPE Blends

Rationale—This study was carried out to see if the mechanical properties of UHMWPE/vitamin-E blends would be affected by cold irradiation followed by warm irradiation. The benefit of cold irradiation followed by warm irradiation would be to avoid overheating relating cracking of UHMWPE bars during warm e-beam irradiation when the dose level is high—with this method one would administer some of the dose at cold temperatures (lower than 100° C.) ahead of time so that the remaining dose does not cause cracking when administered at an elevated temperature (above room temperature).

UHMWPE blended with 0.15 and 0.3 wt % vitamin E were used. Approximately 1 cm-thick blocks of these vitamin E-blended UHMWPE were irradiated at room temperature first, followed by heating in a convection oven to 100° C. for at least 18 hours and irradiating at this temperature. The total dose that the samples received was 175 kGy; the cold irradiation dose was increased at 25 kGy intervals. Electron beam irradiation (2.5 MeV) at 25 kGy/pass was used. Thin sections (3.2 mm) were machined from the irradiated blocks and dog-bones were stamped from these thin sections. Tensile mechanical testing, cross-link density measurements (by swelling in xylene) and crystallinity measurements (differential scanning calorimetry) were performed.

Figure 21:
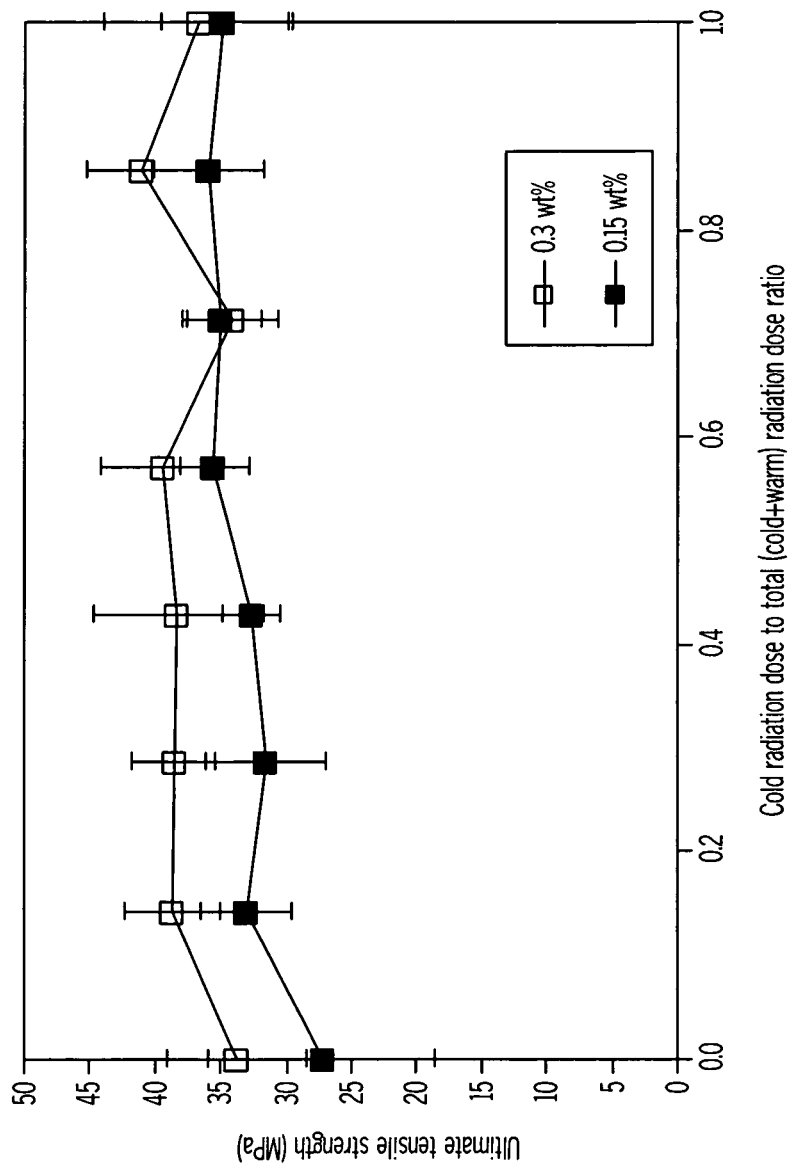
FIG. 21 shows ultimate tensile strength (UTS) of vitamin E/UHMWPE blends irradiated by cold irradiation followed by warm irradiation to a total dose of 175 kGy. The x-axis is the ratio of radiation dose applied cold to the total radiation dose applied cold and warm.
Figure 22:
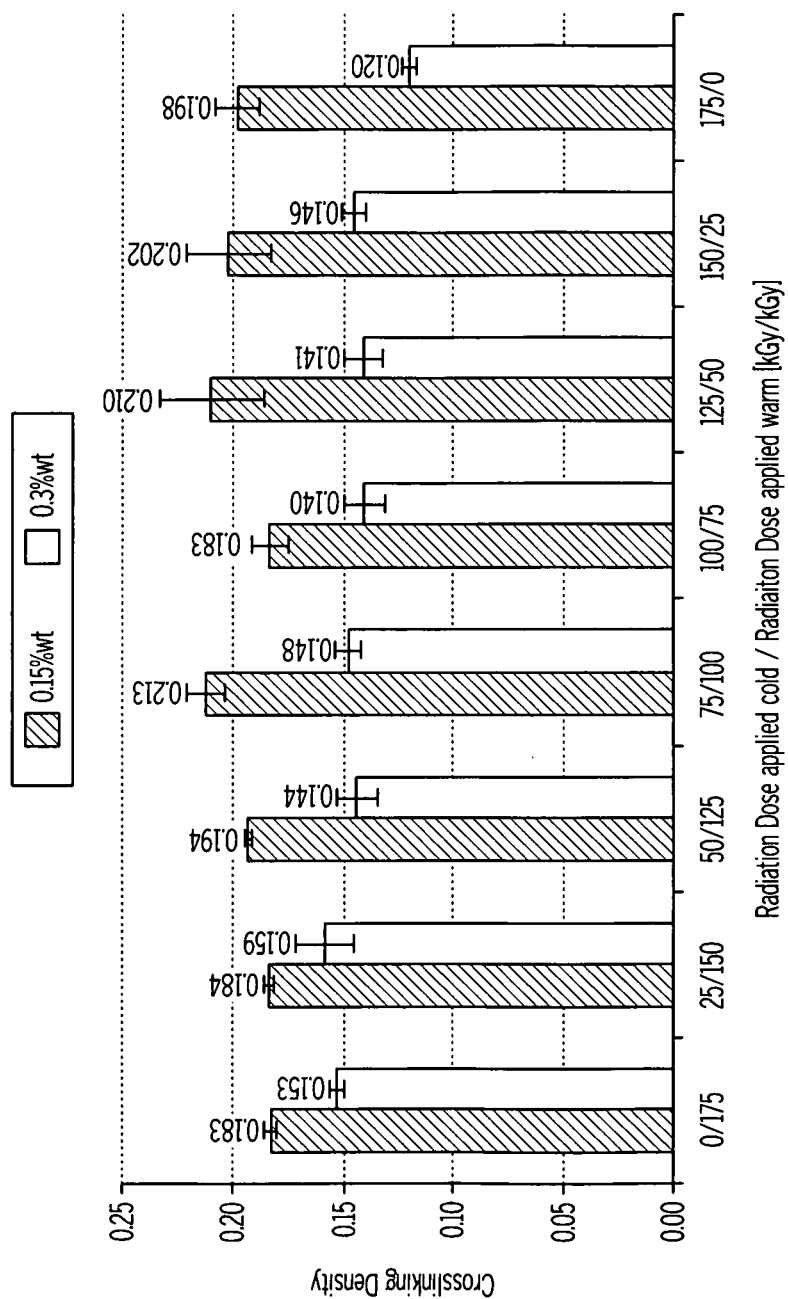
FIG. 22 shows crosslink density (mol/dm$^3$) of vitamin E/UHMWPE blends irradiated by cold irradiation followed by warm irradiation to a total dose of 175 kGy.

The UTS of the vitamin E/UHMWPE blends that were cold irradiated followed by warm irradiation were slightly lower compared to the 175-kGy cold irradiated UHMWPE and slightly higher than the 175-kGy warm irradiated UHMWPE despite no significant differences (FIG. 21). The UTS of 0.3 wt % vitamin E-blended and subsequently irradiated UHMWPE was significantly higher than the 0.15 wt % blend (FIG. 22). The crosslink density of the 0.15 wt % blend subsequently irradiated to 175 kGy did not show a significant trend as a function of increasing cold irradiation dose. The crosslink density was comparable to previously obtained results for un-melted LONGEVITY using the same method. Therefore, the wear resistance is expected to be high. The elongation-to-break (EAB) decreased gradually when the cold irradiation dose was increased, suggesting that some benefit may be gained by performing terminal warm irradiation to minimize loss of mechanical properties.

Example 23

Effect of Post-Irradiation Annealing on the Oxidative Stability of Vitamin E-UHMWPE Blends Blocks of GUR 1050 containing 0.01, 0.02, and 0.05 wt % vitamin E were irradiated to 100 kGy using a 3 MeV electron beam. One half of each block was annealed at 130° C. for 8 hours, the other half was unannealed. Portions of both the annealed and the unannealed samples were aged according to a modified protocol based on ASTM F2003-02 (5 atm $O_2$ for 4 weeks at 70° C.).

Figure 23:
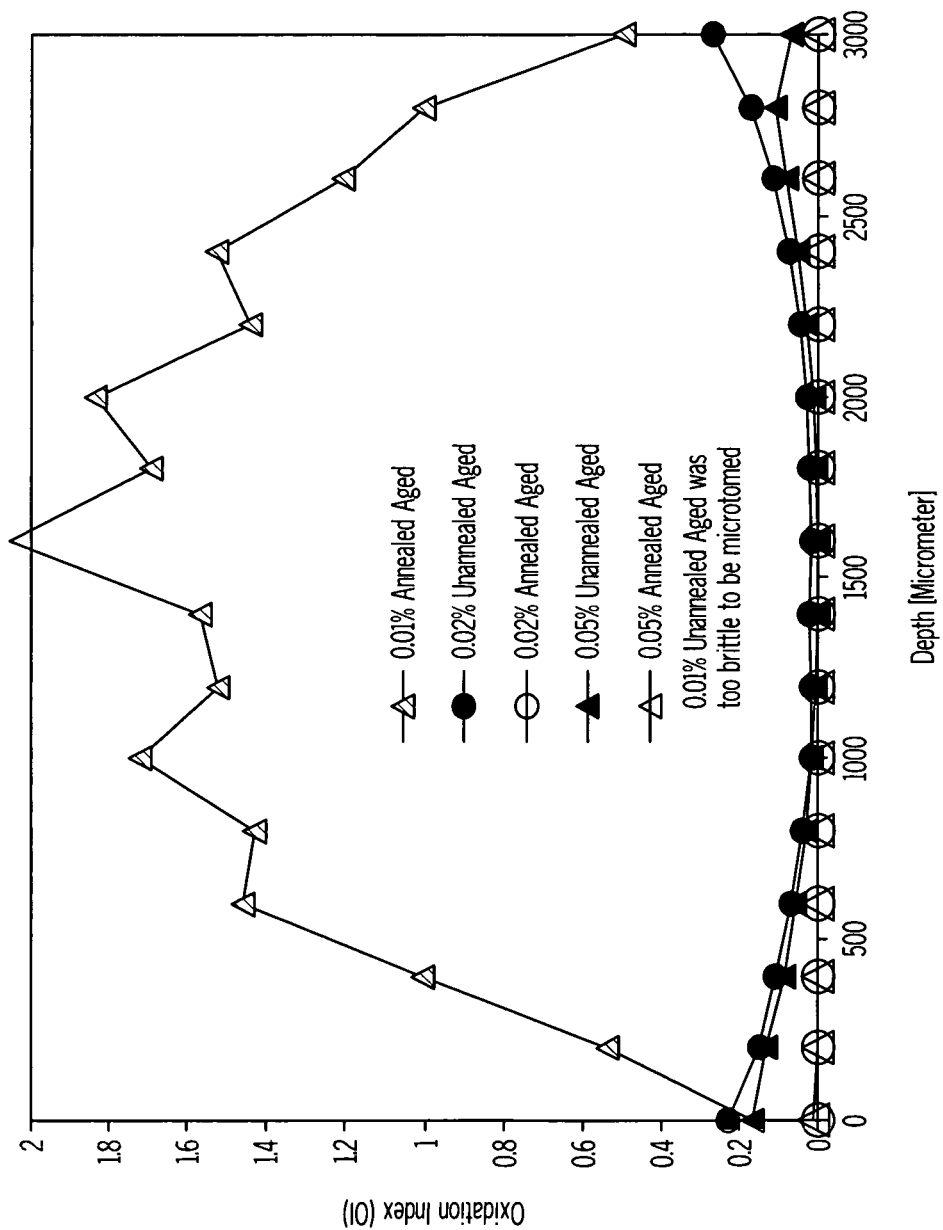
FIG. 23 depicts oxidation index of annealed and unannealed samples subjected to accelerated aging.

The values of the oxidation index (OI) measured in FTIR for aged samples are shown in FIG. 23. The calculation for the OI was taken as the ratio of the peak at 1740 $cm^{-1}$ to the reference peak at 1370 $cm^{-1}$. The 0.01% Annealed Aged sample had significantly higher OI values than the other samples plotted. Data could not be obtained for the 0.01% Unannealed Aged sample because it was too brittle to microtome, indicating that it suffered the most significant oxidation of all the samples. The 0.02 wt % and 0.05 wt % Unannealed Aged samples both had relatively low (<0.25) but measureable surface OI values after 4 weeks aging, while the 0.02 wt % and 0.05 wt % Annealed Aged samples showed no measureable oxidation, indicating that annealing had improved their oxidation resistance.

The tensile properties of all samples are reported in Table 5. For a given vitamin E concentration, there are no statistically significant differences between the Annealed and Unannealed samples before aging. This indicates that annealing by itself does not have a measureable effect on the mechanical properties of UHMWPE Vitamin E blends.

TABLE 5

Tensile properties of annealed and unannealed samples, both aged and unaged.

| Vitamin E conc. (wt %) | | | UTS (MPa) | +/− | Yield (MPa) | +/− | Elongation (%) | +/− |
|---|---|---|---|---|---|---|---|---|
| 0.01 | Unannealed | Unaged | 46.1 | 5.2 | 25.1 | 0.4 | 275 | 18 |
| 0.01 | Annealed | Unaged | 47.1 | 2.6 | 25.1 | 0.5 | 275 | 18 |
| 0.01 | Unannealed | Aged | 0 | 0 | 0 | 0 | 0 | 0 |
| 0.01 | Annealed | Aged | 20.2 | 7.5 | 22.2 | 8.6 | 61 | 96 |
| 0.02 | Unannealed | Unaged | 49.2 | 2.3 | 25.2 | 0.5 | 298 | 16 |
| 0.02 | Annealed | Unaged | 47.1 | 3.5 | 24.1 | 0.7 | 271 | 25 |
| 0.02 | Unannealed | Aged | 42.8 | 1.6 | 24.7 | 0.4 | 264 | 5 |
| 0.02 | Annealed | Aged | 47.7 | 4.6 | 24.2 | 0.8 | 266 | 15 |
| 0.05 | Unannealed | Unaged | 43.4 | 5.2 | 23.5 | 1.6 | 284 | 25 |
| 0.05 | Annealed | Unaged | 47.4 | 2.8 | 24.4 | 0.6 | 279 | 11 |
| 0.05 | Unannealed | Aged | 44.6 | 3.3 | 24.1 | 0.7 | 283 | 8 |
| 0.05 | Annealed | Aged | 49.4 | 1 | 25 | 0.3 | 282 | 6 |

After aging, there is a significant reduction in the mechanical properties of the 0.01 wt % blends (both annealed and unannealed), consistent with the OI data. The highly oxidized 0.01% Annealed Aged sample showed lower mechanical properties, however the 0.01 wt % Unannealed Aged sample was too brittle to be tested at all—therefore annealing had a protective effect with the irradiated 0.01% blends. The 0.02 wt % and 0.05 wt % samples did not show such strong reductions in properties, which is not surprising given that their OI values never exceeded 0.25. However, there are subtle reductions in mechanical properties in the 0.02 wt % samples. For example, the ultimate tensile strength (UTS) and the elongation of the 0.02% Unannealed Aged samples were lower than the Unannealed Unaged samples. However, there was no such decrease in mechanical properties in the 0.02% Annealed Aged samples relative to the 0.02% Annealed Unaged samples. There were also no significant decreases in mechanical properties in either the 0.05% Unannealed Aged samples or the 0.05% Annealed Aged samples relative to their unaged counterparts.

From the mechanical properties results it can be seen that the lowest acceptable vitamin E concentration for an unannealed material, at this radiation dose of 100 kGy, is 0.05 wt %, given that the next lowest concentration, 0.02%, had reduced mechanical properties after aging when unannealed. However, for an annealed material, the lowest acceptable vitamin E concentration is 0.02 wt %, because there was no significant reduction in mechanical properties at a concentration of 0.02% when the samples were annealed. Therefore, an important benefit of annealing is that it allows the use of a lower vitamin E concentration, which in turn allows a lower radiation dose to be used during processing.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

What is claimed is:

1. A method of making highly cross-linked, oxidatively stable, and highly crystalline polymeric material comprising:
   a) blending antioxidant with UHMWPE resin, powder, or flake in the absence of a supercritical fluid, thereby providing a polymeric blend, wherein the blend is mixed with virgin UHMWPE resin, powder, or flake, thereby forming a composition having antioxidant rich and poor regions;
   b) consolidating the blend from step (a) to provide a consolidated polymeric material having antioxidant rich and poor regions;
   c) irradiating the consolidated polymeric material from step (b) at a temperature that is above the room temperature and below the melting point of the polymeric material to provide an irradiated and consolidated polymeric material having antioxidant rich and poor regions; and
   d) annealing the irradiated and consolidated polymeric material in air or under an inert environment at a temperature below the melting temperature of the polymeric material, thereby forming a highly cross-linked, oxidatively stable, and highly crystalline polymeric material.

2. The method according to claim 1, wherein the crystallinity of the polymeric material is greater than about 51%.

3. The method according to claim 1, wherein one or more types of resin, flakes, or powder are blended with different concentrations of an antioxidant.

4. The method according to claim 1, wherein the polymeric material is further homogenized following the irradiation step by heating to below the melt to allow diffusion of the antioxidant from the antioxidant rich to antioxidant poor regions and oxidative stability throughout the polymeric material.

5. The method according to claim 1, wherein the polymeric material is homogenized before and/or after irradiation, by thermally annealing at a temperature below the melting point of the polymeric material.

6. The method according to claim 1, wherein the highly cross-linked, oxidatively stable, and highly crystalline polymeric material is further doped with an antioxidant by diffusion at a temperature below the melting point of the polymeric material.

7. The method according to claim 6, wherein the doping is carried out by soaking the medical implant in the antioxidant for about 0.1 hours to about 72 hours.

8. The method according to claim 1, wherein the antioxidant is vitamin E.

9. The method according to claim 1, wherein a portion or all of the highly cross-linked, oxidatively stable, and highly crystalline polymeric material is further thermally annealed below the melting point of the polymeric material.

10. The method according to claim 1, wherein the antioxidant blended polymeric material, the consolidated polymeric material, or the highly cross-linked, oxidatively stable, and highly crystalline polymeric material is compression molded to another piece or a medical implant, thereby forming an interface or an interlocked hybrid material.

11. The method according to claim 1, wherein the polymeric material is a polyolefin, a polypropylene, a polyamide, a polyether ketone, a hydrogel or a mixture thereof.

12. The method according to claim 11, wherein the polyolefin is selected from a group consisting of a low-density polyethylene, high-density polyethylene, linear low-density polyethylene, ultra-high molecular weight polyethylene (UHMWPE), or a mixture thereof.

13. The method according to claim 1, wherein the irradiation is carried out in an atmosphere containing between about 1% and about 22% oxygen.

14. The method according to claim 1, wherein the irradiation is carried out in an inert atmosphere, and wherein the atmosphere contains gases selected from the group consisting of nitrogen, argon, helium, neon, or the like, and a combination thereof.

15. The method according to claim 1, wherein the radiation dose is about 65 kGy.

16. The method according to claim 1, wherein the irradiated polymeric material is thermally annealed in contact with a non-oxidizing medium, thereby achieving reduction of free radicals in the cross-linked polymeric material, wherein the non-oxidizing medium is an inert gas, an inert fluid, or a polyunsaturated hydrocarbon selected from the group consisting of acetylenic hydrocarbons such as acetylene; conjugated or unconjugated olefinic hydrocarbons such as butadiene and (meth)acrylate monomers; and sulphur monochloride with chloro-tri-fluoroethylene (CTFE) or acetylene.

17. The method according to claim 1, wherein the highly cross-linked, oxidatively stable, and highly crystalline polymeric material is further homogenized at a temperature below the melting point of the polymeric material for a period of about an hour to several days.

18. The method according to claim 1, wherein the highly cross-linked, oxidatively stable, and highly crystalline polymeric material is further homogenized at a temperature below melting point.

19. The method according to claim 1, wherein the consolidated polymeric material is irradiated at a temperature of about 40° C.

20. The method according to claim 1, wherein the consolidated polymeric material is irradiated at a temperature that is above the room temperature and below 135° C.

21. The method according to claim 1, wherein the radiation dose is between about 25 and about 1000 kGy.

22. The method according to claim 1, wherein the radiation dose is about 75 kGy.

23. The method according to claim 1, wherein the radiation dose is about 65 kGy.

24. The method according to claim 1, wherein the consolidated polymeric material is irradiated at a temperature of about 135° C.

25. The method according to claim 1, wherein the consolidated polymeric material is irradiated at a temperature of about 130° C.

26. The method according to claim 1, wherein the consolidated polymeric material is irradiated at a temperature of about 120° C.

27. The method according to claim 1, wherein the consolidated polymeric material is irradiated at a temperature of about 110° C.

28. The method according to claim 1, wherein the consolidated polymeric material is irradiated at a temperature of about 100° C.

29. The method according to claim 1, wherein the consolidated polymeric material is irradiated at a temperature of about 75° C.

30. A method of making highly cross-linked, oxidatively stable, and highly crystalline polymeric material comprising:
   a) blending antioxidant with UHMWPE resin, powder, or flake in the absence of a supercritical fluid, thereby providing a polymeric blend, wherein the blend is mixed with virgin UHMWPE resin, powder, or flake, thereby forming a composition having antioxidant rich and poor regions;
   b) consolidating the blend from step (a) to provide a consolidated polymeric material having antioxidant rich and poor regions;
   c) irradiating the consolidated polymeric material from step (b) at a temperature that is above the room temperature and below the melting point of the polymeric material to provide an irradiated and consolidated polymeric material having antioxidant rich and poor regions; and
   d) quenching residual free radicals by annealing the irradiated and consolidated polymeric material in air or under an inert environment at a temperature below the melting temperature of the polymeric material, thereby forming a highly cross-linked, oxidatively stable, and highly crystalline polymeric material.

31. The method according to claim 30, wherein residual free radicals in the irradiated polymeric material are quenched by annealing in air or under an inert environment at a temperature below or above the melting temperature of the polymeric material.

* * * * *